(12) United States Patent
Achilefu et al.

(10) Patent No.: US 11,007,286 B2
(45) Date of Patent: *May 18, 2021

(54) COMPOSITIONS AND METHODS FOR TREATMENT AND IMAGING USING NANOPARTICLES

(71) Applicant: The Washington University, St. Louis, MO (US)

(72) Inventors: Samuel Achilefu, St. Louis, MO (US); Kvar Black, St. Louis, MO (US)

(73) Assignee: Washington University, St. Louis, MO (US)

( * ) Notice: Subject to any disclaimer, the term of this patent is extended or adjusted under 35 U.S.C. 154(b) by 18 days.

This patent is subject to a terminal disclaimer.

(21) Appl. No.: 15/959,982

(22) Filed: Apr. 23, 2018

(65) Prior Publication Data

US 2019/0001004 A1 Jan. 3, 2019

Related U.S. Application Data

(63) Continuation of application No. 14/734,761, filed on Jun. 9, 2015, now Pat. No. 9,974,870.

(60) Provisional application No. 62/009,481, filed on Jun. 9, 2014, provisional application No. 62/137,628, filed on Mar. 24, 2015.

(51) Int. Cl.
*A61K 51/08* (2006.01)
*A61K 51/12* (2006.01)

(52) U.S. Cl.
CPC ........ *A61K 51/088* (2013.01); *A61K 51/1251* (2013.01)

(58) Field of Classification Search
CPC ...... A61K 51/00; A61K 51/08; A61K 51/088; A61K 51/251; A61K 2123/00; A61K 2121/00
USPC ........ 424/1.11, 1.65, 1.69, 9.1, 9.2, 9.3, 9.4, 424/9.5, 9.6
See application file for complete search history.

(56) References Cited

U.S. PATENT DOCUMENTS

| | | | |
|---|---|---|---|
| 4,551,482 A | 11/1985 | Tschang et al. | |
| 5,179,120 A | 1/1993 | Vogel et al. | |
| 5,490,840 A | 2/1996 | Uzgiris et al. | |
| 5,510,103 A | 4/1996 | Yokoyama et al. | |
| 5,574,172 A | 11/1996 | Katsuro et al. | |
| 5,651,991 A | 7/1997 | Sugiyama et al. | |
| 5,688,931 A | 11/1997 | Nogusa et al. | |
| 5,714,166 A | 2/1998 | Tomalia et al. | |
| 5,786,387 A | 7/1998 | Watanabe et al. | |
| 5,855,900 A | 1/1999 | Nobuhiko | |
| 5,858,410 A | 1/1999 | Muller et al. | |
| 5,922,356 A | 7/1999 | Koseki et al. | |
| 5,922,545 A | 7/1999 | Mattheakis et al. | |
| 5,994,392 A | 11/1999 | Shashoua | |
| 6,106,866 A | 8/2000 | Ranney | |
| 6,127,339 A | 10/2000 | Hatanaka et al. | |
| 9,974,870 B2 * | 5/2018 | Achilefu | ............ A61K 51/1251 |
| 2006/0019876 A1 | 1/2006 | Faulk | |
| 2007/0218049 A1 | 9/2007 | Chen et al. | |
| 2007/0292353 A1 | 12/2007 | Levy et al. | |
| 2009/0202650 A1 | 8/2009 | Hwu et al. | |
| 2009/0220430 A1 | 9/2009 | Rajpadhye et al. | |
| 2010/0209479 A1 | 8/2010 | Carroll et al. | |
| 2012/0101427 A1 | 4/2012 | Farmer et al. | |
| 2012/0220870 A1 | 8/2012 | Gambhir et al. | |
| 2012/0282185 A1 | 11/2012 | Dobson et al. | |
| 2013/0017266 A1 | 1/2013 | Ogino et al. | |
| 2013/0137916 A1 | 5/2013 | Goer | |
| 2017/0007724 A1 | 1/2017 | Achilefu et al. | |

FOREIGN PATENT DOCUMENTS

WO   2015183346 A2   12/2015

OTHER PUBLICATIONS

Office Action dated Oct. 5, 2018 from related U.S. Appl. No. 15/115,457; 8 pgs.
Apel, K. et al., "Reactive Oxygen Species: Metabolism, Oxidative, Stress, and Signal Transduction," Annu. Rev. Plant Biol., 2004, 373-399, vol. 55, with Figures, 2 pgs.
Ashkenazi et al., "Death Receptors: Signaling and Modulation," Science, Aug. 28, 1998, pp. 1305-1308, vol. 281.
Beattie, B. et al., "Quantitative Modeling of Cerenkov Light Production Efficiency from Medical Radionuclides," PLoS One, Feb. 2012, pp. 1-13, vol. 7, No. 2, e31402.
Beekman et al., "The pinhole: gateway to ultra-high-resolution three-dimensional radionuclide imaging," Eur. J. Nucl. Med. Mol. Imaging, Feb. 2007, pp. 151-161, vol. 34, No. 2.
Benard et al., "Imaging in breast cancer: Single-photon computer tomography and positron-emission tomography," Breast Cancer Research, Jul. 2005, pp. 153-162, vol. 7, No. 4.
Black et al., "Bacterial Killing by Light-Triggered Release of Silver from Biomimetic Metal Nanorods," Small, Author Manuscript, Jan. 15, 2015, pp. 1-20; Small, Jan. 15, 2014, pp. 169-178, vol. 10, No. 1.
Black et al., "Polydopamine-enabled surface functionalization of gold nanorods for cancer cell-targeted imaging and photothermal therapy," Nanomedicine, Jan. 2013, pp. 17-28, vol. 8, No. 1.
Black et al., "Radioactive 198Au-Doped Nanostructures with Different Shapes for In Vivo Analyses of Their Biodistribution, Tumor Uptake, and Intratumoral Distribution," ACS Nano., 2014, pp. 4385-4394, vol. 8, No. 5.
Boehm, H., "Acidic and basic properties of hydroxylated metal oxide surfaces," Discussions of the Faraday Society, 1971, pp. 264-275, Nol. 52.

(Continued)

*Primary Examiner* — D. L. Jones
(74) *Attorney, Agent, or Firm* — Polsinelli PC

(57) ABSTRACT

The present invention encompasses compositions comprising two spectrally distinct radionuclides separated by a site susceptible to cleavage. Compositions of the invention may be used to detect enzyme activity and/or image diseases associated with said enzyme activity.

12 Claims, 25 Drawing Sheets
(21 of 25 Drawing Sheet(s) Filed in Color)
Specification includes a Sequence Listing.

(56) References Cited

OTHER PUBLICATIONS

Boya et al., "Lysosomal membrane permeabilization in cell death," Oncogene, 2008, pp. 6434-6451, vol. 27.
Bremer et al., "In vivo molecular target assessment of matrix metalloproteinase inhibition," Nature Medicine, Jun. 2001, pp. 743-748, vol. 7, No. 6.
Brown, S. et al., "The present and future role of photodynamic therapy in cancer treatment," Lancet Oncol., Aug. 2004, pp. 497-508, vol. 5.
Bullok et al., "Biochemical and in Vivo Characterization of a Small, Membrane-Permeant, Caspase-Activatable Far-Red Fluorescent Peptide for Imaging Apoptosis," Biochemistry, 2007, pp. 4055-4065, vol. 46, No. 13.
Chatterjee, D. et al., "Nanoparticles in photodynamic therapy: Ac emerging paradigm," Adv. Drug. Deliv. Rev., Dec. 14, 2008, pp. 1627-1637, vol. 60, No. 15, Elsevier B.V.
Chau et al., Matrix metalloproteinase inhibitors—an emphasis on gastrointestinal malignancies, Critical Reviews in Oncology/Hematology, 2003, pp. 151-176, vol. 45.
Chen et al., "Radiolabeled isatin binding to caspase-3 activation induced by anti-Fas antibody," NIH Public Access Author Manuscript, Jan. 1, 2013, pp. 1-15; Nucl. Med. Biol., Jan. 2012, pp. 137-144, vol. 39, No. 1.
Chithrani, D. et al., "Gold Nanoparticles as Radiation Sensitizers in Cancer Therapy," Radiat. Res., 2010, pp. 719-728, vol. 173, Radiation Research Society.
Choi et al., "Protease-Activated Drug Development," Theranostics, 2012, pp. 156-178, vol. 2, No. 2.
Cobley, C. et al., "Gold nanostructures: a class of multifunctional materials for biomedical applications," Chem. Soc. Rev., 2011, pp. 44-56, vol. 40, The Royal Society of Chemistry.
Dolmans, D. et al., "Photodynamic therapy for cancer," Nat. Rev. Cancer, May 2003, pp. 380-387, vol. 3, Nature Publishing Group.
Eckelman et al., True Radiotracers: are we approaching theoretical specific activity with Tc-99m and I-123?, Nuc. Med. Biol., 2008, pp. 523-527, vol. 35.
Edwards, et al., "Multimodal Imaging of Integrin Receptor-Positive Tumors by Bioluminescence, Fluorescence, Gamma Scintigraphy and SPECT Methods Using a Cyclic RGD Peptide Labeled with a Near Infrared Fluorescent Dye and a Radionuclide," NIH Public Access Author Manuscript, Nov. 8, 2010, pp. 1-21; Mol. Imaging, 2009, pp. 101-110, vol. 8, No. 2.
Ethirajan, M., et al., "The role of porphyrin chemistry in tumor imaging and photodynamic therapy," Chem. Soc. Rev., 2011, pp. 340-362, vol. 40, No. 1, The Royal Society of Chemistry.
Fung, L. et al., "Polymeric implants for cancer chemotherapy," Adv. Drug. Deilv. Rev., Jul. 1, 1997, pp. 209-230, vol. 26, Nos. 2-3, Elsevier Science B.V.
Gatter, K. et al., "Transferrin receptors in human tissues: their distribution and possible clinical relevance," J. Clin. Pathol., 1983, pp. 539-545, vol. 36.
Glazer et al., "SPECT/CT Evaluation of Unusual Physiologic Radio-iodine Biodistributions: Pearls and Pitfalls in Image Interpretation," RadioGraphics, Mar.-Apr. 2013, pp. 397-418, vol. 33, with Teaching Points, 1 pg.
Goldman, C. et al., "Targeted Gene Delivery to Kaposi's Sarcoma via the Fibroblast Growth Factor Receptor," Cancer Res., Apr. 15, 1997, pp. 1447-1451, vol. 57, American Association for Cancer Research.
Graham, "Clinical Molecular Imaging With Radiotracers: Current Status," Med. Princ. Pract., 2012, pp. 197-208, vol. 21.
Holt, A., et al., "Transarterial Radioembolization with Yttrium-90 for Regional Management of Hepatocellular Cancer: The Early Results of a Nontransplant Center," Am. Surg., Oct. 2010, pp. 1079-1083, vol. 76, No. 10, Southeastern Surgical Congress.
Hu, Z., et al. Three-dimensional Noninvasive Monitoring Iodine-131 Uptake in the Thyroid Using a Modified Cerenkov Luminescence Tomography Approach, PLoS One, May 2012, pp. 1-12, vol. 7, No. 5, e37623.
Huang et al., "Gold Nanoparticles: interesting optical properties and recent applications in cancer diagnostics and therapy," Nanomedicine, 2007, pp. 681-693, vol. 2, No. 5.
Hutchinson, F., "The Distance That a Radical Formed by Ionizing Radiation Can Diffuse in a Yeast Cell," Radiat Res., Nov. 1957, pp. 473-483, vol. 7, No. 5, Radiation Research Society.
International Search Report and Written Opinion from related International Patent Application No. PCT/US2015/014095, dated Oct. 6, 2015, 11 pgs.
Jelley, J., "Cerenkov radiation and its applications," Br. J. Appl. Phys., Jul. 1955, pp. 227-232, vol. 6, No. 7.
Johansson et al., "Regulation of apoptosis-associated lysosomal membrane permeabilization," Apoptosis, 2010, pp. 527-540, vol. 15.
Kelloff, G. et al., "Progress and Promise of FDG-PET Imaging for Cancer Patient Management and Oncologic Drug Development," Clin. Cancer Res., Apr. 15, 2005, pp. 2785-2808, vol. 11, No. 8, American Association for Cancer Research.
Kotagiri, N. et al., "Activatable Probes Based on Distance-Dependent Luminescence Associated with Cerenkov Radiation," Angew. Chem. Int. Ed., Jul. 22, 2013, pp. 7756-7760, vol. 52, No. 30, Wiley-VCH Verlag GmbH & Co. KGaA, Weinheim.
Lee et al., "Complementary optical and nuclear imaging of caspase-3 activity using combined activatable and radiolabeled multimodality molecular probe," NIH Public Access Author Manuscript, Aug. 4, 2010, pp. 1-9; J. Biomed. Opt., 2009, vol. 14, No. 4.
Lewis, J. et al., "Radiotherapy and Dosimetry of 64Cu-TETA-Tyr3-Octreotate in a Somatostatin Receptor-Positive, Tumor-Bearing Rat Model," Clin. Cancer Res., Nov. 1999, pp. 3608-3616, vol. 5, American Association for Cancer Research.
Liu, H., et al., "Molecular Optical Imaging with Radioactive Probes," PLoS One, Mar. 2010, pp. 1-9, vol. 5, No. 3, e9470.
Luker et al., "Optical Imaging: Current Applications and Future Directions," J. Nucl. Med., 2008, pp. 1-4, vol. 49, No. 1.
Ma et al., "Targeting Chk1 in p53-deficient triple-negative breast cancer is therapeutically beneficial in human-in-mouse tumor models," J. Clinical Investigation, Apr. 2012, pp. 1541-1552, vol. 122, No. 4.
Maitra, A. et al., "Pancreatic Cancer," Annu. Rev. Pathol. Mech. Dis., Feb. 28, 2008, pp. 157-188, vol. 3, Annual Reviews.
Manome, Y. et al., "Enhancer Sequences of the DF3 Gene Regulate Expression of the Herpes Simplex Virus Thymidine Kinase Gene and Confer Sensitivity of Human Breast Cancer Cells to Ganciclovir," Cancer Res., Oct. 15, 1994, pp. 5408-5413, vol. 54, American Association for Cancer Research.
Mathis et al., "Oncolytic adenoviruses—selective retargeting to tumor cells," Oncogene, 2005, pp. 7775-7791, vol. 24.
Mebrahtu et al., "Initial characterization of a dually radiolabeled peptide for simultaneous monitoring of protein targets and enzymatic activity," Nucl. Med. Biol., 2013, pp. 190-196, vol. 40.
Mitchell, G. et al., "In vivo Cerenkov luminescence imaging: a new tool for molecular imaging," Phil. Trans. R. Soc. A, 2011, pp. 4605-4619, vol. 369, The Royal Society.
Moghimi, S. et al., "Long-Circulating and Target-Specific Nanoparticles: Theory to Practice," Pharmacol. Rev., 2001, pp. 283-318, vol. 53, No. 2, The American Society for Pharmacology and Experimental Therapeutics.
Notice of Allowance and Examiner Initiated Interview Summary dated Jan. 23, 2018 for related U.S. Appl. No. 14/734,761; 10 pgs.
Ntziachristos et al., "In Vivo Tomographic Imaging of Near-Infrared Fluorescent Probes," Molecular Imaging, Apr. 2002, pp. 82-88, vol. 1, No. 2.
Office Action dated May 31, 2019 from related U.S. Appl. No. 15/115,457; 7 pgs.
Office Action dated Mar. 23, 2017 from related U.S. Appl. No. 14/734,761; 12 pgs.
Office Action dated Sep. 18, 2017 from related U.S. Appl. No. 14/734,761; 24 pgs.
Olson et al., "Activatable cell penetrating peptides linked to nanoparticles as dual probes for in vivo fluorescence and MR imaging of proteases," PNAS, Mar. 2, 2010, pp. 4311-4316, vol. 107, No. 9.
Peer et al., "Nanocarriers as an emerging platform for cancer therapy," Nature Nanotechnology, Dec. 2007, pp. 751-760, vol. 2.

(56) References Cited

OTHER PUBLICATIONS

Qian, Z. et al., "Targeted Drug Delivery via the Transferrin Receptor-Mediated Endocytosis Pathway," Pharmacol. Rev., 2002, pp. 561-587, vol. 54, No. 4, The American Society for Pharmacology and Experimental Therapeutics.
Robertson, R. et al., "Optical imaging of Cerenkov light generation from positron-emitting radiotracers," NIH Public Access Author Manuscript, available in PMC Aug. 21, 2010, pp. 1-13, Published in final form as: Phys. Med. Biol., Aug. 21, 2009, pp. N355-N365, vol. 54, No. 16.
Rozhkova, E. et al., "A High-Performance Nano-Bio Photocatalyst for Targeted Brain Cancer Therapy," NIH Public Access Author Manuscript, available in PMC May 14, 2014, pp. 1-12, Published in final edited form as: Nano Lett., Sep. 2009, pp. 3337-3342, vol. 9, No. 9, American Chemical Society.
Shi, H. et al., "Real-Time Monitoring of Cell Apoptosis and Drug Screening Using Fluorescent Light-Up Probe with Aggregation-Induced Emission Characteristics," J. Am. Chem. Soc., 2012, pp. 17972-17981, vol. 134, American Chemical Society.
Solomon et al., "Detection of enzyme activity in orthotopic murine breast cancer by fluorescence lifetime imaging using a fluorescence resonance energy transfer-based molecular probe," J. Biomedical Optics, Jun. 2011, pp. 066019-1-066019-6, vol. 16, No. 6.
Spinelli, A. et al., "Multispectral Cerenkov luminescence tomography for small animal optical imaging," Opt. Express, Jun. 20, 2011, pp. 12605-12618, vol. 19, No. 13, Optical Society of America.
Spring, B. et al., "Selective treatment and monitoring of disseminated cancer micrometastases in vivo using dual-function, activatible immunoconjugates," PNAS, Feb. 26, 2014, pp. E933-E942, vol. 111, No. 26.
Thorek, D. et al., "Quantitative imaging of disease signatures through radioactive decay signal conversion," Nat. Med., Oct. 2013, pp. 1345-1350, vol. 19, No. 10, Nature America, Inc.
Turchi, C. et al., "Photocatalytic Degradation of Organic Water Contaminants: Mechanisms Involving Hydroxyl Radical Attack," J. Catalysis, 1990, pp. 178-192, vol. 122, Academic Press, Inc.
Van Schaijk et al., "Residualizing Iodine Markedly Improved Tumor Targeting Using Bispecific Antibody-Based Pretargeting," J. Nucl. Med., Jun. 2005, pp. 1016-1022, vol. 46.
Vaupel, P. et al., "Blood Flow, Oxygen and Nutrient Supply, and Metabolic Microenvironment of Human Tumors: A Review," Cancer Res., Dec. 1, 1989, pp. 6449-6465, vol. 49, American Association for Cancer Research.
Wang et al., "A Comparison Study of Gold Nanohexapods, Nanorods, and Nanocages for Photothermal Cancer Treatment," NIH Public Access Author Manuscript, Mar. 26, 2014, pp. 1-20; ACS Nano., Mar. 26, 2013, pp. 2068-2077, vol. 7, No. 3.
Wang et al., "Evaluating the Pharmacokinetics and in vivo Cancer Targeting Capability of Au Nanocages by Positron Emission Tomography Imaging," NIH Public Access Author Manuscript, Jul. 24, 2013, pp. 1-17; ACS Nano., Jul. 24, 2012, pp. 5880-5888, vol. 6, No. 7.
Wang et al., "Radioluminescent Gold Nanocages with Controlled Radioactivity for Real-time In Vivo Imaging," NIH Public Access Author Manuscript, Feb. 13, 2014, pp. 1-10; Nano Lett., Feb. 13, 2013, pp. 581-585, vol. 13, No. 2.
Wang et al., "Roles of caspases in apoptosis, development, and cytokine maturation revealed by homozygous gene deficiencies," J. Cell Science, 2000, pp. 753-757, vol. 113.
Wang, S. et al., "Nanomaterials and singlet oxygen photosensitizers: potential applications in photodynamic therapy," J. Mater. Chem., 2004, pp. 487-493, vol. 14, The Royal Society of Chemistry.
Yang et al., "Anticancer Therpay and Apoptosis Imaging," Exp. Oncol., Sep. 2012, pp. 269-276, vol. 34, No. 3.
Yu, B., "Cellular Defenses Against Damage From Reactive Oxygen Species," Physiol. Rev., Jan. 1994, pp. 139-162, vol. 74, No. 1, American Physiological Society.
Zeng et al., "Cu Core-labeled Nanoparticles with High Specific Activity via Metal-Free Click Chemistry," NIH Public Access Author Manuscript, Jun. 26, 2013, pp. 1-25; ACS Nano., Jun. 26, 2012, pp. 5209-5219, vol. 6, No. 6.
Zhang et al., "Actiavtable Molecular Systems Using Homologous Near-Infrared Fluorescent Probes for Monitoring Enzyme Activities in Vitro, in Cellulo, and in Vivo," Molecular Pharmaceutics, Aug. 5, 2008, pp. 416-427, vol. 6, No. 2.
Zhao et al., "Copper-64-Alloyed Gold Nanoparticles for Cancer Imaging: Improved Radiolabeled Stability and Diagnostic Accuracy," Angew. Chem. Int. Ed., 2014, pp. 156-159, vol. 53.
Cherry, S. et al., "PET: Physics, Instrumentation, and Scanners," Physics of Positron Emission and Annihilation, pp. 1-117, ISBN 978-0-387-34946-6, Springer Science+Business Media, LLC, 2006.
Grisham, M., "Reactive Metabolites of Oxygen and Nitrogen in Biology and Medicine," 1992, ISBN 187970224X, 104 pgs., Landes.
Wilson, B. (Dubowski, J. & Tanev, S. eds.), "Photonic and Non-Photonic Based Nanoparticles in Cancer Imaging and Therapeutics," Photon-based Nanoscience and Nanobiotechnology, 2006, pp. 121-157, vol. 239, ISBN 9781402055232, Springer Science & Business Media.
Office Action dated Oct. 7, 2020 from related U.S. Appl. No. 15/115,457; 7 pgs.

\* cited by examiner

SEQUENCE LISTING

<160> NUMBER OF SEQ ID NOS: 6

<210> SEQ ID NO 1
<211> LENGTH: 13
<212> TYPE: PRT
<213> ORGANISM: Artificial Sequence
<220> FEATURE:
<223> OTHER INFORMATION: SYNETHESIZED
<220> FEATURE:
<221> NAME/KEY: misc_feature
<222> LOCATION: (12)..(12)
<223> OTHER INFORMATION: Xaa = Aminocaproic acid

<400> SEQUENCE: 1

Gly Pro Leu Gly Val Arg Gly Lys Gly Tyr Gly Xaa Cys
1               5                   10

<210> SEQ ID NO 2
<211> LENGTH: 4
<212> TYPE: PRT
<213> ORGANISM: Artificial Sequence
<220> FEATURE:
<223> OTHER INFORMATION: SYNTHESIZED

<400> SEQUENCE: 2

Asp Glu Val Asp
1

<210> SEQ ID NO 3
<211> LENGTH: 11
<212> TYPE: PRT
<213> ORGANISM: Artificial Sequence
<220> FEATURE:
<223> OTHER INFORMATION: SYNTHESIZED
<220> FEATURE:
<221> NAME/KEY: misc_feature
<222> LOCATION: (5)..(5)
<223> OTHER INFORMATION: Xaa = Ornithine

<400> SEQUENCE: 3

Gly Arg Arg Arg Xaa Arg Arg Lys Lys Arg Lys
1               5                   10

<210> SEQ ID NO 4
<211> LENGTH: 7
<212> TYPE: PRT
<213> ORGANISM: Artificial Sequence
<220> FEATURE:
<223> OTHER INFORMATION: SYNTHESIZED
<220> FEATURE:
<221> NAME/KEY: misc_feature
<222> LOCATION: (5)..(5)
<223> OTHER INFORMATION: Xaa = Aminocaproic acid

<400> SEQUENCE: 4

Tyr Leu Ala Ile Xaa Pro Ala
1               5

<210> SEQ ID NO 5
<211> LENGTH: 11
<212> TYPE: PRT
<213> ORGANISM: Artificial Sequence
<220> FEATURE:
<223> OTHER INFORMATION: SYNTHESIZED
<220> FEATURE:
<221> NAME/KEY: MISC_FEATURE
<222> LOCATION: (1)..(1)
<223> OTHER INFORMATION: Xaa = Aminocaproic acid

```
<220> FEATURE:
<221> NAME/KEY: MISC_FEATURE
<222> LOCATION: (3)..(3)
<223> OTHER INFORMATION: Xaa = Aminocaproic acid

<400> SEQUENCE: 5

Xaa Tyr Xaa Asp Glu Val Asp Gly Lys Gly Cys
1               5                   10

<210> SEQ ID NO 6
<211> LENGTH: 22
<212> TYPE: PRT
<213> ORGANISM: Artificial Sequence
<220> FEATURE:
<223> OTHER INFORMATION: SYNTHESIZED
<220> FEATURE:
<221> NAME/KEY: MISC_FEATURE
<222> LOCATION: (5)..(5)
<223> OTHER INFORMATION: Xaa = Aminocaproic acid
<220> FEATURE:
<221> NAME/KEY: misc-feature
<222> LOCATION: (16)..(16)
<223> OTHER INFORMATION: Xaa = Ornithine

<400> SEQUENCE: 6

Tyr Leu Ala Ile Xaa Pro Ala Asp Glu Val Asp Gly Arg Arg Arg Xaa
1               5                   10                  15

Arg Arg Lys Lys Arg Lys
            20
```

COMPOSITIONS AND METHODS FOR TREATMENT AND IMAGING USING NANOPARTICLES

CROSS REFERENCE TO RELATED APPLICATIONS

This application is a continuation of U.S. application Ser. No. 14/734,761 filed Jun. 9, 2015 which claims the priority of U.S. provisional application No. 62/009,481, filed Jun. 9, 2014 and U.S. provisional application No. 62/137,628, filed Mar. 24, 2015, each of which is hereby incorporated by reference in its entirety.

GOVERNMENTAL RIGHTS

This invention was made with government support under HHSN268201000046C awarded by the National Institutes of Health; and under W81XWH-09-1-0333 awarded by the ARMY/MRMC. The government has certain rights in the invention.

FIELD OF THE INVENTION

The present invention encompasses compositions comprising two spectrally distinct radionuclides separated by a site susceptible to cleavage. Compositions of the invention may be used to detect enzyme activity and/or image diseases associated with said enzyme activity.

BACKGROUND OF THE INVENTION

Imaging agents that activate under specific conditions, for example under low pH or in the presence of an enzyme, have the ability to provide molecular, biological, and physiologically specific contrast. Most often, these activatable probes are optical in nature, wherein an emitter is linked with a quencher by a cleavable domain. This has allowed for the characterization and imaging of not just binding events, but other biological processes such as enzyme activity. The activatable optical contrast agents, however, are hampered by their poor tissue penetration, which has limited their clinical translatability in many areas. Therefore, a nuclear activatable alternative is highly desired in order to fulfill the promise of this class of imaging agent.

SUMMARY OF THE INVENTION

In an aspect, the present invention encompasses a composition. The composition comprises a cleavable peptide and two distinct radionuclides, wherein the radionuclides are separated by a site susceptible to cleavage by an enzyme and can be spectrally differentiated.

In another aspect, the present invention encompasses a method of detecting enzyme activity associated with a disease or condition in a subject. The method comprises (a) administering to the subject an effective amount of a composition comprising: a cleavable peptide and a first and second radionuclide, wherein the first and second radionuclide are separated by a site susceptible to cleavage by an enzyme and can be spectrally differentiated; (b) imaging the subject for a signal corresponding to the first and second radionuclide; and (c) comparing the biodistribution of the first radionuclide to the biodistribution of the first radionuclide, wherein when the biodistribution for the first radionuclide differs from the biodistribution for the second radionuclide, enzyme activity is detected.

BRIEF DESCRIPTION OF THE FIGURES

The patent or application file contains at least one drawing executed in color. Copies of this patent or patent application with color drawing(s) will be provided by the Office upon request and payment of the necessary fee.

DETAILED DESCRIPTION OF THE INVENTION

Figure 1:
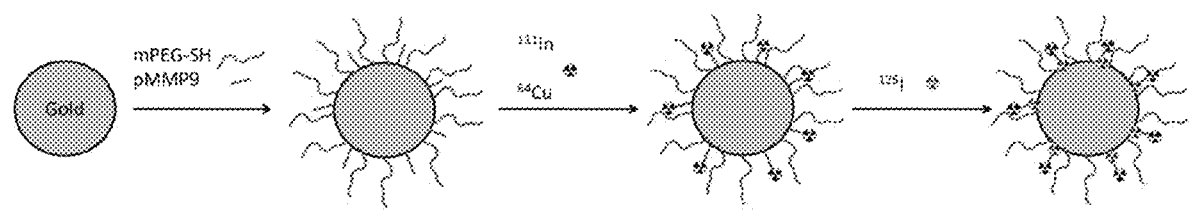
FIG. 1 depicts a schematic of the synthesis of the dual-radiolabeled nanoparticle-based SPECT probes.

Single photon emission computed tomography (SPECT) radionuclide pairs having distinct decay rates and different energy maxima enable simultaneous detection of dual gamma signals and real-time assessment of dynamic functional and molecular processes in vivo. Disclosed herein is a molecular framework for developing and using dual radionuclide-labeled imaging agents for the molecular imaging of aberrant intracellular or extracellular proteases. The compositions disclosed herein may be used to determine enzyme activity and ultimately therapeutic response which can help identify nonresponders at early time points, giving an opportunity to apply an alternative and potentially more effective treatment. The inventors have shown that cleavable peptides may be radiolabeled with different radionuclides, specifically dual SPECT isotopes, $^{125}$I with $^{99m}$Tc or $^{111}$In. Results demonstrate the potential of using multiradionuclide-resolving power of clinically useful SPECT for noninvasively monitoring treatment response.

I. Composition

In an aspect, the present invention encompasses a composition comprising: a cleavable peptide and two distinct radionuclides, wherein the radionuclides are separated by a site susceptible to cleavage by an enzyme and can be spectrally differentiated.

In another aspect, the present invention encompasses a composition comprising: a nanoparticle, a cleavable peptide and two distinct radionuclides, wherein the radionuclides are separated by a site susceptible to cleavage by an enzyme and can be spectrally differentiated. In certain embodiments, the radionuclides are both conjugated to the cleavable peptide on either side of the site susceptible to cleavage by an enzyme. In other embodiments, the nanoparticle comprises a radionuclide and the cleavable peptide comprises a radionuclide, such that cleavage of the peptide releases the radionuclide conjugated to the peptide.

(a) Cleavable Peptide

The present disclosure encompasses cleavable peptides. By "peptide" is meant an amino acid sequence that includes 5 or more amino acid residues. "Peptide" refers to both short chains, commonly referred to as peptides, oligopeptides, or oligomers, and to longer chains, up to about 100 residues in length. A peptide may comprise about 5 or more amino acids. For example, a peptide may comprise about 5 or more, about 10 or more, about 15 or more, about 20 or more, about 25 or more, about 30 or more, about 35 or more, about 40 or more, about 45 or more, about 50 or more, about 55 or more, about 60 or more, about 65 or more, about 70 or more, about 75 or more, about 80 or more, about 85 or more, about 90 or more, about 95 or more, or about 100 or more amino acids. In certain embodiments, a peptide may comprise 5, 6, 7, 8, 9, 10, 11, 12, 13, 14, 15, 16, 17, 18, 19, 20, 21, 22, 23, 24 or 25 amino acids. In an embodiment, a peptide may comprise about 5 to about 10 amino acids. In other embodiments, a peptide may comprise from about 10 to about 20 amino acids. In a different embodiment, a peptide may comprise from about 20 to about 25 amino acids. In still other embodiments, a peptide may comprise from about 10 to about 15 amino acids. In yet other embodiments, a peptide may comprise from about 15 to about 20 amino acids. In a specific embodiment, a peptide may comprise about 13 amino acids. In another specific embodiment, a peptide may comprise about 9 amino acids. In still another specific embodiment, a peptide may comprise about 21 amino acids.

A peptide may comprise a positively charged or hydrophilic amino acid sequence and/or a hydrophobic amino acid sequence. Without wishing to be bound by theory, positively charged or hydrophilic amino acids may enhance internalization of the peptide. In a specific embodiment, a peptide may comprise a hydrophilic amino acid sequence and a hydrophobic amino acid sequence separated by a site susceptible to cleavage. Non-limiting examples of positively charged amino acids include arginine, lysine and ornithine. Non-limiting examples of hydrophobic amino acids include alanine, isoleucine, leucine, phenylalanine, valine, proline, glycine and aminocaproic acid. In a specific embodiment, a hydrophilic amino acid sequence may comprise SEQ ID NO:3 (Gly-Arg-Arg-Arg-Orn-Arg-Arg-Lys-Lys-Arg-Lys). In another specific embodiment, a hydrophobic amino acid sequence may comprise SEQ ID NO:4 (Tyr-Leu-Ala-Ile-Ahx-Pro-Ala).

A "cleavable peptide" as used herein is a peptide that comprises a site susceptible to cleavage by an enzyme. In specific embodiments, the enzyme is an enzyme that is associated with a disease or condition. In some embodiments the disease or condition is cancer, cardiovascular disease, arthritis, viral, bacterial, parasitic or fungal infection, Alzheimer's disease, emphysema, thrombosis, hemophilia, stroke, organ dysfunction, any inflammatory condition, vascular disease, parenchymal disease, or a pharmacologically-induced state. Non-limiting examples of sites susceptible to cleavage include a MMP sensitive site, a caspase-sensitive site, a kallikrein sensitive site, a cathepsin sensitive site, a plasminogen activator sensitive site and/or an ADAM sensitive site. In certain embodiments, the cleavable peptide comprises a caspase-sensitive site. Caspases, or cysteine-aspartic proteases or cysteine-dependent aspartate-directed proteases, are a family of cysteine proteases that play essential roles in apoptosis (programmed cell death), necrosis, and inflammation. There are two types of apoptotic caspases: initiator (apical) caspases and effector (executioner) caspases. Initiator caspases (e.g., caspase-2, caspase-8, caspase-9, and caspase-10) cleave inactive pro-forms of effector caspases, thereby activating them. Effector caspases (e.g., caspase-3, caspase-6, caspase-7) in turn cleave other protein substrates within the cell, to trigger the apoptotic process. In a specific embodiment, the cleavable peptide comprises a caspase-3 or caspase-7 sensitive site. The caspase-sensitive site may comprise SEQ ID NO:2 (Asp-Glu-Val-Asp). In certain embodiments, the cleavable peptide comprises a MMP sensitive site. MMPs (matrix metalloproteinases) are zinc-dependent endopeptidases capable of degrading all kinds of extracellular matrix proteins, but also can process a number of bioactive molecules. MMPs are known to be involved in the cleavage of cell surface receptors, the release of apoptotic ligands (such as the FAS ligand), and chemokine/cytokine inactivation. MMPs are also thought to play a major role on cell behaviors such as cell proliferation, migration (adhesion/dispersion), differentiation, angiogenesis, apoptosis, and host defense. MMPs may be classified based on their functional activity. Non-limiting examples of suitable MMPs for which a sensitive site may be designed include collagenases (MMP1, MMP8, MMP13), matrilysin (MMP7, MMP26), metalloelastase (MMP12), gelatinases (MMP2, MMP9), enamelysin (MMP20), stromelysins (MMP3, MMP10, MMP11), membrane-type MMPs (MMP14, MMP15, MMP16, MMP17, MMP24, MMP25), and other (MMP19, MMP21, MMP23A, MMP23B, MMP27, MMP28). In an exemplary embodiment, the cleavable peptide comprises a MMP9 sensitive site. In another exemplary embodiment, the cleavable peptide comprises SEQ ID NO:1 (Gly-Pro-Leu-Gly-Val-Arg-Gly-Lys-Gly-Tyr-Gly-Ahx-Cys).

A peptide of the invention may be subject to various changes, substitutions, insertions, and deletions where such changes provide for certain advantages in its use. Thus, the invention encompasses any of a variety of forms of peptide derivatives that include amides, conjugates with proteins, cyclized peptides, polymerized peptides, conservatively substituted variants, analogs, fragments, peptoids, chemically modified peptides, peptide mimetics, and replacement of Adenoviral knob (See, for example, Mathis et al., *Oncogene* 2005; 24:7775-7791).

Peptides of the invention may comprise naturally occurring amino acids, synthetic amino acids, genetically encoded amino acids, non-genetically encoded amino acids, and combinations thereof. Peptides may include both L-form and D-form amino acids.

Representative non-genetically encoded amino acids may include but are not limited to 2-aminoadipic acid; 3-aminoadipic acid; β-aminopropionic acid; 2-aminobutyric acid; 4-aminobutyric acid (piperidinic acid); 6-aminocaproic acid (Ahx); 2-aminoheptanoic acid; 2-aminoisobutyric acid; 3-aminoisobutyric acid; 2-aminopimelic acid; 2,4-diaminobutyric acid; desmosine; 2,2'-diaminopimelic acid; 2,3-diaminopropionic acid; N-ethylglycine; N-ethylasparagine; hydroxylysine; allo-hydroxylysine; 3-hydroxyproline; 4-hydroxyproline; isodesmosine; allo-isoleucine; N-methylglycine (sarcosine); N-methylisoleucine; N-methylvaline; norvaline; norleucine; and ornithine.

Representative derivatized amino acids may include for example, those molecules in which free amino groups have been derivatized to form amine hydrochlorides, p-toluene sulfonyl groups, carbobenzoxy groups, t-butyloxycarbonyl groups, chloroacetyl groups or formyl groups. Free carboxyl groups can be derivatized to form salts, methyl and ethyl esters or other types of esters or hydrazides. Free hydroxyl groups can be derivatized to form O-acyl or O-alkyl derivatives. The imidazole nitrogen of histidine can be derivatized to form N-im-benzylhistidine.

The term "conservatively substituted variant" refers to a peptide comprising an amino acid residue sequence similar to a sequence of a reference peptide in which one or more residues have been conservatively substituted with a functionally similar residue and which displays the activity as described herein. The phrase "conservatively substituted variant" also includes peptides wherein a residue is replaced with a chemically derivatized residue, provided that the resulting peptide displays activity as disclosed herein.

Examples of conservative substitutions include the substitution of one non-polar (hydrophobic) residue such as isoleucine, valine, leucine or methionine for another; the substitution of one polar (hydrophilic) residue for another such as between arginine and lysine, between glutamine and asparagine, between glycine and serine; the substitution of one basic residue such as lysine, arginine or histidine for another; or the substitution of one acidic residue, such as aspartic acid or glutamic acid for another.

Peptides of the present invention also include peptides comprising one or more additions and/or deletions or residues relative to the sequence of a peptide whose sequence is disclosed herein, so long as the requisite activity of the peptide is maintained. The term "fragment" refers to a peptide comprising an amino acid residue sequence shorter than that of a peptide disclosed herein.

In addition, a peptide can be modified by terminal-$NH_2$ acylation (e.g., acetylation, or thioglycolic acid amidation) or by terminal-carboxylamidation (e.g., with ammonia, methylamine, and the like terminal modifications). Terminal modifications are useful, as is well known, to reduce susceptibility by proteinase digestion, and therefore serve to prolong half life of the peptides in solutions, particularly biological fluids where proteases can be present. In a specific embodiment, a peptide comprises a terminal-$NH_2$ acylation. In certain embodiment, the terminal-$NH_2$ acylation is acetylation.

The term "peptoid" as used herein refers to a peptide wherein one or more of the peptide bonds are replaced by pseudopeptide bonds including but not limited to a carba bond ($CH_2$—$CH_2$), a depsi bond (CO—O), a hydroxyethylene bond (CHOH—$CH_2$), a ketomethylene bond (CO—$CH_2$), a methylene-oxy bond ($CH_2$—O), a reduced bond ($CH_2$—NH), a thiomethylene bond ($CH_2$—S), a thiopeptide bond (CS—NH), and an N-modified bond (—NRCO—). See e.g. Corringer et al. (1993) J Med Chem 36:166-172; Garbay-Jauregiuberry et al. (1992) Int J Pept Protein Res 39:523-527; Tung et al. (1992) Pept Res 5:115-118; Urge et al. (1992) Carbohydr Res 235:83-93; Pavone et al. (1993) Int J Pept Protein Res 41:15-20.

Peptides of the present invention, including peptoids, may be synthesized by any of the techniques that are known to those skilled in the art of peptide synthesis. Synthetic chemistry techniques, such as a solid-phase Merrifield-type synthesis, may be preferred for reasons of purity, antigenic specificity, freedom from undesired side products, ease of production and the like. A summary of representative techniques can be found in Stewart & Young (1969) Solid Phase Peptide Synthesis. Freeman, San Francisco; Merrifield (1969) Adv Enzymol Relat Areas Mol Biol 32:221-296; Fields & Noble (1990) Int J Pept Protein Res 35:161-214; and Bodanszky (1993) Principles of Peptide Synthesis. 2nd rev. ed. Springer-Verlag, Berlin; New York. Solid phase synthesis techniques can be found in Andersson et al. (2000) Biopolymers 55:227-250, references cited therein, and in U.S. Pat. Nos. 6,015,561, 6,015,881, 6,031,071, and 4,244, 946. Peptide synthesis in solution is described by Schröder & Lübke (1965) The Peptides. Academic Press, New York. Appropriate protective groups usable in such synthesis are described in the above texts and in McOmie (1973) Protective Groups in Organic Chemistry. Plenum Press, London, New York. Peptides that include naturally occurring amino acids can also be produced using recombinant DNA technology. In addition, peptides comprising a specified amino acid sequence can be purchased from commercial sources (e.g., Biopeptide Co., LLC of San Diego, Calif. and PeptidoGenics of Livermore, Calif.).

Any peptide or peptide mimetic of the present invention may be used in the form of a pharmaceutically acceptable salt. Suitable acids which are capable of forming a pharmaceutically acceptable salt with the peptides of the present invention include inorganic acids such as trifluoroacetic acid (TFA), hydrochloric acid (HCl), hydrobromic acid, perchloric acid, nitric acid, thiocyanic acid, sulfuric acid, phosphoric acetic acid, propionic acid, glycolic acid, lactic acid, pyruvic acid, oxalic acid, malonic acid, succinic acid, maleic acid, fumaric acid, anthranilic acid, cinnamic acid, naphthalene sulfonic acid, sulfanilic acid or the like.

Suitable bases capable of forming salts with the peptides of the present invention include inorganic bases such as sodium hydroxide, ammonium hydroxide, potassium hydroxide and the like; and organic bases such as mono-di- and tri-alkyl and aryl amines (e.g. triethylamine, diisopropyl amine, methyl amine, dimethyl amine and the like), and optionally substituted ethanolamines (e.g. ethanolamine, diethanolamine and the like).

(i) Chelating Agent

A cleavable peptide of the invention may be coupled to a chelating agent. The chelating agent may be directly coupled to the peptide or may be coupled to a linker that is coupled to the peptide. As used herein, a "chelating agent" is a molecule that forms multiple chemical bonds with a single metal atom. Prior to forming the bonds, the chelating agent has more than one pair of unshared electrons. The bonds are formed by sharing pairs of electrons with the metal atom.

Examples of chelating agents include, but are not limited to, iminodicarboxylic and polyaminopolycarboxylic reactive groups, diethylenetriaminepentaacetic acid (DTPA), 1,4,7,10-tetraazacyclododecane-1,4,7,10-tetraacetic acid (DOTA), tetramethyl heptanedionate (TMHD), 2,4-pentanedione, ethylenediamine-tetraacetic acid disodium salt (EDTA), ethyleneglycol-O,O'-bis(2-aminoethyl)-N,N,N',N'-tetraacetic acid (EGTA), N-(2-hydroxyethyl)ethylenediamine-N,N',N'-triacetic acid trisodium salt (HEDTA), nitrilotriacetic acid (NTA), and 1,4,8,11-tetraazacyclotetradecane-N,N',N",N"'-tetraacetic acid (TETA), deferoxamine (DFO), and derivatives thereof. In a specific embodiment, the chelating agent is diethylenetriaminepentaacetic acid (DTPA). In another specific embodiment, the chelating agent is 1,4,7,10-tetraazacyclododecane-1,4,7,10-tetraacetic acid (DOTA).

Chelating agents may be attached to a cleavable peptide of the invention, using the methods generally described in Liu et al., *Bioconjugate Chew.* 12(4):653, 2001; Alter et al., U.S. Pat. No. 5,753,627; and PCT Publication No. WO 91/01144; each of which is hereby incorporated by reference. A cleavable peptide of the invention may be coupled to a chelating agent by reacting the free carboxyl group of the C-terminal residue of the peptide with an appropriate functional group of the chelator. For example, a peptide may be coupled to the chelator 1,4,7,10-tetraazacyclododecane-1,4,7,10-tetraacetic acid (DOTA), common in the art of coordination chemistry. Alternatively, a cleavable peptide of the invention may be coupled to a chelating agent by reacting the free amino group of the N-terminal residue of the peptide with an appropriate functional group of the chelator, such as a carboxyl group or activated ester. For example, a peptide may be coupled to the chelator diethylenetriaminepentaacetic acid (DTPA), common in the art of coordination chemistry, when functionalized with a carboxyl substituent on the ethylene chain. Synthesis of EDTA derivatives of this type are reported in Arya et al., (*Bioconjugate Chemistry.* 2:323, 1991), wherein the four coordinating carboxyl groups are each blocked with a t-butyl group while the carboxyl substituent on the ethylene chain is free to react with the amino group of the peptide thereby forming a conjugate.

A cleavable peptide of the invention may be coupled to a metal chelator component that is peptidic, i.e., compatible with solid-phase peptide synthesis. In this case, the chelator may be coupled to the cleavable peptide of the invention in the same manner as DTPA or DOTA described above or more conveniently the chelator and agent are synthesized in tato starting from the C-terminal or N-terminal residue of the peptide and ending with the N-terminal or C-terminal residue of the chelator.

A cleavable peptide of the invention may be complexed, through its attached chelating agent, to a radionuclide, thereby resulting in a peptide that is indirectly labeled. A radionuclide is described in more detail below.

(ii) Radionuclide

A cleavable peptide of the invention may further comprise at least one radionuclide. In certain embodiments, a cleavable peptide comprises one radionuclide. In other embodiments, a cleavable peptide comprises two radionuclides. In still other embodiments, a cleavable peptide may comprise more than two radionuclides.

In the embodiment where the cleavable peptide comprises two radionuclides, spectrally distinct radionuclides are conjugated on either side of the site susceptible to cleavage by an enzyme. A radionuclide may be conjugated to the cleavable peptide via tyrosine residue, a chelating agent, and/or a Lys-Gly-Cys group. In an embodiment, one radionuclide may be conjugated to the peptide via a tyrosine residue and one radionuclide may be complexed to the peptide via a chelating agent. In another embodiment, one radionuclide may be conjugated to the peptide via a tyrosine residue and one radionuclide may be conjugated to the peptide via a Lys-Gly-Cys group. In still another embodiment, one radionuclide may be conjugated to the radionuclide via a chelating agent and another radionuclide may be conjugated to the peptide via a Lys-Gly-Cys group. The cleavable peptide comprising two radionuclides may be further conjugated to a particle. A particle is described in more detail in Section I(b) below.

In the embodiment where a cleavable peptide comprises one radionuclide, the cleavable peptide may be further conjugated to a particle comprising a spectrally distinct radionuclide. A particle comprising a radionuclide is described in more detail in Section I(b) below. In the foregoing embodiment, cleavage of the peptide releases the radionuclide from the particle. A radionuclide may be conjugated to the cleavable peptide via tyrosine residue, a chelating agent, or a Lys-Gly-Cys group. In an embodiment, the radionuclide may be complexed to the peptide via a chelating agent. In another embodiment, the radionuclide may be conjugated to the peptide via a tyrosine residue. In still another embodiment, radionuclide may be conjugated to the peptide via a Lys-Gly-Cys group. In a specific embodiment, a cleavable peptide is conjugated to a particle via a cysteine residue. In another specific embodiment, a cleavable peptide is conjugated to a particle via a polyethylene glycol that is conjugated to the particle.

A radionuclide may be a γ-emitting radionuclide, Auger-emitting radionuclide, β-emitting radionuclide, an α-emitting radionuclide, or a positron-emitting radionuclide. A radionuclide may also be a therapeutic agent. A radionuclide employed in the present invention may be a radionuclide that decays via $\beta^+$ decay such as $^{10}C$, $^{11}C$, $^{13}O$, $^{14}O$, $^{15}O$, $^{12}N$, $^{13}N$, $^{15}F$, $^{18}F$, $^{18}F$-FDG, $^{32}Cl$, $^{33}Cl$, $^{34}Cl$, $^{43}Sc$, $^{44}Sc$, $^{45}Ti$, $^{51}Mn$, $^{52}Mn$, $^{52}Fe$, $^{53}Fe$, $^{55}Co$, $^{56}Co$, $^{58}Co$, $^{61}Cu$, $^{62}Cu$, $^{62}Zn$, $^{63}Zn$, $^{64}Cu$, $^{65}Zn$, $^{66}Ga$, $^{66}Ge$, $^{67}Ge$, $^{68}Ga$, $^{69}Ge$, $^{69}As$, $^{70}As$, $^{70}Se$, $^{71}As$, $^{73}Se$, $^{74}Kr$, $^{74}Br$, $^{75}Br$, $^{76}Br$, $^{77}Br$, $^{77}Kr$, $^{78}Br$, $^{78}Rb$, $^{79}Rb$, $^{79}Kr$, $^{81}Rb$, $^{82}Rb$, $^{84}Rb$, $^{84}Zr$, $^{85}Y$, $^{86}Y$, $^{87}Y$, $^{87}Zr$, $^{88}Y$, $^{89}Zr$, $^{92}Tc$, $^{93}TC$, $^{94}TC$, $^{95}TC$, $^{95}RU$, $^{95}Rh$, $^{96}Rh$, $^{97}Rh$, $^{98}Rh$, $^{99}Rh$, $^{100}Rh$, $^{101}Ag$, $^{102}Ag$, $^{102}Rh$, $^{103}Ag$, $^{104}Ag$, $^{105}Ag$, $^{106}Ag$, $^{108}In$, $^{109}In$, $^{110}In$, $^{115}Sb$, $^{116}Sb$, $^{117}Sb$, $^{115}Te$, $^{116}Te$, $^{117}Te$, $^{117}I$, $^{118}I$, $^{118}Xe$, $^{119}Xe$, $^{119}I$, $^{119}Te$, $^{120}I$, $^{120}Xe$, $^{121}Xe$, $^{121}I$, $^{122}I$, $^{123}Xe$, $^{124}I$, $^{126}I$, $^{128}I$, $^{129}La$, $^{130}La$, $^{131}La$, $^{132}La$, $^{133}La$, $^{135}La$, $^{136}La$, $^{140}Sm$, $^{141}Sm$, $^{142}Sm$, $^{144}Gd$, $^{145}Gd$, $^{145}Eu$, $^{146}Gd$, $^{146}Eu$, $^{147}Eu$, $^{147}Gd$, $^{148}Eu$, $^{150}Eu$, $^{190}Au$, $^{191}Au$, $^{192}Au$, $^{193}Au$, $^{198}Au$, $^{199}Au$, $^{193}Tl$, $^{194}Tl$, $^{194}Au$, $^{195}Tl$, $^{198}Tl$, $^{197}Tl$, $^{198}Tl$, $^{200}Tl$, $^{200}Bi$, $^{202}Bi$, $^{203}Bi$, $^{205}Bi$ or $^{206}Bi$, a radionuclide that decays via $\beta^-$ decay such as $^{3}H$, $^{14}C$, $^{35}S$, $^{32}P$, $^{131}I$, $^{59}Fe$, $^{60}Co$, $^{67}Cu$, $^{89}Sr$, $^{90}Sr$, $^{90}Y$, $^{99}Mo$, $^{133}Xe$, $^{137}Cs$, $^{153}Sm$, $^{177}Lu$ or $^{188}Re$, or a radionuclide that decays via electron capture such as $^{111}In$, $^{123}I$, $^{125}I$, $^{201}Tl$, $^{67}Ga$, $^{51}Cr$, $^{57}Co$, $^{58}Co$, $^{62}Zn$, or $^{82}Sr$. Most specifically, it may be $^{18}F$, $^{11}C$, $^{13}N$, $^{15}O$, $^{60}Cu$, $^{64}Cu$, $^{67}Cu$, $^{124}I$, $^{68}Ga$, $^{52}Fe$, $^{58}Co$, $^{3}H$, $^{14}C$, $^{35}S$, $^{32}P$, $^{131}I$, $^{59}Fe$, $^{60}Co$, $^{89}Sr$, $^{90}Sr$, $^{90}Y$, $^{99}Mo$, $^{133}Xe$, $^{137}Cs$, $^{153}Sm$, $^{177}Lu$, $^{186}Re$, $^{123}I$, $^{125}I$, $^{201}Ti$ or $^{67}Ga$, but is not limited thereto. Since other radionuclides that do not decay via $\beta^+$, $\beta^-$ or electron capture can also emit light, they may also be used as the radionuclide of the present disclosure. In certain embodiments, a radionuclide may be selected from the group consisting of $^{111}In$, $^{125}I$, $^{64}Cu$, $^{198}Au$, $^{199}Au$, $^{99m}Tc$, and $^{123}I$. In a specific embodiment, a radionuclide may be selected from the group consisting of $^{111}In$, $^{125}I$, $^{64}Cu$, $^{198}Au$, and $^{199}Au$.

A first radionuclide and a second radionuclide are incorporated into a composition as described above provided they are spectrally distinct. By spectrally distinct is meant that they can be spectrally differentiated upon imaging. In a specific embodiment, gamma rays of the first and second radionuclide have minimal overlapping signal in the acceptance energy window for SPECT imaging. However, this is not always possible, thus use of radionuclides with an overlapping signal may be used. In such an embodiment, the overlap is removed in a quantifiable and reproducible manner. For example, this may be done via methods described in Example 6 and the Methods for Examples 4-10. In a specific embodiment, a first radionuclide is $^{125}I$ and a second radionuclide is $^{64}Cu$ or $^{111}In$. In another specific embodiment, a first radionuclide is $^{199}Au$ and a second radionuclide is $^{111}In$. In still another specific embodiment, a first radionuclide is $^{25}I$ and a second radionuclide is $^{99m}Tc$.

As described above, a radionuclide may be conjugated directly to a peptide without the use of a chelating agent. For example, a radioactive iodine label (e.g., $^{122}I$, $^{123}I$, $^{124}I$, $^{125}I$, or $^{131}I$) is capable of being conjugated to each D- or L-Tyr or D- or L-4-amino-Phe residue present in a peptide of the invention. In an embodiment, a tyrosine residue of a peptide of the invention may be halogenated. Halogens include fluorine, chlorine, bromine, iodine, and astatine. Such halogenated peptides of the invention may be detectably labeled if the halogen is a radioisotope, such as, for example, $^{18}F$, $^{75}Br$, $^{77}Br$, $^{122}I$, $^{123}I$, $^{124}I$, $^{125}I$, $^{129}I$, $^{131}I$, or $^{211}At$. Halogenated peptides of the invention contain a halogen covalently bound to at least one amino acid, and preferably to D-Tyr residues present in the peptide. Alternatively, $^{99m}Tc$ label is capable of being conjugated to a -Lys-Gly-Cys- group. As such, a peptide of the invention may comprise a -Lys-Gly-Cys- group for $^{99m}Tc$ labeling.

(iii) Polyethylene Glycol

A cleavable peptide of the invention may comprise polyethylene glycol (PEG). The PEG may be conjugated directly to the peptide via functional group or the PEG may be conjugated to the peptide via a linker. Any suitable linker to conjugate PEG to a peptide may be used. For example, a linker may be a peptide linker, an alkyl linker, a non-cleavable linker, or a combination thereof. In a specific embodiment, the linker may be a DBCO-maleimide linker. Any suitable PEG may be used in a peptide of the invention. PEGs are available in a range of molecular weights from 300 g/mol to 10,000,000 g/mol. A PEG suitable in a peptide of the invention may be from about 1,000 g/mol to about 20,000 g/mol. Alternatively, a PEG suitable in a peptide of the invention may be from about 1,000 g/mol to about 10,000 g/mol. In another embodiment, a PEG suitable in a peptide of the invention may be from about 5,000 g/mol to about 10,000 g/mol. In a specific embodiment, a PEG suitable in a peptide of the invention may be 5,000 g/mol.

(iv) Specific Embodiments

In a specific embodiment, a peptide comprises a caspase-3 sensitive site, a tyrosine for radiolabeling and a -Lys-Gly-Cys- group for radiolabeling. In another specific embodiment, a peptide comprises a caspase-3 sensitive site, a tyrosine for conjugation to $^{125}$I and a -Lys-Gly-Cys- group for conjugation to $^{99m}$Tc. In still another specific embodiment, a peptide comprises SEQ ID NO:2 (Asp-Glu-Val-Asp), a tyrosine for radiolabeling and a -Lys-Gly-Cys- group for radiolabeling. In yet still another specific embodiment, a peptide comprises SEQ ID NO:5 (Ahx-Tyr-Ahx-Asp-Glu-Val-Asp-Gly-Lys-Gly-Cys). In certain embodiments, the peptide comprises a terminal-NH$_2$ acylation. Specifically, the terminal-NH$_2$ acylation is acetylation.

In a different specific embodiment, a peptide comprises a caspase-3 sensitive site, a tyrosine for radiolabeling and a chelating agent for radiolabeling. In another specific embodiment, a peptide comprises a caspase-3 sensitive site, a tyrosine for conjugation to $^{125}$I and a chelating agent for complexing with $^{111}$In. In still another specific embodiment, a peptide comprises SEQ ID NO:2 (Asp-Glu-Val-Asp), a tyrosine for radiolabeling and a chelating agent for radiolabeling. In yet still another specific embodiment, a peptide comprises a hydrophobic portion and a hydrophilic portion separated by a caspase-3 sensitive site, a tyrosine for radiolabeling and a chelating agent for radiolabeling. In another specific embodiment, a peptide comprises SEQ ID NO:4 (Tyr-Leu-Ala-Ile-Ahx-Pro-Ala) and SEQ ID NO:3 (Gly-Arg-Arg-Arg-Orn-Arg-Arg-Lys-Lys-Arg-Lys) separated by the caspase-3 sensitive site set forth in SEQ ID NO:2 (Asp-Glu-Val-Asp), a tyrosine for radiolabeling and a chelating agent for radiolabeling. Specifically, a peptide comprises SEQ ID NO:6 (Tyr-Leu-Ala-Ile-Ahx-Pro-Ala-Asp-Glu-Val-Asp-Gly-Arg-Arg-Arg-Orn-Arg-Arg-Lys-Lys-Arg-Lys). In certain embodiments, the peptide comprises a terminal-NH$_2$ acylation. Specifically, the terminal-NH$_2$ acylation is acetylation.

In another different specific embodiment, a peptide comprises a MMP9 sensitive site, a tyrosine for radiolabeling, a cysteine for conjugation to a nanoparticle and a chelating agent for radiolabeling. In another specific embodiment, a peptide comprises a MMP9 sensitive site, a tyrosine for conjugation to $^{125}$I, a cysteine for conjugation to a nanoparticle and a chelating agent for complexing with $^{111}$In or $^{64}$Cu. In still another specific embodiment, a peptide comprises SEQ ID NO:1 (Gly-Pro-Leu-Gly-Val-Arg-Gly-Lys-Gly-Tyr-Gly-Ahx-Cys), wherein $^{125}$I is conjugated to the tyrosine, the cysteine is conjugated to a nanoparticle and a chelating agent is conjugated to the glycine.

In yet another different specific embodiment, a peptide comprises a MMP9 sensitive site, a cysteine for conjugation to a nanoparticle and a chelating agent for radiolabeling. In another specific embodiment, a peptide comprises a MMP9 sensitive site, a cysteine for conjugation to a nanoparticle and a chelating agent for complexing with $^{111}$In. In still another specific embodiment, a peptide comprises SEQ ID NO:1 (Gly-Pro-Leu-Gly-Val-Arg-Gly-Lys-Gly-Tyr-Gly-Ahx-Cys), wherein the cysteine is conjugated to the nanoparticle and a chelating agent is conjugated to the glycine.

In yet still another different specific embodiment, a peptide comprises a MMP9 sensitive site, a PEG, and a chelating agent for radiolabeling. In another specific embodiment, a peptide comprises a MMP9 sensitive site, a PEG, and a chelating agent for complexing with $^{111}$In. In still another specific embodiment, a peptide comprises SEQ ID NO:1 (Gly-Pro-Leu-Gly-Val-Arg-Gly-Lys-Gly-Tyr-Gly-Ahx-Cys), wherein the cysteine is conjugated to a PEG and a chelating agent is conjugated to the glycine. In still yet another specific embodiment, a peptide comprises SEQ ID NO:1 (Gly-Pro-Leu-Gly-Val-Arg-Gly-Lys-Gly-Tyr-Gly-Ahx-Cys), wherein the cysteine is conjugated to a PEG, the PEG is conjugated to a nanoparticle, and a chelating agent is conjugated to the glycine.

(b) Particle

A composition of the invention further comprises a particle. As used herein the term "particle" includes nanoparticles as well as microparticles. Nanoparticles are defined as particles of less than 1.0 μm in diameter. A preparation of nanoparticles includes particles having an average particle size of less than 1.0 μm in diameter. Microparticles are particles of greater than 1.0 μm in diameter but less than 1 mm. A preparation of microparticles includes particles having an average particle size of greater than 1.0 μm in diameter. The microparticles may therefore have a diameter of at least 5, at least 10, at least 25, at least 50, or at least 75 microns, including sizes in ranges of 5-10 microns, 5-15 microns, 5-20 microns, 5-30 microns, 5-40 microns, or 5-50 microns. A composition of particles may have heterogeneous size distributions ranging from 1 nm to mm sizes. In a specific embodiment, a particle of the invention is a nanoparticle. In some embodiments the diameter is about 5 nm to about 500 nm. In other embodiments, the diameter is about 100 nm to about 200 nm. In another embodiment, the diameter is about 10 nm to about 100 nm. In still another embodiment, the diameter is about 10 nm to about 50 nm. In a specific embodiment, the diameter is about 10 nm.

The particles may be composed of a variety of materials including ceramic, metallic, natural polymer materials (including lipids, sugars, chitosan, hyaluronic acid etc), synthetic polymer materials (including poly-lactide-coglycolide, poly-glycerol sebacate, etc), and non-polymer materials, or combinations thereof.

In certain embodiments, the particles may be inorganic nanoparticles. Inorganic nanoparticles are primarily metal-based and have the potential to be synthesized with near monodispersity. Non-limiting examples of inorganic nanoparticles include iron oxide nanoparticles, nickel nanoparticles, cobalt nanoparticles, silica nanoparticles, gold nanoparticles, calcium-phosphate based nanoparticles, silver nanoparticles, platinum nanoparticles and quantum dots (e.g. CdS, CdSe, Ag$_2$S). In a specific embodiment, a nanoparticle of the invention is a gold nanoparticle.

In certain embodiments, a radionuclide may be incorporated into a nanoparticle. A radionuclide may be as described above in Section I(a)(ii). In a specific embodiment a radiometal may be incorporated into a nanoparticle. For example, $^{198}$Au, $^{199}$Au or $^{64}$Cu may be incorporated into a gold nanoparticle. In a specific embodiment, $^{199}$Au may be incorporated into a gold nanoparticle.

A cleavable peptide of the invention may be conjugated to a nanoparticle of the invention via a thiol group. In certain embodiments, the cleavable peptide may be conjugated to a nanoparticle of the invention via a cysteine residue of the peptide. In other embodiments, the cleavable peptide may be conjugated to a nanoparticle via a thiol group of polyethylene glycol. In still other embodiments, the cleavable peptide may be conjugated to a nanoparticle via a thiol group of a linker. Suitable peptides, polyethylene glycols and linkers are described above in Section I(a). In a specific embodiment, a cleavable peptide may be conjugated to a gold nanoparticle via a cysteine residue of the peptide. In certain embodiments, the cysteine residue is at the N-terminus of the peptide. In another specific embodiment, a cleavable peptide may be conjugated to a gold nanoparticle via a polyethylene glycol which is conjugated to the gold nanoparticle via a thiol group.

The particles may also be coated with one or more stabilizing substances, which may be particularly useful for long term depoting with parenteral administration or for oral delivery by allowing passage of the particles through the stomach or gut without dissolution. For example, particles intended for oral delivery may be stabilized with a coating of a substance such as mucin, a secretion containing mucopolysaccharides produced by the goblet cells of the intestine, the submaxillary glands, and other mucous glandular cells. Alternatively, polyethylene glycol (PEG) may be incorporated onto the particle surface. Any suitable PEG may incorporated onto the particle surface. PEGs are available in a range of molecular weights from 300 g/mol to 10,000,000 g/mol. A PEG incorporated onto the particle surface may be from about 1,000 g/mol to about 20,000 g/mol. Alternatively, a PEG incorporated onto the particle surface may be from about 1,000 g/mol to about 10,000 g/mol. In another embodiment, a PEG incorporated onto the particle surface may be from about 5,000 g/mol to about 10,000 g/mol. In a specific embodiment, a PEG incorporated onto the particle surface may be 5,000 g/mol.

To enhance delivery the particles may be incorporated, for instance, into liposomes, virosomes, cationic lipids or other lipid based structures. The term "cationic lipid" refers to lipids which carry a net positive charge at physiological pH. Such lipids include, but are not limited to, DODAC, DOTMA, DDAB, DOTAP, DC-Chol and DMRIE. Additionally, a number of commercial preparations of cationic lipids are available. These include, for example, LIPOFECTIN® (commercially available cationic liposomes comprising DOTMA and DOPE, from GIBCO/BRL, Grand Island, N.Y., USA); LIPOFECTAMINE® (commercially available cationic liposomes comprising DOSPA and DOPE, from GIBCO/BRL); and TRANSFECTAM® (commercially available cationic lipids comprising DOGS in ethanol from Promega Corp., Madison, Wis., USA). A variety of methods are available for preparing liposomes e.g., U.S. Pat. Nos. 4,186,183, 4,217,344, 4,235,871, 4,261,975, 4,485,054, 4,501,728, 4,774,085, 4,837,028, 4,946,787; and PCT Publication No. WO 91/17424. The particles may also be composed in whole or in part of GRAS components. i.e., ingredients are those that are Generally Regarded As Safe (GRAS) by the US FDA. GRAS components useful as particle material include non-degradable food based particles such as cellulose.

In certain embodiments, the particle may further comprise a therapeutic agent. Thus, the compositions of the invention can achieve two purposes at the same time, the diagnostic methods and delivery of a therapeutic agent. Any therapeutic agent can be incorporated within the particles, which can locally or systemically deliver or maintain the incorporated agents following administration or application to a subject. A therapeutic agent can be incorporated into the particles using technology known to those skilled in the art. A particle may comprise one, two, three, four, or five therapeutic agents. Therapeutic agents include but are not limited to drugs, therapeutic compounds, genetic materials, metals (such as radioactive isotopes), proteins, peptides, carbohydrates, lipids, steroids, nucleic acid based materials, or derivatives, analogues, or combinations thereof in their native form or derivatized with hydrophobic or charged moieties to enhance incorporation or adsorption into a cell. Such therapeutic agents may be water soluble or may be hydrophobic. Non-limiting examples of therapeutic agents may include immune-related agents, thyroid agents, respiratory products, antineoplastic agents, anti-helmintics, anti-malarials, mitotic inhibitors, hormones, anti-protozoans, anti-tuberculars, cardiovascular products, blood products, biological response modifiers, anti-fungal agents, vitamins, peptides, anti-allergic agents, anti-coagulation agents, circulatory drugs, metabolic potentiators, anti-virals, anti-anginals, antibiotics, anti-inflammatories, anti-rheumatics, narcotics, cardiac glycosides, neuromuscular blockers, sedatives, local anesthetics, general anesthetics, or radioactive atoms or ions. Non-limiting examples of therapeutic agents are described below.

In a specific embodiment, a therapeutic agent is any compound known in the art that is used in the detection, diagnosis, or treatment of cancer. Such compounds may be naturally-occurring, modified, or synthetic. The therapeutic agent preferably reduces or interferes with tumor growth or otherwise reduces the effect of the tumor within the body or organism. A therapeutic agent that reduces the symptoms produced by the tumor or reduces tumor growth is suitable for the present invention. Additionally, any therapeutic agent that reduces the symptoms associated with tumor cell growth will work for purposes of the present invention.

A therapeutic agent of the invention may be a small molecule therapeutic, a therapeutic nucleic acid, or a chemotherapeutic agent. A representative therapeutic nucleic acid may encode a polypeptide having an ability to induce an immune response and/or an anti-angiogenic response in vivo. Representative therapeutic proteins with immunostimulatory effects include but are not limited to cytokines (e.g., an interleukin (IL) such as IL2, IL4, IL7, IL12, interferons, granulocyte-macrophage colony-stimulating factor (GM-CSF), tumor necrosis factor alpha (TNF-α)), immunomodulatory cell surface proteins (e.g., human leukocyte antigen (HLA proteins), co-stimulatory molecules, and tumor-associated antigens. See Kirk & Mule, 2000; Mackensen et al., 1997; Walther & Stein, 1999; and references cited therein. Representative proteins with anti-angiogenic activities that can be used in accordance with the presently disclosed subject matter include: thrombospondin I (Kosfeld & Frazier, 1993; Tolsma et al., 1993; Dameron et al., 1994), metallospondin proteins (Carpizo & Iruela-Arispe, 2000), class I interferons (Albini et al., 2000), IL12 (Voest et al., 1995), protamine (Ingber et al., 1990), angiostatin (O'Reilly et al., 1994), laminin (Sakamoto et al., 1991), endostatin (O'Reilly et al., 1997), and a prolactin fragment (Clapp et al., 1993). In addition, several anti-angiogenic peptides have been isolated from these proteins (Maione et al., 1990; Eijan et al., 1991; Woltering et al., 1991). Representative proteins with both immunostimulatory and anti-angiogenic activities may include IL12, interferon-γ, or a chemokine. Other therapeutic nucleic acids that may be useful for cancer therapy include but are not limited to nucleic acid sequences encoding tumor suppressor gene products/antigens, antimetabolites, suicide gene products, and combinations thereof.

A chemotherapeutic agent refers to a chemical compound that is useful in the treatment of cancer. The compound may be a cytotoxic agent that affects rapidly dividing cells in general, or it may be a targeted therapeutic agent that affects the deregulated proteins of cancer cells. A cytotoxic agent is any naturally-occurring, modified, or synthetic compound that is toxic to tumor cells. Such agents are useful in the treatment of neoplasms, and in the treatment of other symptoms or diseases characterized by cell proliferation or a hyperactive cell population. The chemotherapeutic agent may be an alkylating agent, an anti-metabolite, an anti-tumor antibiotic, an anti-cytoskeletal agent, a topoisomerase inhibitor, an anti-hormonal agent, a targeted therapeutic agent, a photodynamic therapeutic agent, or a combination thereof. In an exemplary embodiment, the chemotherapeutic agent is selected from the group consisting of liposomal doxorubicin and nanoparticle albumin docetaxel.

Non-limiting examples of suitable alkylating agents may include altretamine, benzodopa, busulfan, carboplatin, carboquone, carmustine (BCNU), chlorambucil, chlornaphazine, cholophosphamide, chlorozotocin, cisplatin, cyclosphosphamide, dacarbazine (DTIC), estramustine, fotemustine, ifosfamide, improsulfan, lipoplatin, lomustine (CCNU), mafosfamide, mannosulfan, mechlorethamine, mechlorethamine oxide hydrochloride, melphalan, meturedopa, mustine (mechlorethamine), mitobronitol, nimustine, novembichin, oxaliplatin, phenesterine, piposulfan, prednimustine, ranimustine, satraplatin, semustine, temozolomide, thiotepa, treosulfan, triaziquone, triethylenemelamine, triethylenephosphoramide (TEPA), triethylenethiophosphaoramide (thiotepa), trimethylolomelamine, trofosfamide, uracil mustard and uredopa.

Suitable anti-metabolites may include, but are not limited to aminopterin, ancitabine, azacitidine, 8-azaguanine, 6-azauridine, capecitabine, carmofur (1-hexylcarbomoyl-5-fluorouracil), cladribine, clofarabine, cytarabine (cytosine arabinoside (Ara-C)), decitabine, denopterin, dideoxyuridine, doxifluridine, enocitabine, floxuridine, fludarabine, 5-fluorouracil, gemcetabine, hydroxyurea (hydroxycarbamide), leucovorin (folinic acid), 6-mercaptopurine, methotrexate, nafoxidine, nelarabine, oblimersen, pemetrexed, pteropterin, raltitrexed, tegofur, tiazofurin, thiamiprine, tioguanine (thioguanine), and trimetrexate.

Non-limiting examples of suitable anti-tumor antibiotics may include aclacinomysin, aclarubicin, actinomycins, adriamycin, aurostatin (for example, monomethyl auristatin E), authramycin, azaserine, bleomycins, cactinomycin, calicheamicin, carabicin, caminomycin, carzinophilin, chromomycins, dactinomycin, daunorubicin, detorubicin, 6-diazo-5-oxo-L-norleucine, doxorubicin, epirubicin, epoxomicin, esorubicin, idarubicin, marcellomycin, mitomycins, mithramycin, mycophenolic acid, nogalamycin, olivomycins, peplomycin, plicamycin, potfiromycin, puromycin, quelamycin, rodorubicin, sparsomycin, streptonigrin, streptozocin, tubercidin, valrubicin, ubenimex, zinostatin, and zorubicin.

Non-limiting examples of suitable anti-cytoskeletal agents may include cabazitaxel, colchicines, demecolcine, docetaxel, epothilones, ixabepilone, macromycin, omacetaxine mepesuccinate, ortataxel, paclitaxel (for example, DHA-paclitaxel), taxane, tesetaxel, vinblastine, vincristine, vindesine, and vinorelbine.

Suitable topoisomerase inhibitors may include, but are not limited to, amsacrine, etoposide (VP-16), irinotecan, mitoxantrone, RFS 2000, teniposide, and topotecan.

Non-limiting examples of suitable anti-hormonal agents may include aminoglutethimide, antiestrogen, aromatase inhibiting 4(5)-imidazoles, bicalutamide, finasteride, flutamide, fluvestrant, goserelin, 4-hydroxytamoxifen, keoxifene, leuprolide, LY117018, mitotane, nilutamide, onapristone, raloxifene, tamoxifen, toremifene, and trilostane.

Examples of targeted therapeutic agents may include, without limit, monoclonal antibodies such as alemtuzumab, cartumaxomab, edrecolomab, epratuzumab, gemtuzumab, gemtuzumab ozogamicin, glembatumumab vedotin, ibritumomab tiuxetan, reditux, rituximab, tositumomab, and trastuzumab; protein kinase inhibitors such as bevacizumab, cetuximab, crizonib, dasatinib, erlotinib, gefitinib, imatinib, lapatinib, mubritinib, nilotinib, panitumumab, pazopanib, sorafenib, sunitinib, toceranib, and vandetanib.

Non limiting examples of angiogeneisis inhibitors may include angiostatin, bevacizumab, denileukin diftitox, endostatin, everolimus, genistein, interferon alpha, interleukin-2, interleukin-12, pazopanib, pegaptanib, ranibizumab, rapamycin (sirolimus), temsirolimus, and thalidomide.

Non limiting examples of growth inhibitory polypeptides may include bortazomib, erythropoietin, interleukins (e.g., IL-1, IL-2, IL-3, IL-6), leukemia inhibitory factor, interferons, romidepsin, thrombopoietin, TNF-α, CD30 ligand, 4-1BB ligand, and Apo-1 ligand.

Non-limiting examples of photodynamic therapeutic agents may include aminolevulinic acid, methyl aminolevulinate, retinoids (alitretinon, tamibarotene, tretinoin), and temoporfin.

Other antineoplastic agents may include anagrelide, arsenic trioxide, asparaginase, bexarotene, bropirimine, celecoxib, chemically linked Fab, efaproxiral, etoglucid, ferruginol, lonidamide, masoprocol, miltefosine, mitoguazone, talapanel, trabectedin, and vorinostat.

Also included are pharmaceutically acceptable salts, acids, or derivatives of any of the above listed agents. The dose of the chemotherapeutic agent can and will vary depending upon the agent and the type of tumor or neoplasm. A skilled practitioner will be able to determine the appropriate dose of the chemotherapeutic agent.

Other therapeutic agents may comprise a virus or a viral genome such as an oncolytic virus. An oncolytic virus comprises a naturally occurring virus that is capable of killing a cell in the target tissue (for example, by lysis) when it enters such a cell.

In other embodiments, a particle may further comprise a targeting agent. A targeting agent may promote targeting of the particle to a desire site. For example, a particle may be coated with a targeting agent. A targeting agent can have an affinity for a cell, a tissue, a protein, DNA, RNA, an antibody, an antigen, a compound, and the like, that may be associated with a condition, disease, or related biological event, of interest. In a specific embodiment, the targeting agent has affinity for a tumor. In particular, the targeting agent can function to target specific DNA, RNA, and/or proteins of interest. In an embodiment, the targeting agent can include, but is not limited to, polypeptides (e.g., proteins such as, but not limited to, cell surface receptors and antibodies (monoclonal or polyclonal)), antigens, nucleic acids (both monomeric and oligomeric), polysaccharides, sugars, fatty acids, steroids, purines, pyrimidines, ligands, aptamers, small molecules, albumin, or combinations thereof, that have an affinity for a condition, disease, or related biological event or other chemical, biochemical, and/or biological events of the condition, disease, or biological event. In an embodiment, the targeting agent can include: aptamers, sequence-specific DNA oligonucleotides, locked nucleic acids (LNA), and peptide nucleic acids (PNA), antibodies, and small molecule protein receptors. For example, when liver targeting is desired, a composition may comprise galactose-containing copolymers which are recognized by hepatocytes. Or, for example, when tumor targeting is desired, a targeting agent may be transferrin which binds to transferrin receptors which are highly overexpressed on tumors. One of skill in the art will appreciate that various targeting agents may enable targeting of a particle to specific tissue. For example, a particle may be conjugated to antibodies in order to provide specific delivery of the particle to the site of a tumor.

(c) Pharmaceutical Composition

The present disclosure also provides pharmaceutical compositions. The pharmaceutical composition comprises a composition of the invention, as an active ingredient, and at least one pharmaceutically acceptable excipient.

The pharmaceutically acceptable excipient may be a diluent, a binder, a filler, a buffering agent, a pH modifying agent, a disintegrant, a dispersant, a preservative, a lubricant, taste-masking agent, a flavoring agent, or a coloring agent. The amount and types of excipients utilized to form pharmaceutical compositions may be selected according to known principles of pharmaceutical science.

In one embodiment, the excipient may be a diluent. The diluent may be compressible (i.e., plastically deformable) or abrasively brittle. Non-limiting examples of suitable compressible diluents include microcrystalline cellulose (MCC), cellulose derivatives, cellulose powder, cellulose esters (i.e., acetate and butyrate mixed esters), ethyl cellulose, methyl cellulose, hydroxypropyl cellulose, hydroxypropyl methylcellulose, sodium carboxymethylcellulose, corn starch, phosphated corn starch, pregelatinized corn starch, rice starch, potato starch, tapioca starch, starch-lactose, starch-calcium carbonate, sodium starch glycolate, glucose, fructose, lactose, lactose monohydrate, sucrose, xylose, lactitol, mannitol, malitol, sorbitol, xylitol, maltodextrin, and trehalose. Non-limiting examples of suitable abrasively brittle diluents include dibasic calcium phosphate (anhydrous or dihydrate), calcium phosphate tribasic, calcium carbonate, and magnesium carbonate.

In another embodiment, the excipient may be a binder. Suitable binders include, but are not limited to, starches, pregelatinized starches, gelatin, polyvinylpyrrolidone, cellulose, methylcellulose, sodium carboxymethylcellulose, ethylcellulose, polyacrylamides, polyvinyloxoazolidone, polyvinylalcohols, $C_{12}$-$C_{18}$ fatty acid alcohol, polyethylene glycol, polyols, saccharides, oligosaccharides, polypeptides, oligopeptides, and combinations thereof.

In another embodiment, the excipient may be a filler. Suitable fillers include, but are not limited to, carbohydrates, inorganic compounds, and polyvinylpyrrolidone. By way of non-limiting example, the filler may be calcium sulfate, both di- and tri-basic, starch, calcium carbonate, magnesium carbonate, microcrystalline cellulose, dibasic calcium phosphate, magnesium carbonate, magnesium oxide, calcium silicate, talc, modified starches, lactose, sucrose, mannitol, or sorbitol.

In still another embodiment, the excipient may be a buffering agent. Representative examples of suitable buffering agents include, but are not limited to, phosphates, carbonates, citrates, tris buffers, and buffered saline salts (e.g., Tris buffered saline or phosphate buffered saline).

In various embodiments, the excipient may be a pH modifier. By way of non-limiting example, the pH modifying agent may be sodium carbonate, sodium bicarbonate, sodium citrate, citric acid, or phosphoric acid.

In a further embodiment, the excipient may be a disintegrant. The disintegrant may be non-effervescent or effervescent. Suitable examples of non-effervescent disintegrants include, but are not limited to, starches such as corn starch, potato starch, pregelatinized and modified starches thereof, sweeteners, clays, such as bentonite, micro-crystalline cellulose, alginates, sodium starch glycolate, gums such as agar, guar, locust bean, karaya, pecitin, and tragacanth. Non-limiting examples of suitable effervescent disintegrants include sodium bicarbonate in combination with citric acid and sodium bicarbonate in combination with tartaric acid.

In yet another embodiment, the excipient may be a dispersant or dispersing enhancing agent. Suitable dispersants may include, but are not limited to, starch, alginic acid, polyvinylpyrrolidones, guar gum, kaolin, bentonite, purified wood cellulose, sodium starch glycolate, isoamorphous silicate, and microcrystalline cellulose.

In another alternate embodiment, the excipient may be a preservative. Non-limiting examples of suitable preservatives include antioxidants, such as BHA, BHT, vitamin A, vitamin C, vitamin E, or retinyl palmitate, citric acid, sodium citrate; chelators such as EDTA or EGTA; and antimicrobials, such as parabens, chlorobutanol, or phenol.

In a further embodiment, the excipient may be a lubricant. Non-limiting examples of suitable lubricants include minerals such as talc or silica; and fats such as vegetable stearin, magnesium stearate or stearic acid.

In yet another embodiment, the excipient may be a taste-masking agent. Taste-masking materials include cellulose ethers; polyethylene glycols; polyvinyl alcohol; polyvinyl alcohol and polyethylene glycol copolymers; monoglycerides or triglycerides; acrylic polymers; mixtures of acrylic polymers with cellulose ethers; cellulose acetate phthalate; and combinations thereof.

In an alternate embodiment, the excipient may be a flavoring agent. Flavoring agents may be chosen from synthetic flavor oils and flavoring aromatics and/or natural oils, extracts from plants, leaves, flowers, fruits, and combinations thereof.

In still a further embodiment, the excipient may be a coloring agent. Suitable color additives include, but are not limited to, food, drug and cosmetic colors (FD&C), drug and cosmetic colors (D&C), or external drug and cosmetic colors (Ext. D&C).

The weight fraction of the excipient or combination of excipients in the composition may be about 99% or less, about 97% or less, about 95% or less, about 90% or less, about 85% or less, about 80% or less, about 75% or less, about 70% or less, about 65% or less, about 60% or less, about 55% or less, about 50% or less, about 45% or less, about 40% or less, about 35% or less, about 30% or less, about 25% or less, about 20% or less, about 15% or less, about 10% or less, about 5% or less, about 2%, or about 1% or less of the total weight of the composition.

The composition can be formulated into various dosage forms and administered by a number of different means that will deliver a therapeutically effective amount of the active ingredient. Such compositions can be administered enterally (oral, gastric, rectal administration) parenterally, or intratumorally in dosage unit formulations containing conventional nontoxic pharmaceutically acceptable carriers, adjuvants, and vehicles as desired. The term parenteral as used herein includes subcutaneous, intravenous, intramuscular, intra-articular, or intrasternal injection, or infusion techniques. Formulation of drugs is discussed in, for example, Gennaro, A. R., Remington's Pharmaceutical Sciences, Mack Publishing Co., Easton, Pa. (18th ed, 1995), and Liberman, H. A. and Lachman, L., Eds., Pharmaceutical Dosage Forms, Marcel Dekker Inc., New York, N.Y. (1980). In a specific embodiment, a composition may be an intravenous or intratracheal composition.

Dosage forms for enteral administration include pills, tablets, caplets and capsules (chewable, dissolvable or swallow), time-release and sustained-release tablets and capsules, powders of granules, pellets, teas, drops, liquid or syrups (solution, softgel, suspension, emulsion, elixir, tincture, hydrogel), film, lollipop, lozenges, chewing gum, and oral spray. In such dosage forms, the active ingredient is ordinarily combined with one or more pharmaceutically acceptable excipients, examples of which are detailed above. Oral preparations may also be administered as aqueous suspensions, elixirs, or syrups. For these, the active ingredient may be combined with various sweetening or flavoring agents, coloring agents, and, if so desired, emulsifying and/or suspending agents, as well as diluents such as water, ethanol, glycerin, and combinations thereof. For administration by inhalation, the compounds are delivered in the form of an aerosol spray from pressured container or dispenser which contains a suitable propellant, e.g., a gas such as carbon dioxide, or a nebulizer.

For parenteral administration, the preparation may be an aqueous or an oil-based solution. Aqueous solutions may include a sterile diluent such as water, saline solution, a pharmaceutically acceptable polyol such as glycerol, propylene glycol, or other synthetic solvents; an antibacterial and/or antifungal agent such as benzyl alcohol, methyl paraben, chlorobutanol, phenol, thimerosal, and the like; an antioxidant such as ascorbic acid or sodium bisulfite; a chelating agent such as etheylenediaminetetraacetic acid; a buffer such as acetate, citrate, or phosphate; and/or an agent for the adjustment of tonicity such as sodium chloride, dextrose, or a polyalcohol such as mannitol or sorbitol. The pH of the aqueous solution may be adjusted with acids or bases such as hydrochloric acid or sodium hydroxide. Oil-based solutions or suspensions may further comprise sesame, peanut, olive oil, or mineral oil. For additional information regarding intraperitoneal administration, see de Vin et al., Peritoneal Dialysis International 2009; 29: 5-15.

The compositions may be presented in unit-dose or multi-dose containers, for example sealed ampoules and vials, and may be stored in a freeze-dried (lyophilized) condition requiring only the addition of the sterile liquid carried, for example water for injections, immediately prior to use. Extemporaneous injection solutions and suspensions may be prepared from sterile powders, granules and tablets.

II. Methods

In an aspect, the present invention provides a method of detecting enzyme activity associated with a disease or condition in a subject. The method comprises: (a) administering to the subject an effective amount of a composition comprising: a cleavable peptide and a first and second radionuclide, wherein the first and second radionuclide are separated by a site susceptible to cleavage by an enzyme and can be spectrally differentiated; (b) imaging the subject for a signal corresponding to the first and second radionuclide to determine the biodistribution for the first and second radionuclide; and (c) comparing the biodistribution of the first radionuclide to the biodistribution of the second radionuclide, wherein when the biodistribution for the first radionuclide differs from the biodistribution for the second radionuclide, enzyme activity is detected. In certain embodiments, the composition comprises: a particle, a cleavable peptide and a first and second radionuclide, wherein the first and second radionuclide are separated by a site susceptible to cleavage by an enzyme and can be spectrally differentiated and the second radionuclide is capable of being released upon cleavage.

In another aspect, the present invention provides a method of detecting lung injury in a subject. The method comprises (a) administering to the subject an effective amount of a composition comprising: a cleavable peptide comprising a MMP9 sensitive site, and a first and second radionuclide, wherein the first and second radionuclide are separated by the MMP9 sensitive site and can be spectrally differentiated; (b) imaging the subject for a signal corresponding to the first and second radionuclide to determine the biodistribution for the first and second radionuclide; and (c) comparing the biodistribution of the first radionuclide to the biodistribution of the second radionuclide, wherein when the biodistribution for the first radionuclide differs from the biodistribution for the second radionuclide, lung injury is detected. In certain embodiments, the composition comprises: a particle, a cleavable peptide comprising a MMP9 sensitive site and a first and second radionuclide, wherein the first and second radionuclide are separated by the MMP9 sensitive site and can be spectrally differentiated and the second radionuclide is capable of being released upon cleavage.

In still another aspect, the present invention provides a method of detecting a tumor in a subject. The method comprises (a) administering to the subject an effective amount of a composition comprising: a cleavable peptide, and a first and second radionuclide, wherein the first and second radionuclide are separated by a site susceptible to cleavage by an enzyme and can be spectrally differentiated; (b) imaging the subject for a signal corresponding to the first and second radionuclide to determine the biodistribution for the first and second radionuclide; and (c) comparing the biodistribution of the first radionuclide to the biodistribution of the second radionuclide, wherein when the biodistribution for the first radionuclide differs from the biodistribution for the second radionuclide, a tumor is detected. In certain embodiments, the composition comprises: a particle, a cleavable peptide and a first and second radionuclide, wherein the first and second radionuclide are separated by a site susceptible to cleavage by an enzyme and can be spectrally differentiated and the second radionuclide is capable of being released upon cleavage. In a specific embodiment, the cleavable peptide comprises a MMP9 sensitive site.

In yet another aspect, the invention provides a method for monitoring a response to treatment in a subject. The method comprises (a) administering to the subject an effective amount of a composition comprising: a cleavable peptide, and a first and second radionuclide, wherein the first and second radionuclide are separated by a site susceptible to cleavage by an enzyme and can be spectrally differentiated; (b) imaging the subject for a signal corresponding to the first and second radionuclide to determine the biodistribution for the first and second radionuclide; (c) repeating (a)-(b) at a later time, and subsequently comparing the biodistribution of the first and second radionuclide in the first imaging event to the biodistribution of the first and second radionuclide in the second imaging event, wherein a change in biodistribution between the first and second imaging events indicates a response to treatment. For example, if an enzyme is upregulated during disease and the difference between the biodistribution of the first and second radionuclide is greater in the first imaging event than the difference between the biodistribution of the first and second radionuclide in the second imaging event, then the subject is responding to treatment. Alternatively, if the difference between the biodistribution of the first and second radionuclide is the same or lower in the first imaging event than the difference between the biodistribution of the first and second radionuclide in the second imaging event, then the subject is not responding to treatment and/or the disease has progressed. In certain embodiments, the composition comprises: a particle, a cleavable peptide and a first and second radionuclide, wherein the first and second radionuclide are separated by a site susceptible to cleavage by an enzyme and can be spectrally differentiated and the second radionuclide is capable of being released upon cleavage.

The invention comprises, in part, imaging a subject. Imaging may be used to determine the biodistribution of the radionuclides. As used herein, "biodistribution" is a method of tracking where the radionuclides travel in the subject. Non-limiting examples of modalities of imaging may include magnetic resonance imaging (MRI), ultrasound (US), computed tomography (CT), Positron Emission Tomography (PET), Single Photon Emission Computed Tomography (SPECT), and optical imaging (OI, bioluminescence and fluorescence). Radioactive molecular probes are traditionally imaged with PET, SPECT or gamma (γ) cameras, by taking advantage of the capability of these imaging modalities to detect the high energetic γ rays. In a specific embodiment, a subject is imaged with SPECT. In another specific embodiment, a subject is imaged with SPECT-CT.

The subject may be imaged minutes, hours or days after administration of a composition of the invention. Accordingly, the subject may be imaged from about 10 to about 15 minutes, or from about 15 to about 30 minutes, or from about 30 minutes to about 45 minutes, or from about 45 minutes to 60 minutes after administration of a composition of the invention. Alternatively, the subject may be imaged from about 1 hour to about 2 hours, or from about 2 hours to about 3 hours, or from about 3 hours to about 4 hours, or from about 4 hours to about 5 hours, or from about 5 hours to about 6 hours, or from about 6 hours to about 7 hours, or from about 7 hours to about 8 hours after administration of a composition of the invention. In certain embodiments, a subject may be imaged from about 4 hours to about 48 hours after administration of a composition of the invention. In another embodiment, the subject may be imaged from about 1 day to about 2 days, or from about 2 days to about 3 days, or from about 3 days to about 4 days, or from about 4 days to about 5 days, or from about 5 days to about 6 days, or from about 6 days to about 7 days after administration of a composition of the invention.

In still yet another aspect, the invention provides a method for treating, stabilizing and/or preventing cancer and associated diseases in a subject. The method comprises administering to the subject an effective amount of a composition comprising: a cleavable peptide, and a first and second radionuclide, wherein the first and second radionuclide are separated by a site susceptible to cleavage by an enzyme and can be spectrally differentiated, thereby treating, stabilizing and/or preventing the cancer or the associated diseases. In certain embodiments, the composition comprises: a particle, a cleavable peptide and a first and second radionuclide, wherein the first and second radionuclide are separated by a site susceptible to cleavage by an enzyme and can be spectrally differentiated and the second radionuclide is capable of being released upon cleavage. In the foregoing embodiment, the particle may comprise a therapeutic agent. In other embodiments, the first radionuclide is a radionuclide used in radiotherapy. By "treating, stabilizing, or preventing cancer" is meant causing a reduction in the size of a tumor or in the number of cancer cells, slowing or preventing an increase in the size of a tumor or cancer cell proliferation, increasing the disease-free survival time between the disappearance of a tumor or other cancer and its reappearance, preventing an initial or subsequent occurrence of a tumor or other cancer, or reducing an adverse symptom associated with a tumor or other cancer. In a desired embodiment, the percent of tumor or cancerous cells surviving the treatment is at least 20, 40, 60, 80, or 100% lower than the initial number of tumor or cancerous cells, as measured using any standard assay (e.g., caspase assays, TUNEL and DNA fragmentation assays, cell permeability assays, and Annexin V assays). Desirably, the decrease in the number of tumor or cancerous cells induced by administration of a composition of the invention is at least 2, 5, 10, 20, or 50-fold greater than the decrease in the number of non-tumor or non-cancerous cells. Desirably, the methods of the present invention result in a decrease of 20, 40, 60, 80, or 100% in the size of a tumor or in the number of cancerous cells, as determined using standard methods. Desirably, at least 20, 40, 60, 80, 90, or 95% of the treated subjects have a complete remission in which all evidence of the tumor or cancer disappears. Desirably, the tumor or cancer does not reappear or reappears after at least 5, 10, 15, or 20 years.

(a) Subject

A subject of the invention may be a human, a livestock animal, a companion animal, a lab animal, or a zoological animal. In one embodiment, the subject may be a rodent, e.g. a mouse, a rat, a guinea pig, etc. In another embodiment, the subject may be a livestock animal. Non-limiting examples of suitable livestock animals may include pigs, cows, horses, goats, sheep, llamas and alpacas. In yet another embodiment, the subject may be a companion animal. Non-limiting examples of companion animals may include pets such as dogs, cats, rabbits, and birds. In yet another embodiment, the subject may be a zoological animal. As used herein, a "zoological animal" refers to an animal that may be found in a zoo. Such animals may include non-human primates, large cats, wolves, and bears. In certain embodiments, the animal is a laboratory animal. Non-limiting examples of a laboratory animal may include rodents, canines, felines, and non-human primates. In certain embodiments, the animal is a rodent. Non-limiting examples of rodents may include mice, rats, guinea pigs, etc.

(b) Tumor

A composition of the invention may be used to treat or recognize a tumor derived from a neoplasm or a cancer. "Neoplasm" is any tissue, or cell thereof, characterized by abnormal growth as a result of excessive cell division. The neoplasm may be malignant or benign, the cancer may be primary or metastatic; the neoplasm or cancer may be early stage or late stage. Non-limiting examples of neoplasms or cancers that may be treated or detected include acute lymphoblastic leukemia, acute myeloid leukemia, adrenocortical carcinoma, AIDS-related cancers, AIDS-related lymphoma, anal cancer, appendix cancer, astrocytomas (childhood cerebellar or cerebral), basal cell carcinoma, bile duct cancer, bladder cancer, bone cancer, brainstem glioma, brain tumors (cerebellar astrocytoma, cerebral astrocytoma/malignant glioma, ependymoma, medulloblastoma, supratentorial primitive neuroectodermal tumors, visual pathway and hypothalamic gliomas), breast cancer, bronchial adenomas/carcinoids, Burkitt lymphoma, carcinoid tumors (childhood, gastrointestinal), carcinoma of unknown primary, central nervous system lymphoma (primary), cerebellar astrocytoma, cerebral astrocytoma/malignant glioma, cervical cancer, childhood cancers, chronic lymphocytic leukemia, chronic myelogenous leukemia, chronic myeloproliferative disorders, colon cancer, cutaneous T-cell lymphoma, desmoplastic small round cell tumor, endometrial cancer, ependymoma, esophageal cancer, Ewing's sarcoma in the Ewing family of tumors, extracranial germ cell tumor (childhood), extragonadal germ cell tumor, extrahepatic bile duct cancer, eye cancers (intraocular melanoma, retinoblastoma), gallbladder cancer, gastric (stomach) cancer, gastrointestinal carcinoid tumor, gastrointestinal stromal tumor, germ cell tumors (childhood extracranial, extragonadal, ovarian), gestational trophoblastic tumor, gliomas (adult, childhood brain stem, childhood cerebral astrocytoma, childhood visual pathway and hypothalamic), gastric carcinoid, hairy cell leukemia, head and neck cancer, hepatocellular (liver) cancer, Hodgkin lymphoma, hypopharyngeal cancer, hypothalamic and visual pathway glioma (childhood), intraocular melanoma, islet cell carcinoma, Kaposi sarcoma, kidney cancer (renal cell cancer), laryngeal cancer, leukemias (acute lymphoblastic, acute myeloid, chronic lymphocytic, chronic myelogenous, hairy cell), lip and oral cavity cancer, liver cancer (primary), lung cancers (non-small cell, small cell), lymphomas (AIDS-related, Burkitt, cutaneous T-cell, Hodgkin, non-Hodgkin, primary central nervous system), macroglobulinemia (Waldenström), malignant fibrous histiocytoma of bone/osteosarcoma, medulloblastoma (childhood), melanoma, intraocular melanoma, Merkel cell carcinoma, mesotheliomas (adult malignant, childhood), metastatic squamous neck cancer with occult primary, mouth cancer, multiple endocrine neoplasia syndrome (childhood), multiple myeloma/plasma cell neoplasm, mycosis fungoides, myelodysplastic syndromes, myelodysplastic/myeloproliferative diseases, myelogenous leukemia (chronic), myeloid leukemias (adult acute, childhood acute), multiple myeloma, myeloproliferative disorders (chronic), nasal cavity and paranasal sinus cancer, nasopharyngeal carcinoma, neuroblastoma, non-Hodgkin lymphoma, non-small cell lung cancer, oral cancer, oropharyngeal cancer, osteosarcoma/malignant fibrous histiocytoma of bone, ovarian cancer, ovarian epithelial cancer (surface epithelial-stromal tumor), ovarian germ cell tumor, ovarian low malignant potential tumor, pancreatic cancer, pancreatic cancer (islet cell), paranasal sinus and nasal cavity cancer, parathyroid cancer, penile cancer, pharyngeal cancer, pheochromocytoma, pineal astrocytoma, pineal germinoma, pineoblastoma and supratentorial primitive neuroectodermal tumors (childhood), pituitary adenoma, plasma cell neoplasia, pleuropulmonary blastoma, primary central nervous system lymphoma, prostate cancer, rectal cancer, renal cell carcinoma (kidney cancer), renal pelvis and ureter transitional cell cancer, retinoblastoma, rhabdomyosarcoma (childhood), salivary gland cancer, sarcoma (Ewing family of tumors, Kaposi, soft tissue, uterine), Sézary syndrome, skin cancers (nonmelanoma, melanoma), skin carcinoma (Merkel cell), small cell lung cancer, small intestine cancer, soft tissue sarcoma, squamous cell carcinoma, squamous neck cancer with occult primary (metastatic), stomach cancer, supratentorial primitive neuroectodermal tumor (childhood), T-Cell lymphoma (cutaneous), testicular cancer, throat cancer, thymoma (childhood), thymoma and thymic carcinoma, thyroid cancer, thyroid cancer (childhood), transitional cell cancer of the renal pelvis and ureter, trophoblastic tumor (gestational), enknown primary site (adult, childhood), ureter and renal pelvis transitional cell cancer, urethral cancer, uterine cancer (endometrial), uterine sarcoma, vaginal cancer, visual pathway and hypothalamic glioma (childhood), vulvar cancer, Waldenström macroglobulinemia, and Wilms tumor (childhood). In a preferred embodiment, the cancer is selected from the group consisting of bladder carcinoma, breast carcinoma, cervical carcinoma, cholangiocarcinoma, colorectal carcinoma, esophageal carcinoma, gastric sarcoma, glioma, lung carcinoma, lymphoma, melanoma, multiple myeloma, osteosarcoma, ovarian carcinoma, pancreatic carcinoma, prostate carcinoma, stomach carcinoma, a head, a neck tumor, and a solid tumor. In a specific embodiment, the cancer may be breast cancer. In another specific embodiment, the cancer may be epidermoid carcinoma.

(c) Administration

In certain aspects, a pharmacologically effective amount of a composition of the invention may be administered to a subject. Administration is performed using standard effective techniques, including peripherally (i.e. not by administration into the central nervous system) or locally to the central nervous system. Peripheral administration includes but is not limited to intratumoral, intratracheal, intravenous, intraperitoneal, subcutaneous, pulmonary, transdermal, intramuscular, intranasal, buccal, sublingual, or suppository administration. Local administration, including directly into the central nervous system (CNS) includes but is not limited to via a lumbar, intraventricular or intraparenchymal catheter or using a surgically implanted controlled release formulation.

Pharmaceutical compositions for effective administration are deliberately designed to be appropriate for the selected mode of administration, and pharmaceutically acceptable excipients such as compatible dispersing agents, buffers, surfactants, preservatives, solubilizing agents, isotonicity agents, stabilizing agents and the like are used as appropriate. Remington's Pharmaceutical Sciences, Mack Publishing Co., Easton Pa., 16Ed ISBN: 0-912734-04-3, latest edition, incorporated herein by reference in its entirety, provides a compendium of formulation techniques as are generally known to practitioners. It may be particularly useful to alter the solubility characteristics of the peptides useful in this discovery, making them more lipophilic, for example, by encapsulating them in liposomes or by blocking polar groups.

Effective peripheral systemic delivery by intravenous or intratumor or intraperitoneal or subcutaneous injection is a preferred method of administration to a living patient. Suitable vehicles for such injections are straightforward. In addition, however, administration may also be effected through the mucosal membranes by means of nasal aerosols or suppositories. For example, intratracheal administration may be used. When administration to the lungs is desired, a composition comprising a particle as described in Section I(b) may be preferable. Suitable formulations for such modes of administration are well known and typically include surfactants that facilitate cross-membrane transfer. Such surfactants are often derived from steroids or are cationic lipids, such as N-[1-(2,3-dioleoyl)propyl]-N,N,N-trimethyl ammonium chloride (DOTMA) or various compounds such as cholesterol hemisuccinate, phosphatidyl glycerols and the like.

For diagnostic applications, a detectable amount of a composition of the invention is administered to a subject. A "detectable amount", as used herein to refer to a diagnostic composition, refers to a dose of such a composition that the presence of the composition can be determined in vivo or in vitro. A detectable amount will vary according to a variety of factors, including but not limited to chemical features of the drug being labeled, the detectable label, labeling methods, the method of imaging and parameters related thereto, metabolism of the labeled drug in the subject, the stability of the label (e.g. the half-life of a radionuclide label), the time elapsed following administration of the drug and/or labeled peptide prior to imaging, the route of drug administration, the physical condition and prior medical history of the subject, and/or the size and longevity of the tumor or suspected tumor. Thus, a detectable amount can vary and can be tailored to a particular application. After study of the present disclosure, and in particular the Examples, it is within the skill of one in the art to determine such a detectable amount.

For therapeutic applications, a therapeutically effective amount of a composition of the invention is administered to a subject. A "therapeutically effective amount" is an amount of the therapeutic composition sufficient to produce a measurable biological response (e.g., an immunostimulatory, an anti-angiogenic response, a cytotoxic response, or tumor regression). Actual dosage levels of active ingredients in a therapeutic composition of the invention can be varied so as to administer an amount of the active compound(s) that is effective to achieve the desired therapeutic response for a particular subject. The selected dosage level will depend upon a variety of factors including the activity of the therapeutic composition, formulation, the route of administration, combination with other drugs or treatments, tumor size and longevity, and the physical condition and/or prior medical history of the subject being treated. In some embodiments, a minimal dose is administered, and dose is escalated in the absence of dose-limiting toxicity. Determination and adjustment of a therapeutically effective dose, as well as evaluation of when and how to make such adjustments, are known to those of ordinary skill in the art of medicine.

The frequency of dosing may be daily or once, twice, three times or more per week or per month, as needed as to effectively treat the symptoms. The timing of administration of the treatment relative to the disease itself and duration of treatment will be determined by the circumstances surrounding the case. Treatment could begin immediately, such as at the site of the injury as administered by emergency medical personnel. Treatment could begin in a hospital or clinic itself, or at a later time after discharge from the hospital or after being seen in an outpatient clinic. Duration of treatment could range from a single dose administered on a one-time basis to a life-long course of therapeutic treatments.

Although the foregoing methods appear the most convenient and most appropriate and effective for administration of peptides, by suitable adaptation, other effective techniques for administration, such as intraventricular administration, transdermal administration and oral administration may be employed provided proper formulation is utilized herein.

In addition, it may be desirable to employ controlled release formulations using biodegradable films and matrices, or osmotic mini-pumps, or delivery systems based on dextran beads, alginate, or collagen.

Typical dosage levels can be determined and optimized using standard clinical techniques and will be dependent on the mode of administration.

TABLE A

Sequences

| SEQ ID NO: | Sequence |
|---|---|
| 1 | Gly-Pro-Leu-Gly-Val-Arg-Gly-Lys-Gly-Tyr-Gly-Ahx-Cys |
| 2 | Asp-Glu-Val-Asp |
| 3 | Gly-Arg-Arg-Arg-Orn-Arg-Arg-Lys-Lys-Arg-Lys |
| 4 | Tyr-Leu-Ala-Ile-Ahx-Pro-Ala |
| 5 | Ahx-Tyr-Ahx-Asp-Glu-Val-Asp-Gly-Lys-Gly-Cys |
| 6 | Tyr-Leu-Ala-Ile-Ahx-Pro-Ala-Asp-Glu-Val-Asp-Gly-Arg-Arg-Arg-Orn-Arg-Arg-Lys-Lys-Arg-Lys |

EXAMPLES

The following examples are included to demonstrate preferred embodiments of the invention. It should be appreciated by those of skill in the art that the techniques disclosed in the examples that follow represent techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1. Dual-Radiolabeled Multifunctional Nanoparticle SPECT Probes for Cancer Imaging With proper design, nanoparticles (NPs) offer multifunctional properties that can be harnessed for both diagnostic and therapeutic biomedical applications.[1] Due to their localized surface plasmon resonant (LSPR) properties, gold NPs[2] in particular offer unique optical properties that can be used for imaging or photothermal therapy[3] of either cancerous[4] or bacterial[5] cells. Incorporating radioactive functionality into NPs[6] is an emerging strategy to quantitatively evaluate their in vivo performance with quantitative biodistribution and imaging modalities such as positron emission tomography (PET)[7] and optical Cerenkov imaging.[8] Distinct from PET that only detects 511 keV gamma ray pairs, single photon emission computed tomography (SPECT) has the ability to detect a range of photonic energies, and therefore can be employed in multispectral imaging using multiple radionuclides. When properly integrated with NP probes, this independent tracking can help characterize important in vivo parameters such as radiolabeling stability, surface anchor stability, and biological parameters such as enzyme activity.

Figure 4:
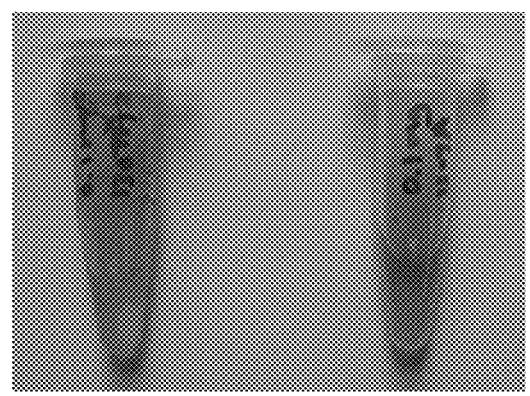
FIG. 4 depicts an image of gold nanoparticle suspensions after incubation with the synthesized peptide both (left) without and (right) with the addition of mPEG-SH (MW5000). The red color associated with the surface plasmon resonance of a well-dispersed suspension was only preserved with addition of PEG.

In this study, a multifunctional nanoparticle (NP) agent was designed to passively target tumors and characterize MMP activity using a dual-radiolabeling strategy. The strategy takes inspiration from optically-activatable probes used to image enzyme activity,[9] and it involves the synthesis of an imaging agent containing two distinct radionuclides, whose gamma emissions can be spectrally differentiated, separated by a cleavable linker.[10] The surface of gold nanoparticles was functionalized with a peptide (DTPA-Gly-Pro-Leu-Gly-Val-Arg-Gly-Lys-Gly-Tyr-Gly-Ahx-Cys-NH$_2$—SEQ ID NO:1) containing four important components: (1) a sequence which is cleaved specifically in the presence of MMP9, (2) a tyrosine residue to radiolabel with $^{125}$I, (3) a DTPA chelator to radiolabel with radiometals ($^{64}$Cu and $^{111}$In), and (4) a cysteine residue to anchor to the gold surface. In addition, PEG was incorporated onto the NP surface, which was necessary to stabilize the peptide-functionalized NP suspension in aqueous environments (FIG. 4).

Figure 5:
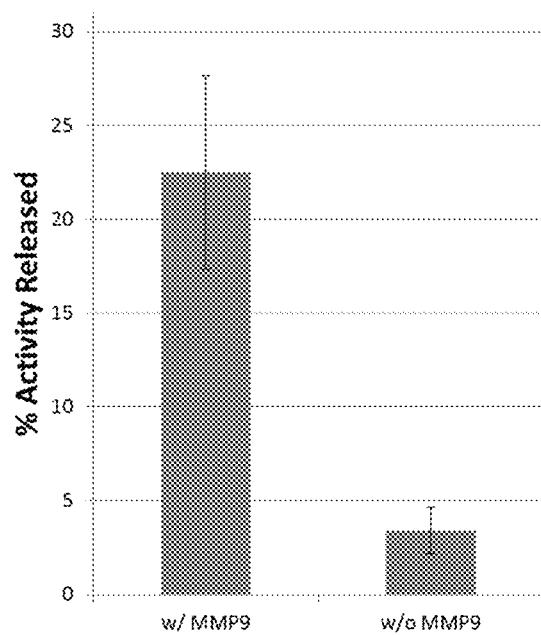
FIG. 5 depicts a graphical quantification of MMP9 activity with the multifunctional nanoparticle (NP). The bars represent the percent of total activity that was found in the supernatant solution after 1.5 hour incubation with MMP9.
Figure 6A:
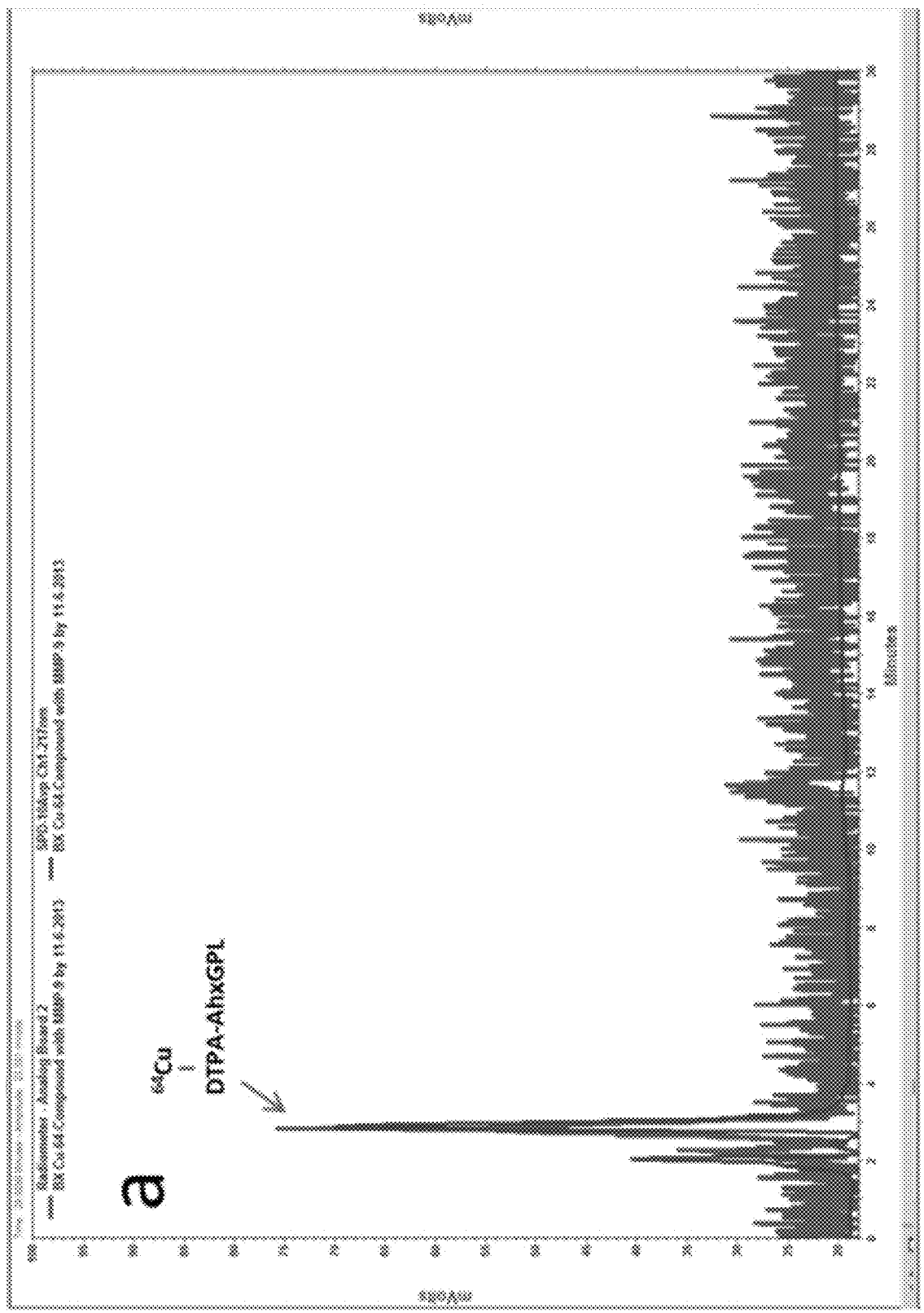
FIG. 6A-6B depicts graphs illustrating the results of high performance liquid chromatography of supernatant solutions after incubation of $^{64}$Cu-labeled nanoparticles (FIG. 6A) with MMP9 or (FIG. 6B) without MMP9.
Figure 6B:
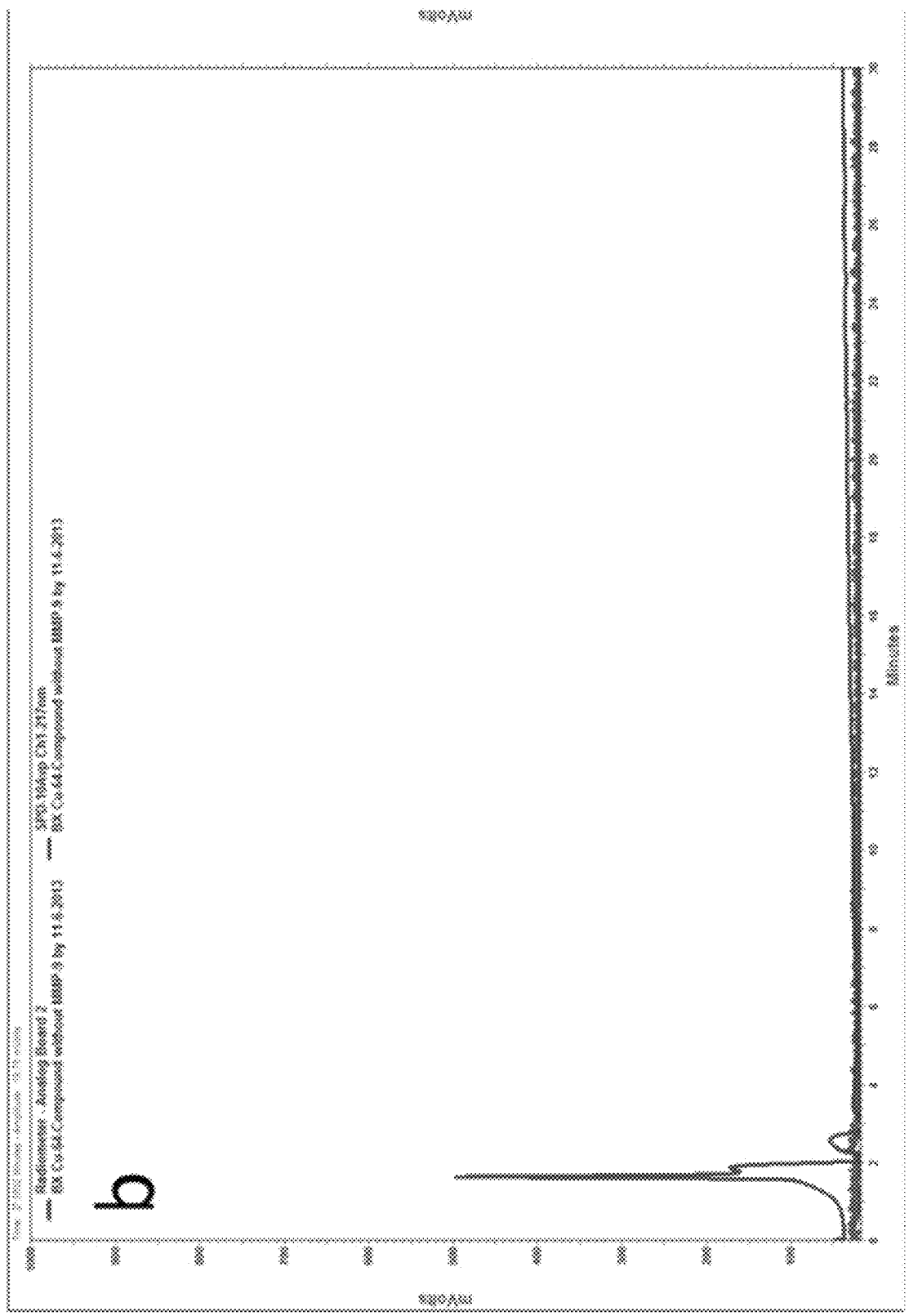

Once surface-functionalized with the peptide and PEG, an experiment was performed in PBS in order to characterize the ability of MMP9 to cleave the peptide present on the nanoparticle surface. In this experiment, $^{64}$Cu was chelated to DTPA on the peptide attached to the NP. The suspension was incubated with MMP9 for 1.5 hours and then the supernatant solution was separated from the NPs by centrifugal filtration. Importantly, 23% of the radioactivity was observed in the supernatant after incubation with MMP9 compared to less than <5% in a control without MMP9 (FIG. 5), which is attributed to the $^{64}$Cu-labeled peptide fragment cleaved from the NP by MMP9. To further confirm the presence of the cleaved peptide, high performance liquid chromatography (HPLC) was performed on the supernatant solutions, and co-registered UV and radioactive peaks associated with the radiolabeled peptide fragment were observed (FIG. 6A and FIG. 6B).

For in vivo spectroscopic SPECT imaging, peptide-functionalized NPs were dual radiolabeled with $^{111}$In and $^{125}$I. The NP was radiolabeled in two successive steps (FIG. 1). First $^{111}$InCl$_3$ was added to a pellet of the surface-functionalized NP in an acidic buffer under mild heating (45° C.) and incubated for one hour, resuspended in PBS buffer, and centrifuged to remove unchelated $^{111}$In. Radiochemical purity of the pellet was characterized with thin layer chromatography (TLC) and confirmed to be>95%. Then the pellet suspended in PBS was added to an iodigen tube and incubated with Na $^{125}$I for one hour. Once again, TLC was performed to ensure radiochemical purity greater than 95%.

Figure 7:
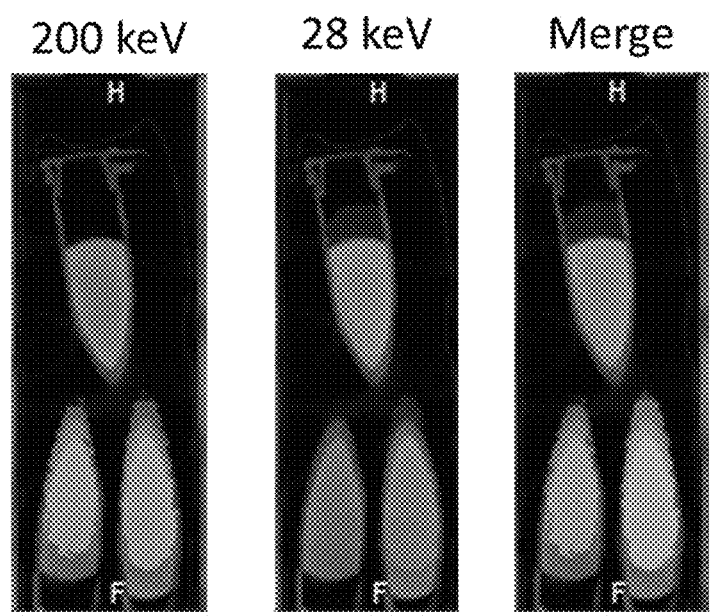
FIG. 7 depicts imaging results from a SPECT phantom study with dual-radiolabeled nanoparticles (bottom right), along with $^{111}$In control (bottom left) and $^{125}$I control. X-ray CT of vials along with (left panel) 200 keV energy SPECT channel, (middle panel) 28 keV energy SPECT channel, and (right panel) merged energy SPECT channels.

Next, a phantom study was performed on the multifunctional NP suspension in order to confirm the spectroscopic imaging capability with the dual-radiolabeled agent. The dual-radiolabeled suspension was imaged along with two controls containing only $^{111}$In or $^{125}$I. Two imaging windows were chosen to independently collect photonic emissions from $^{111}$In and $^{125}$I. More specifically, a narrow window centered at 28 keV was used to detect x-ray emissions from $^{125}$I (colored blue), and a broad window centered around 200 keV was used to acquire gamma emissions from $^{111}$In (colored red). As can be observed in FIG. 7, the two control vials only appear as separate colors representing respective energy windows, while the dual-radiolabeled sample contains signal from both energy windows. When the two channels are merged, the NP sample appears purple due to the presence of both $^{125}$I and $^{111}$In.

Figure 2:
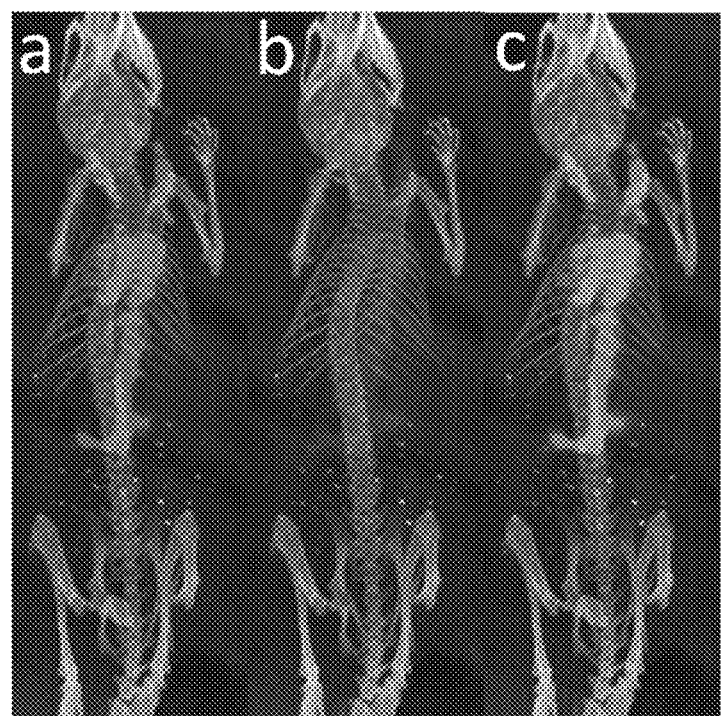
FIG. 2 depicts in vivo spectroscopic SPECT/CT imaging after intravenous injection with dual-radiolabeled nanoparticles. X-ray CT coregistered with (a) 200±60 keV energy channel that detects $^{111}$In, (b) 28±3 keV energy channel that detects $^{125}$I emission, and (c) both energy channels.
Figure 8:
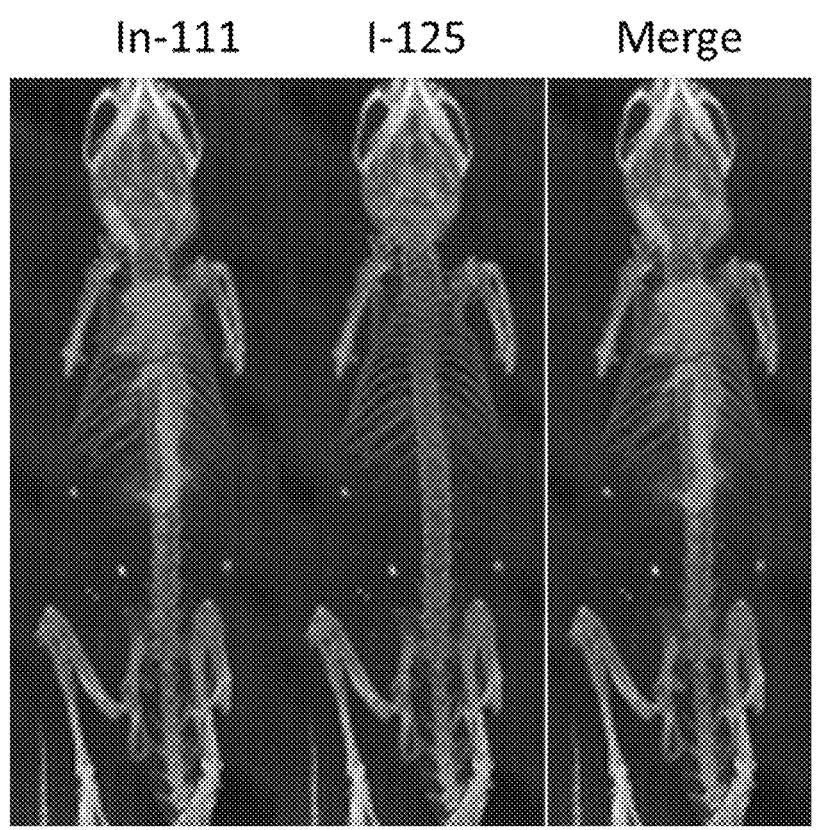
FIG. 8 depicts SPECT/CT imaging of mice 4 hours after injection with the dual-radiolabeled nanoparticles. X-ray CT can be seen with (left panel) 200 keV SPECT channel, (middle panel) 28 keV SPECT channel, and (right panel) merged energy SPECT channels.

To explore the in vivo pharmacokinetics and biodistribution of these multifunctional NPs, suspensions were intravenously injected into tumor-bearing mice and in vivo imaging was performed (FIG. 2). Importantly, both $^{111}$In and $^{125}$I signals could be independently detected in the mice (FIGS. 2A-B), and were co-registered mainly in the blood pool, with the heart, carotid arteries, and descending aorta all clearly visible (purple signal seen in FIG. 2C). In addition, $^{125}$I was identified in the thyroid, and $^{111}$In was observed in the bladder. Interestingly, 4 hours after injection, while the $^{111}$In signal was still present mainly in the blood, the $^{125}$I signal was isolated to the thyroid, stomach, and bladder (FIG. 8). This result is attributed to functional in vivo stability of the $^{111}$In chelation by DTPA and the thiol anchorage to the gold NP surface, coupled with a lack of in vivo $^{125}$I radiolabeling stability, which has been reported previously. Therefore, only the $^{111}$In channel was used for later imaging time points.

Figure 9:
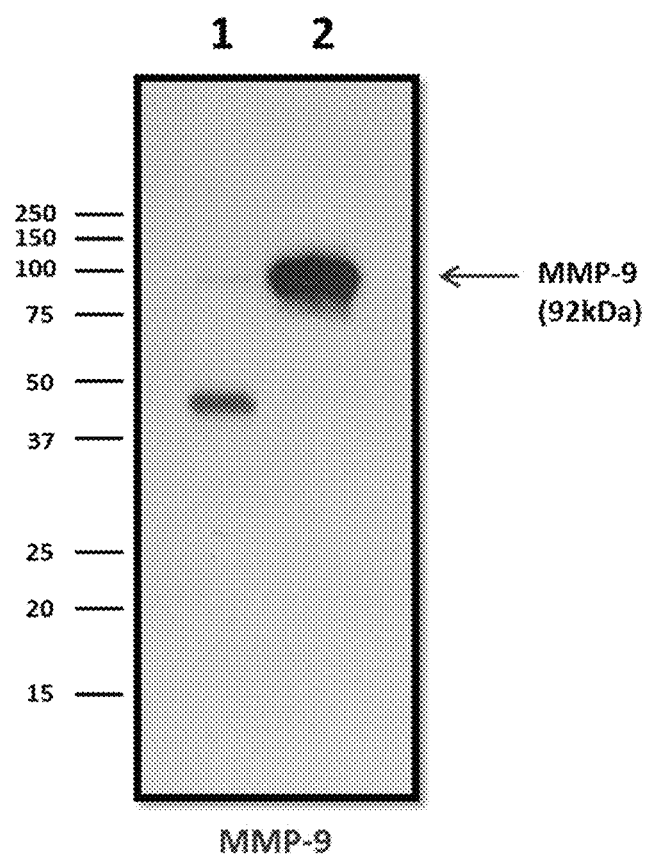
FIG. 9 depicts a western blot for MMP-9 of (1) 4T1Luc and (2) A431 cells used to grow in vivo tumors.
Figure 10:
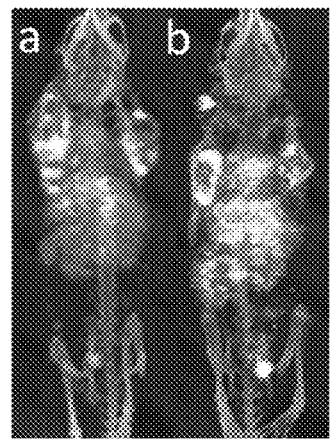
FIG. 10 depicts SPECT/CT imaging of (a) A431 tumor-bearing and (b) 4T1Luc-tumor bearing mice 24 hours after injection using the 200 keV energy channel.

Two types of tumors with differing MMP9 expression levels (high=A431; low=4T1Luc; FIG. 9) were grown in order to explore the ability of the nanoprobe to report the relative MMP9 activity in vivo. By 24 hours, both types of tumors were clearly visible using the $^{111}$In imaging channel (FIG. 10). Significant tumor accumulation was quantified from the images, corresponding to standardized uptake values (SUVs) of 2.03±0.21 (7.25±0.76% ID/gram of tissue) and 1.79±0.19 (6.41±0.57% ID/gram) for the A431 and 4T1Luc tumors, respectively. The multifunctional NPs passively accumulated around the edges of both types of tumors through the enhanced permeability and retention (EPR) effect. Further, the heart is still clearly visible at the 24 hour time point, evidence that a significant portion of the NP probe is still circulating in the blood even at this late time point. The NP formulation of the probe was key to this long blood circulation that impeded clearance through the kidney, which occurred for PEG-peptide controls within 4 hours (data not shown), a property that may be advantageous in future drug delivery or imaging applications where sustained presence in the blood is necessary.

Figure 3:
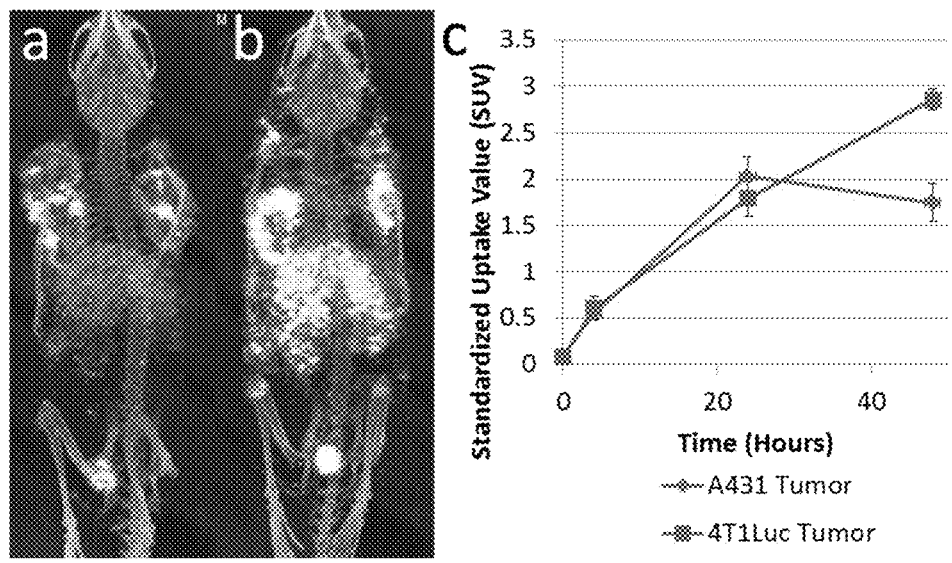
FIG. 3 depicts tumor imaging with dual-radiolabeled nanoparticles. SPECT/CT images of mice with bilateral (a) A431 and (b) 4T1Luc tumors 48 hours after intravenous injection. (c) Tumor standardized uptake values (SUVs) of $^{111}$In over the 48 hours following injection.
Figure 11:
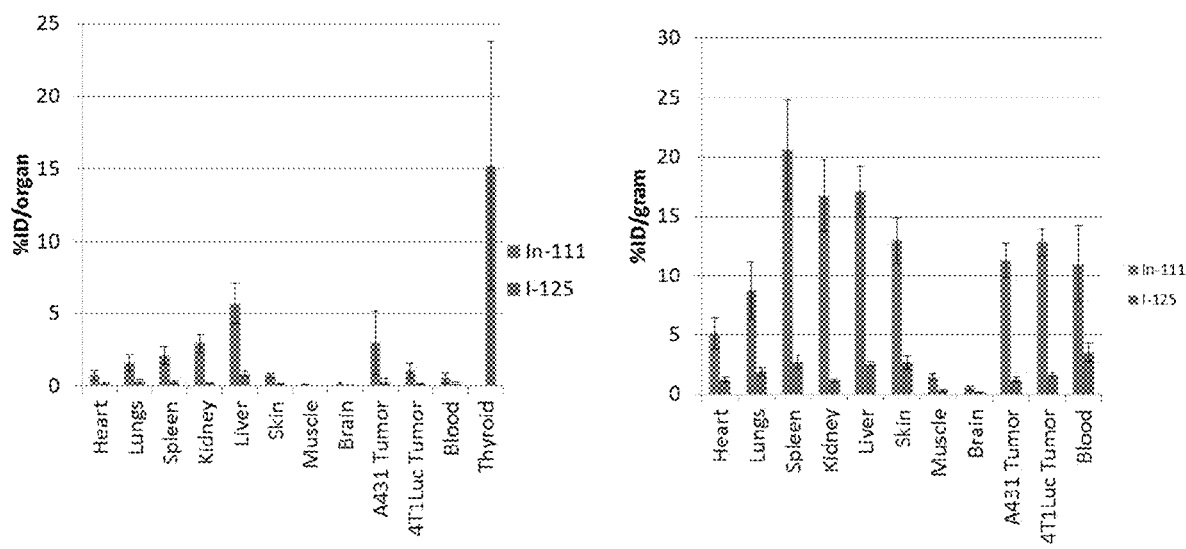
FIG. 11 depicts graphs of biodistribution from mice sacrificed after the 48 hour imaging time point.

By 48 hours, both types of tumors were still visible, and due to a loss of signal in the blood pool, provided significant tumor to muscle ratios of ~8 (FIG. 3A-B), which was validated in the biodistribution results (FIG. 11). Further, and most interestingly, a significant difference in accumulation was observed between the tumors with high and low MMP9 expression (FIG. 3C). Whereas the 4T1Luc tumors with low MMP9 expression continued to accumulate signal between 24 and 48 hours and reached an SUV of 2.8±0.11 (10.2±0.33% ID/gram), a decrease in SUV over the same time period to 1.75±0.2 (6.23±0.72% ID/gram) was observed in the A431 tumors with high MMP9 expression. It is hypothesized this pharmacokinetic difference in uptake between the two tumor types is a result of their differences in MMP9 expression. More specifically, once the $^{111}$In-labeled NPs accumulated in tumors through the EPR effect, A431 tumors with significant MMP9 expression cleaved the $^{111}$In-labeled peptide fragment from the NP, causing clearance from the tumor between 24 and 48 hours. Once again, the NP is central to the success of the strategy, in this case helping to avoid non-specific clearance of uncleaved peptides.

Future work will seek to confirm and expand on targeting MMP activity, incorporate more stable radiochemistry compared to the tyrosine-iodine in order to integrate ratiometric imaging capability, quantify anchorage stability, and optimize the localized surface plasmon resonant properties of the gold cores for image-guided photothermal therapy.[3]

Methods for Example 1

Peptide Synthesis

Standard Fmoc solid phase synthetic protocols were used to synthesize the peptide containing the MMP9 substrate, tyrosine residue, DTPA chelator, and cysteine anchor (Sequence: DTPA-Gly-Pro-Leu-Gly-Val-Arg-Gly-Lys-Gly-Tyr-Gly-Ahx-Cys-NH$_2$—SEQ ID NO:1). Briefly, amino acids were successively loaded onto rink amide resin (0.66 mmol/g resin) using a CEM Discover Liberty Microwave Peptide Synthesizer. The peptide was purified with a Gilson UV/Vis-152 high performance liquid chromatographer (HPLC) using a C18 preparation column. Molecular weight of 1648 g/mol was confirmed with matrix-assisted laser desorption ionization mass spectrometry (MALDI-MS).

Nanoparticle Surface Modification 10 mL of 10 nm diameter citrate-stabilized gold nanoparticle suspension (Sigma Aldrich; 6×10$^{12}$ particles/mL) was centrifuged for 1.5 hours at 20.3 g. Supernatant was removed, and the nanoparticle pellet was resuspended in 5 mL of ultrapure water containing 2.2 mg mPEG-SH (MW5000) and 1 mg of synthesized peptide. After 20 minutes of sonication, the suspension was shaken for 48 hours, then centrifuged for 1.5 hours at 20.3 g. Supernatant was again removed, 5 mL 0.1 M NH$_4$OAc (pH 5.5) was added, and suspension was centrifuged for 2 hours at 13.9 g. Supernatant was removed, leaving a 40 μL gold nanoparticle pellet.

In Vitro MMP9 Experiment 1 mL of peptide-functionalized gold NPs was centrifuged, supernatant decanted, and resuspended in 0.1 M NH4OAc. 110 μCi $^{64}$Cu, provided by the Washington University Cyclotron Facility, was added to the NP pellet and shaken at 45° C. for 1 hour. Radiolabeled NPs were purified from nonchelated $^{64}$Cu by centrifugation. Then NP suspensions were incubated with 20 ng MMP9 for 1.5 hours, after which 450 μL PBS was added and supernatant was purified from the NPs by centrifugation filtration using a 10 k MW filter. Supernatant and NP pellets were counted for radioactivity in a PerkinElmer 1480 Automatic Gamma Counter.

Nanoparticle Dual-Radiolabeling Strategy 7.1 mCi $^{111}$InCl$_3$ (16 μL) was added to the 40 μL gold nanoparticle pellet and reacted at 45° C. for 75 minutes. 500 μL PBS was added to the pellet and centrifuged for 2 hours at 20 k g force. Supernatant was removed, leaving 5.6 mCi of $^{111}$In in the pellet. The pellet was then transferred to an iodogen tube and 3.4 mCi Na $^{125}$I (50 μL) was added and allowed to react for 1 hour. Radiochemical purity was quantified by thin layer chromatography (TLC).

SPECT Phantom Study 1 mL of the dual-radiolabeled NP (~100 μCi $^{111}$In and 70 μCi $^{125}$I) was placed in a 1.5 mL microcentrifuge tube, along with two 1 mL controls containing either only $^{125}$I (96 μCi) or only $^{111}$In (71 μCi). Tubes were imaged with 16 projection scans (15 seconds per scan) in a NanoSPECT/CT (Bioscan, Inc., Washington, D.C.) Two energy windows were simultaneously tracked in order to detect both $^{111}$In and $^{125}$I; 200±60 keV was monitored to track $^{111}$In, and 28±3 keV was used to track $^{125}$I.

Western Blot for MMP9

4T1Luc tumor and A431 tumor tissues were homogenized using an ultrasonic processor in CHAPS buffer (50 mM Pipes/HCl, pH 6.5, 5 mM dithiothreitol (DTT), 2 mM EDTA, 0.1% Chaps, 20 μg ml$^{-1}$ leupeptin, 10 μg ml$^{-1}$ pepstatin, 10 μg ml$^{-1}$ Aprotinin, 1 mM phenyl methylsulphonyl fluoride), and then the tissue lysates were clarified by centrifugation. After protein extraction, the protein concentration was determined by the Bio-Rad Protein assay reagent, the tumor samples were adjusted to an equal amount of protein (50 μg). Any kD Mini-Protean TGX Gel (Bio-Red, Hercules, Calif.) was performed using the EC120 Mini vertical gel system (Thermo EC, Holbrook, N.Y.). After SDS denaturing electrophoresis, proteins were transferred to PVDF membrane using an EC140 Mini Blot Module (Thermo EC, Holbrook, N.Y.) apparatus. The membrane was blocked 1 h at room temperature in PBS containing 5% nonfat dry milk (w/v), 0.1% (v/v) Tween-20 (PBS-T), followed by incubation with goat polyclonal anti-MMP-9 (R&D Systems Inc, Minneapolis, Minn.) primary antibody (0.1 μg/ml) in PBS-T containing 3% nonfat dry milk (w/v) at 4° C. overnight. After washing three times for 10 min each in PBS-T, the membrane was incubated for 1 h with diluted polyclonal rabbit anti-goat IgG conjugated to horseradish peroxidase in PBS-T containing 3% nonfat dry milk (w/v). Membrane was then washed three times for 10 min each in PBS-T and developed using the SuperSignal West Pico chemiluminescent Substrate (Pierce Biotechnology, Rockford, Ill.) according to the manufacturer's instruction.

Tumor Mouse Model

All animal studies were performed in compliance with guidelines set forth by the NIH Office of Laboratory Animal Welfare and approved by the Washington University Animal Studies Committee. The A431 (ATCC, Manassas, Va.) and 4T1Luc (Sibtech, Brookfield, Conn.) cells were cultured in Dulbecco's Modified Eagle Medium (DMEM) containing 10% (v/v) fetal bovine serum (Invitrogen, Carlsbad, Calif.) supplemented with penicillin (100 μg/mL) and streptomycin (100 μg/mL) in a humidified atmosphere of 5% $CO_2$ in air. To form bilateral xenograft tumors (2 tumors per mouse), 10$^6$ A431 cells in 100 μL phosphate buffered saline (PBS) were injected into each flanks of 12 week old male nude mice weighing 25-30 g, and tumors were allowed to grow for 18 days. In separate nude mice, 5×10$^5$ 4 T1Luc cells in 100 μL PBS were injected into each flanks, and tumors were allowed to grow for 8 days. Average tumor sizes for either type were ~100 mm$^3$.

SPECT/CT In Vivo Imaging

100 μL of dual radiolabeled gold nanoparticle suspension (~0.8 mCi $^{111}$In and 0.7 mCi $^{125}$I) was injected via the tail vein of nude mice bearing bilateral tumors (either A431 with high MMP9 expression or 4T1Luc with low MMP9 expression). SPECT/CT imaging was performed on the Nano-SPECT/CT. As described in the SPECT phantom study methods above, two energy windows were simultaneously tracked in order to detect both $^{111}$In and $^{125}$I. 16 projection scans (60 seconds per scan) were performed immediately after injection, as well as 4 hours, 24 hours, and 48 hours later. Tumor standardized uptake values (SUVs) were quantified from SPECT/CT images using Inveon Research Workspace software (Siemans).

Biodistribution

After the 48 hour time point, animals were sacrificed, and then organs were removed, weighed, and counted for radioactivity in a Wizard Model 1480 gamma counter both immediately after sacrifice and 2 weeks later to isolate signal from both $^{111}$In and $^{125}$I.

REFERENCES FOR EXAMPLE 1

1. Peer, D.; Karp, J.; Hong, S.; Farokhzad, O.; Margalit, R., Nanocarriers as an Emerging Platform for Cancer Therapy. *Nat. Nanotechnol.* 2007, 2, 751-760.
2. (a) Huang, X.; Jain, P.; El-Sayed, I.; El-Sayed, M., Gold Nanostructures: Interesting Optical Properties and Recent Applications in Cancer Diagnostics and Therapy. *Nanomedicine* 2007, 2, 681-693; (b) Cobley, C.; Chen, J.; Cho, E.; Wang, L.; Xia, Y., Gold Nanostructures: A Class of Multifunctional Materials for Biomedical Applications. *Chem. Soc. Rev.* 2011, 40 (44-56).
3. Wang, Y.; Black, K.; Luehmann, H.; Li, W.; Zhang, Y.; Cai, X.; Wan, D.; Liu, S.; Li, M.; Kim, P.; Li, Z.; Wang, L.; Liu, Y.; Xia, Y., Comparison Study of Gold Nanohexapods, Nanorods, and Nanocages for Photothermal Cancer Treatment. *ACS Nano* 2013, 7 (3), 2068-2077.
4. Black, K.; Yi, J.; Rivera, J.; Zelasko-Leon, D., Polydopamine-enabled surface functionalization of gold nanorods for cancer cell-targeted imaging and photothermal therapy. *Nanomedicine* 2013, 8 (1), 17-28.
5. Black, K.; Sileika, T.; Yi, J.; Zhang, R.; Rivera, J.; Messersmith, P., Bacterial Killing by Light-Triggered Release of Silver from Biomimetic Metal Nanorods. *Small* 2014, 10 (1), 169-178.
6. Zeng, D.; Lee, N.; Liu, Y.; Zhou, D.; Dence, C.; Wooley, K.; Katzenellenbogen, J.; Welch, M., 64Cu Core-Labeled Nanoparticles with High Specific Activity via Metal-Free Click Chemistry. *ACS Nano* 2012, 6 (6), 5209-5219.
7. (a) Wang, Y.; Liu, Y.; Luehmann, H.; Xia, X.; Brown, P.; Jarreau, C.; Welch, M.; Xia, Y., Evaluating the Pharmacokinetics and In Vivo Cancer Targeting Capability of Au Nanocages by Positron Emission Tomography Imaging. *ACS Nano* 2012, 6 (7), 5880-5888; (b) Zhao, Y.; Sultan, D.; Detering, L.; Cho, S.; Sun, G.; Pierce, R.; Wooley, K.; Liu, Y., Copper-64-Alloyed Gold Nanoparticles for Cancer Imaging: Improved Radiolabel Stability and Diagnostic Accuracy. *Angew. Chem. Int. Ed.* 2014, 53, 156-159.
8. (a) Wang, Y.; Liu, Y.; Luehmann, H.; Xia, X.; Wan, D.; Cutler, C.; Xia, Y., Radioluminescent Gold Nanocages with Controlled Radioactivity for Real-Time in Vivo Imaging. *Nano Lett.* 2013, 13, 581-585; (b) Black, K.; Wang, Y.; Luehmann, H.; X Cai; W Xing; Pang, B.; Zhao, Y.; CS Cutler; LV Wang; Y Liu; Xia, Y., Radioactive 198Au-Doped Nanostructures with Different Shapes for In Vivo Analyses of Their Biodistribution, Tumor Uptake, and Intratumoral Distribution. *ACS Nano* 2014, Apr. 25 (DOI: 10.1021/nn406258m).
9. (a) Lee, H.; Akers, W.; Edwards, W.; Liang, K.; Cheney, P.; Culver, J.; Achilefu, S., Complementary optical and nuclear imaging of caspase-3 activity using combined activatable and radio-labeled multimodality molecular probe. *Journal of Biomedical Optics* 2009, 14 (4), 040507-1; (b) Olson, E.; Jiang, T.; Aguilera, T.; Nguyen, Q.; Ellies, L.; Scadeng, M.; Tsien, R., Activatable cell penetrating peptides linked to nanoparticles as dual probes for in vivo fluorescence and MR imaging of proteases. *Proc. Natl. Acad. Sci. U.S.A.* 2010, 107 (9), 4311-4316; (c) Solomon, M.; Guo, K.; Sudlow, G.; Berezin, M.; Edwards, W.; Achilefu, S.; Akers, W., Detection of enzyme activity in orthotopic murine breast cancer by fluorescence lifetime imaging using a fluorescence resonance energy transfer-based molecular probe. *Journal of Biomedical Optics* 2011, 16 (6), 066019-1.
10. Mebrahtu, E.; Zheleznyak, A.; Hur, M.; Laforest, R.; Lapi, S., Initial characterization of a dually radiolabeled peptide for simultaneous monitoring of protein targets and enzymatic activity. *Nuclear Medicine and Biology* 2013, 40, 190-196.

Example 2. SPECT Imaging Nanoprobe for the Detection of Matrix Metalloproteinase (MMP) Activity In short the invention is the formulation of a SPECT nanoparticle probe for the detection of MMP activity. The surface of a 10 nm sized gold nanoparticle is functionalized through a thiol anchor with a peptide (DTPA-Gly-Pro-Leu-Gly-Val-Arg-Gly-Lys-Gly-Tyr-Gly-Ahx-Cys-NH$_2$—SEQ ID NO:1) that is cleaved in the presence of MMP9. The surface is also functionalized with methoxy polyethylene glycol (mPEG) to increase colloidal stability. The DTPA is radiolabeled with In-111 (or Cu-64 or potentially other radiometals) and Tyrosine is radiolabeled with I-125. MMP activity can be detected by tracking the 2 radionuclides independently, where after the peptide is cleaved, the radiometal is released from the nanoparticle.

Radiolabeling and purity was characterized with radioactive thin layer chromatography. DTPA was radiolabeled with Cu-64 and the probe was incubated with MMP9, and significantly higher activity was released compared to control, which is attributed to the peptide cleavage by MMP9. Proof of concept experiments were performed in tumor mouse models with differing MMP9 expression profiles, where preliminary evidence showed a differential uptake profile in the different types of tumors, which is evidence for detection of the peptide cleavage event by MMP9.

Detection of MMP activity is relevant to a number of biological processes and diseases, including cancer and acute lung injury.

Introduction to Example 3

Imaging agents that activate under specific conditions, for example under low pH or in the presence of an enzyme, have the ability to provide molecular, biological, and physiologically specific contrast. Most often, these activatable probes are optical in nature, wherein an emitter is linked with a quencher by a cleavable domain. This has allowed for the characterization and imaging of not just binding events, but other biological processes such as enzyme activity. Probes specific for matrix metalloproteinases (MMPs) and caspases, among others, have been reported. The activatable optical contrast agents, however, are hampered by their poor tissue penetration, which has limited their clinical translatability in many areas. Therefore, a nuclear activatable alternative is highly desired in order to fulfill the promise of this class of imaging agent. Recently, a gold nanoparticle dually-radiolabeled with $^{111}$In and $^{125}$I was synthesized in order to image activation in the presence of MMP9 in a tumor model by using two-channel SPECT imaging.

An intriguing alternative alternative radiochemistry involves the incorporation of radiometals into metal nanocrystals. $^{198}$Au has been incorporated into gold nanocrystals and used for imaging and biodistribution studies, and $^{64}$Cu has similarly been integrated into gold nanoalloys for PET imaging, which have superior radiostability to commonly used chelation chemistries. Due to its lower energy emissions compared to $^{198}$Au and $^{64}$Cu, $^{199}$Au is an isotope with better suited for SPECT.

Example 3. In Vivo Ratiometric Imaging with Activatable Multispectral Dual-Radiolabeled Metallic Nanocrystals In order to provide a nuclear alternative to optical imaging probes that can be activated in the presence of enzymes, a dual-radiolabeled gold nanoparticle SPECT probe was recently designed targeting MMP9. Multispectral imaging was performed, accumulation in tumors was observed, and evidence of activation was observed in vitro and in vivo.

One of the necessary properties of the dual-radiolabeled probes is spectral distinction between the two nuclides. While comprehensive studies have been performed incorporating $^{198}$Au into gold nanocrystals, this nuclide's 412 keV γ-emission is too energetic for optimal function in SPECT imaging. Therefore, $^{199}$Au was explored as an alternative isotope. In order to determine if the 159 keV γ emission from $^{199}$Au could be spectrally separated from the 171 and 240 keV γ emissions from $^{111}$In, a multispectral SPECT imaging experiment was performed. In this initial experiment, phantoms containing $^{199}$Au and $^{111}$In SPECT signal from phantoms containing $^{199}$Au and $^{111}$In was acquired simultaneously from two energy windows centered at 159 keV (red-yellow) and 240 keV (green). Importantly, signal was only detected in the 159 keV channel from $^{199}$Au, and $^{111}$In was detected most strongly in the 245 keV channel, with slight bleed over into the 159 keV channel due to its 171 keV emission.

Figure 12:
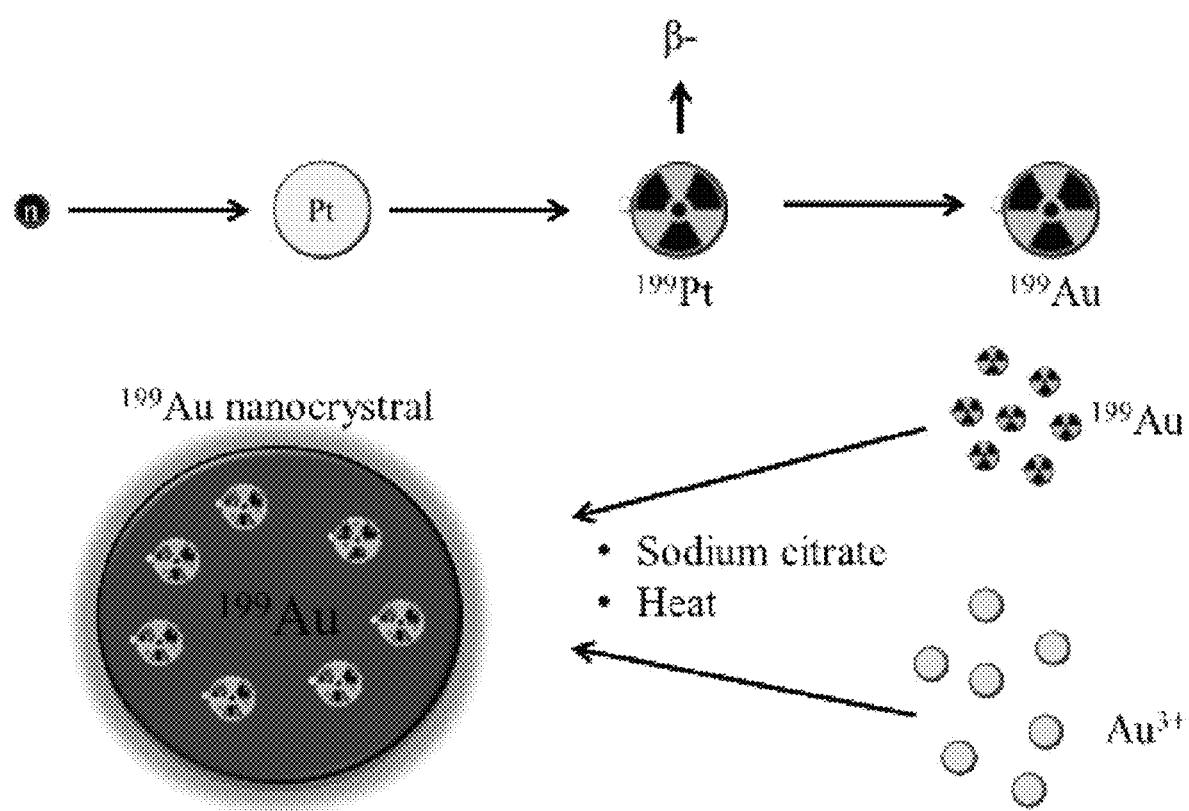
FIG. 12 depicts a schematic of the synthesis of $^{199}$Au-containing gold nanocrystals (199Au NCs).

Once the SPECT imaging properties of $^{199}$Au were validated, gold nanocrystals containing $^{199}$Au were synthesized through an aqueous reduction method adapted from that pioneered by Turkovich (FIG. 12). Citrate-$^{199}$AuNPs were synthesized according to the protocol that was established in our laboratories in which 2 ml of 0.5 mM of NaAuCl4 and 15 µl of $^{199}$Au were mixed together, heated, and stirred until the solution's temperature reached the boiling point. Then, 206 µl of 38.8 mM of sodium citrate was added with continuous heating and stirring. After a few minutes the color of the solution transformed gradually from pale yellow to wine red color, an indication of the formation of gold nanocrystals. After 10 min, the solution was stirred at room temperature for 15 min. An LSPR maximum wavelength of 525 nm was observed with UV-Vis spectroscopy. Radio thin layer chromatography (TLC) was used to measure the yield of $^{199}$Au contained in the gold nanocrystals, and confirmed that greater than 96% of $^{199}$Au was present in the nanocrystal form and there was undetectable free $^{199}$Au in the suspension.

Figure 13:
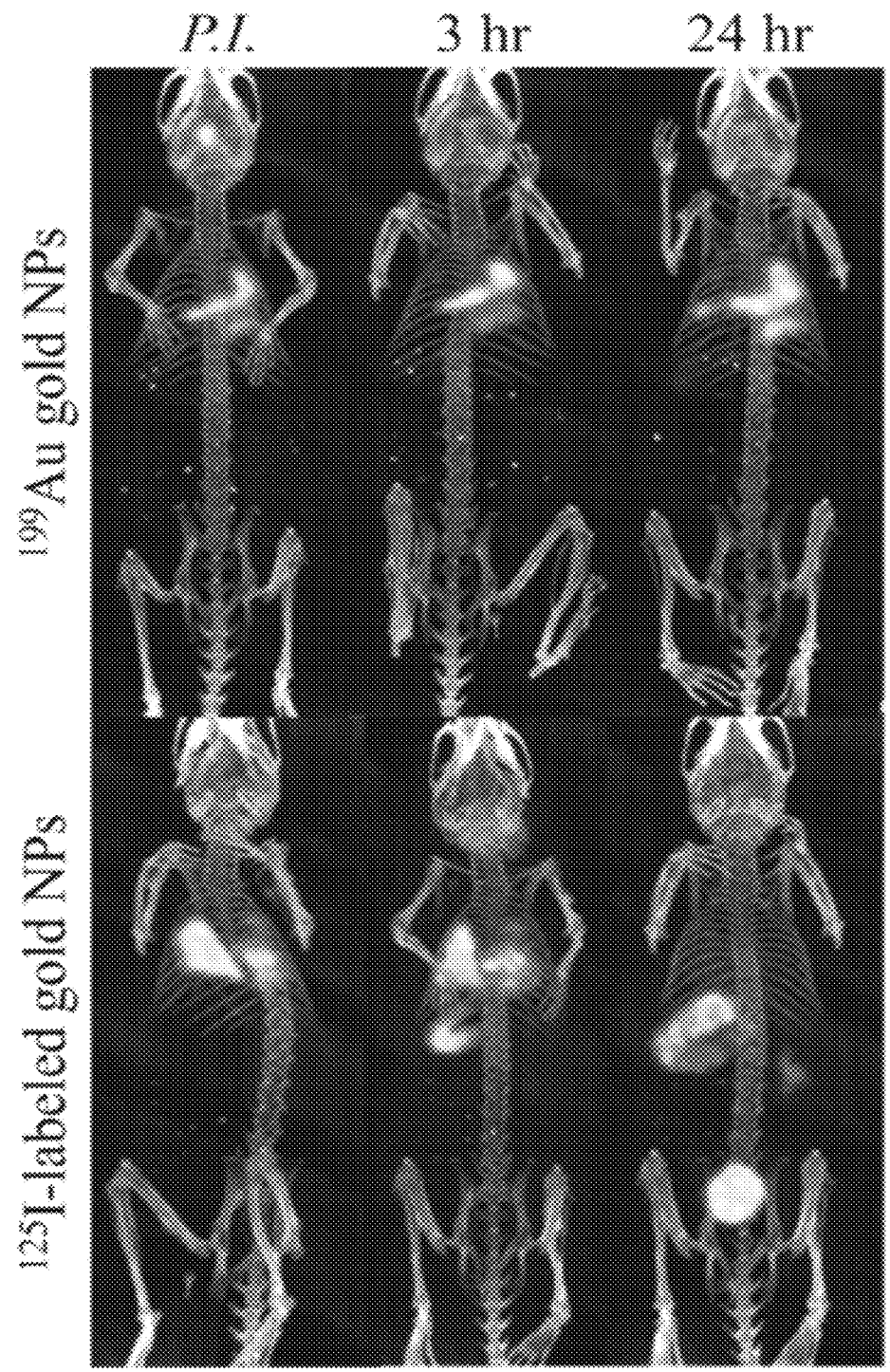
FIG. 13 depicts imaging from the longs of mice intratracheally injected with $^{199}$Au gold and $^{125}$Au-labeled gold nanoparticle constructs imaged immediately, 3 hours post-injection, and 24 hours post-injection.

To compare the $^{125}$I-labeled nanoprobe to the radioactive metal nanocrystal, two probes were synthesized: (1) a similarly pegylated $^{125}$I-labeled gold nanoparticle used in the recent study and (2) a pegylated radioactive gold nanocrystal, where the nuclide is embedded directly into a metal crystal structure that provides significantly enhanced in vivo stability. The two gold nanoparticle constructs were injected intratracheally into the lungs of mice and imaged immediately and then 3 and 24 hours later (FIG. 13). Clear differences in clearance were observed between the two probes. Whereas there was no significant decrease in uptake values of $^{199}$Au-doped nanocrystals from the lung even 24 hours after injection, a 76% decrease was observed with the $^{125}$I-labeled counterparts. These preliminary experiments provided evidence that a $^{199}$Au-doped gold nanocrystal was a viable alternative to the unstable $^{125}$I-labeled gold nanoparticles.

Figure 14:
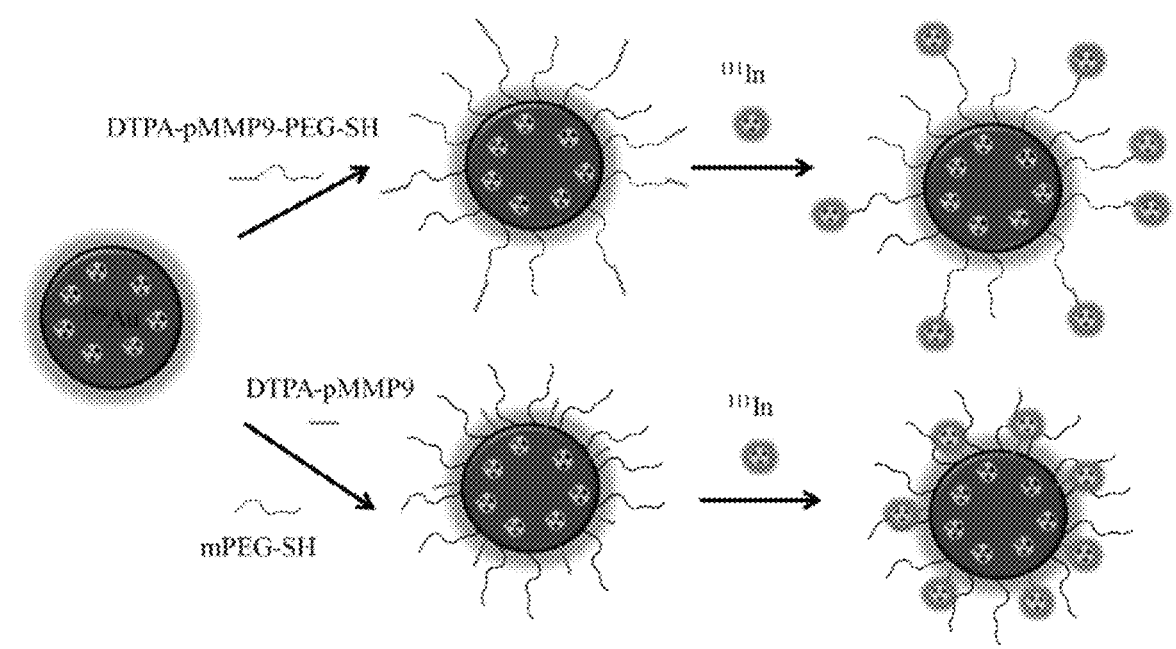
FIG. 14 depicts a schematic of $^{111}$In-labeled $^{199}$Au-doped gold nanocrystals.

Therefore, two dual radiolabeled nanoprobes were synthesized using the $^{199}$Au-doped gold nanocrystals as a core (FIG. 14). In one scheme (upper flow), the radioactive gold nanocrystals were surface functionalized with a polyethylene glycol conjugate (DTPA-pMMP9-PEG-SH). The molecule was synthesized in a step wise fashion. First, a peptide (pMMP9; SEQ ID NO:1: DTPA-Gly-Pro-Leu-Gly-Val-Arg-Gly-Lys-Gly-Tyr-Gly-Ahx-Cys-NH$_2$) was built on solid support. Once cleaved from the resin, the peptide was linked onto a PEG5000 through a DBCO-maleimide linker. Specifically, the thiol from the cysteine residue was reacted to maleimide to form a thioether bond, leaving the DBCO functional group to react to an azide on a bifunctional azide-PEG-SH. Once synthesized, the PEG conjugate contained (1) a DTPA moiety for $^{111}$In chelation, (2) a peptide cleaved specifically in the presence of MMP9, (3) a PEG5000 chain to stabilize the gold NPs in aqueous conditions, and (4) a thiol endgroup for anchorage to the gold surface. In an alternative synthetic scheme (lower flow), one based on a previous design, the $^{199}$Au-containing gold NPs were simultaneously incubated with both m PEG-SH and DTPA-pMMP9 to form a mixed surface coating. After surface functionalization, the NPs were incubated with $^{111}$In in an acidic buffer to chelate to DTPA functional groups on the outer end of the PEG, which was confirmed by radio TLC.

Figure 15:
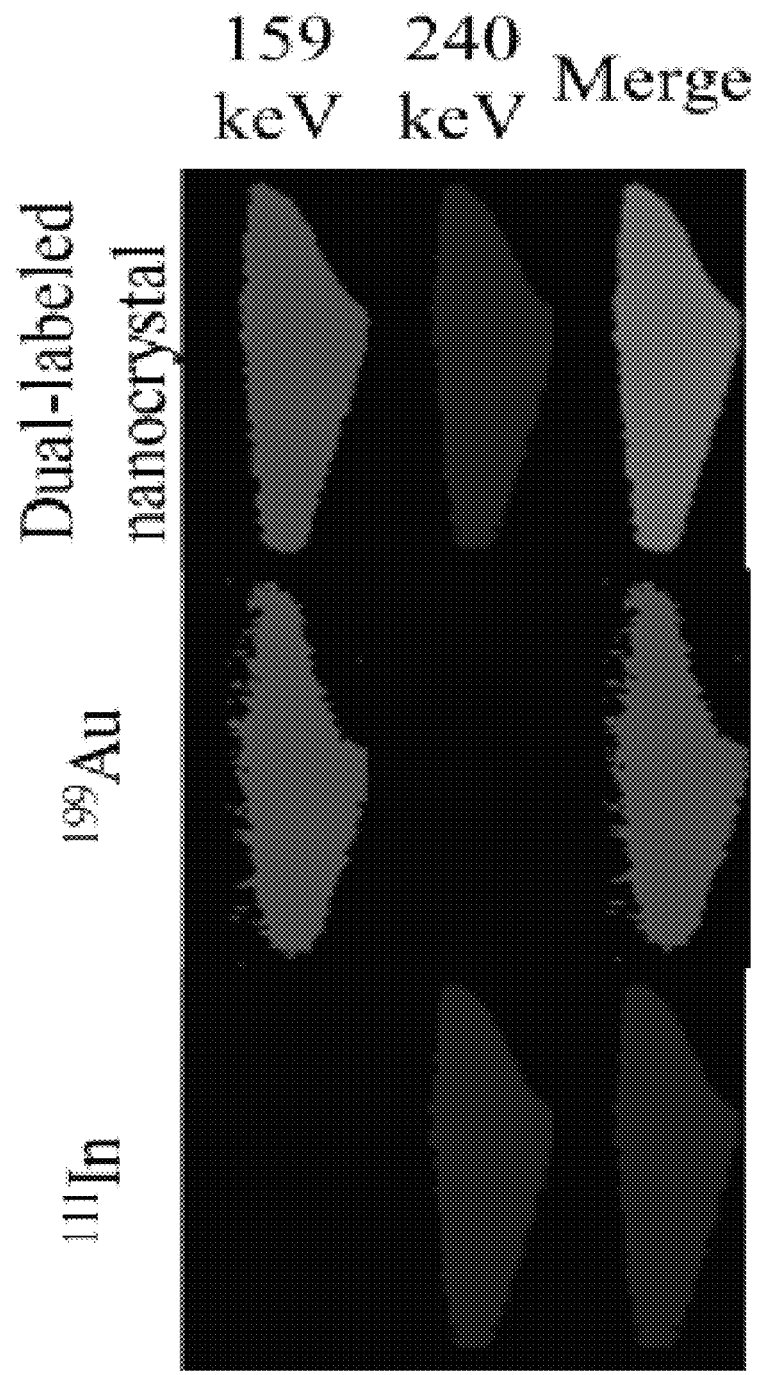
FIG. 15 depicts phantom SPECT imaging.

Aqueous solutions containing the multispectral probe and controls of the individual $^{199}$Au and $^{111}$In nuclides were imagined with single photon emission computed tomography (SPECT) using two distinct energy windows of acquisition, 159±11 keV (red) and 245±60 keV (blue) γ signal was detected from the dual-labeled metal nanocrystal in both channels, making the merged image of this solution appear purple. The $^{199}$Au control was only detected in the 159 keV channel, remaining red in the merged image. Since $^{111}$In is characterized by γ emissions at both 171 keV and 245 keV, signal was detected in both channels and thus appears purple in the merged image. One of the goals of this study was to use the 2 channels to distinctly quantify concentrations of $^{199}$Au and $^{111}$In, and since $^{111}$In provides signal in both channels, image processing was performed in order to subtract 171 keV $^{111}$In signal from the 159 keV imaging channel to make the remaining signal representative of $^{199}$Au concentration. Importantly, a simple linear relationship was observed between $^{111}$In concentration and signal detected in the 245 keV channel. Therefore an $^{111}$In concentration could be quantified from the 245 keV channel, and then a proportional amount of signal could be subtracted from the 159 keV channel to determine $^{199}$Au concentration. Once this analysis was performed, the dual-nuclide sample, the $^{199}$Au control, and the $^{111}$In control appear purple, red, and blue, respectively (FIG. 15).

Figure 16:
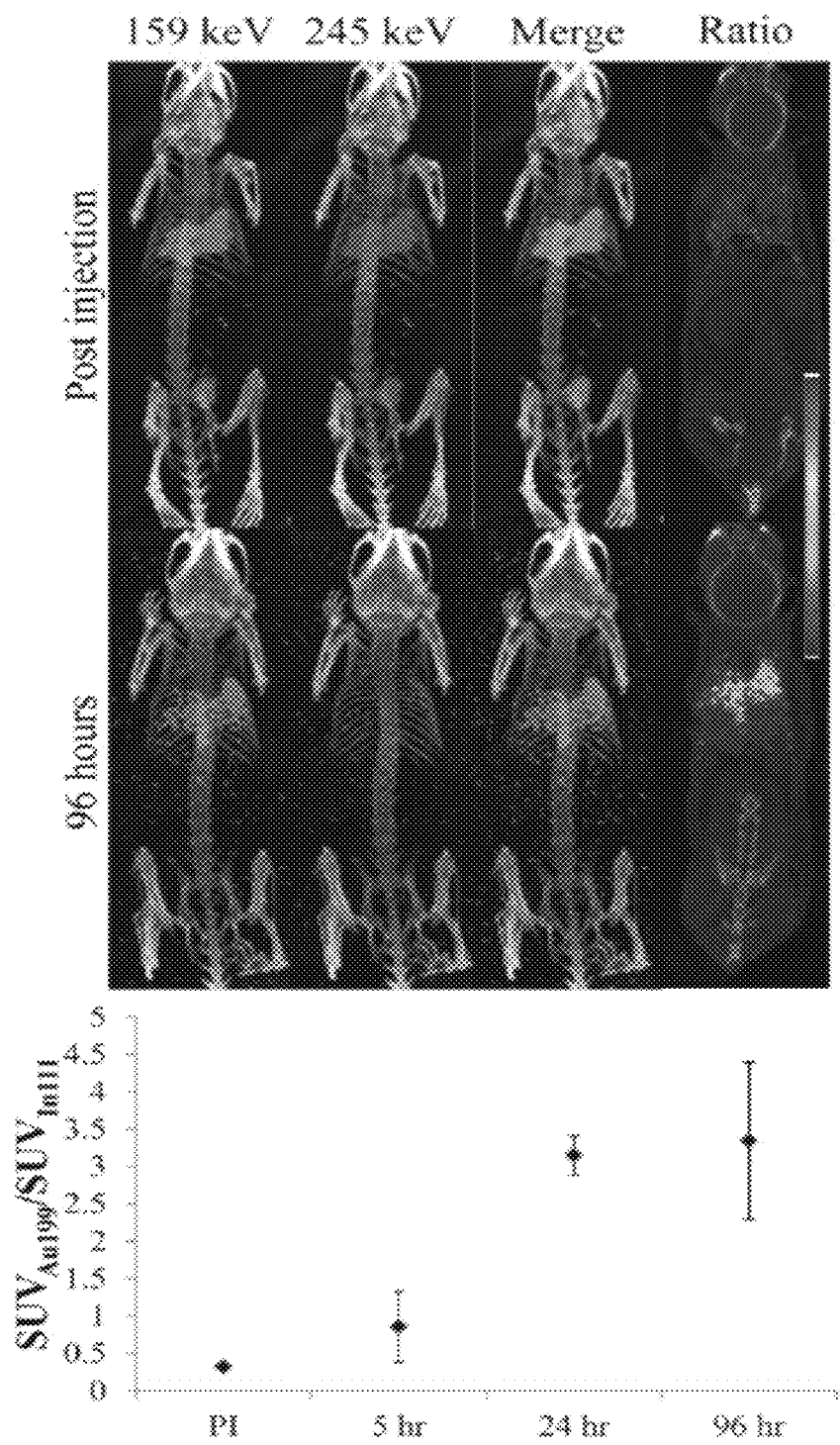
FIG. 16 depicts ratiometric lung imaging of activation in the lung immediately post-injection and 96 hours post-injection and a graph depicting standardized uptake values in the lungs.

The dual-radiolabeled nanocrystals were then explored as enzyme-activatable nuclear contrast agents. Simply, the concept involves the tethering of 2 distinct nuclear emitters which are cleaved from one another in the presence of an enzyme, leading to their spatial separation over time. In this instance, a $^{199}$Au-containing gold NP is separated from $^{111}$In with a peptide cleaved in the presence of MMP9. To explore the use of the multispectral dual-radiolabeled metallic nanocrystals for in vivo ratiometric imaging, suspensions were intratracheally injected into the lungs of mice and imaged over a 96 hour time period (FIG. 16). Standardized uptake values (SUVs) in lungs were quantified in both the 159 keV and 245 keV channels, and a clear change in ratiometric signal was observed over time. Immediately upon injection, strong signal from both of the imaging channels was detected, giving a [SUV]Au199/[SUV]In$^{111}$ ratio of 0.32±0.04 (upper panels), represented by the purple lungs in the merged window image, which increased to a ratio of 0.85±0.47 5 hours later. By 24 hours, the ratio had increased to 3.15±0.26, and remained at 3.34±1.05 96 hours after injection (lower panels), represented by the mostly red lungs in the merged energy window.

Figure 17:
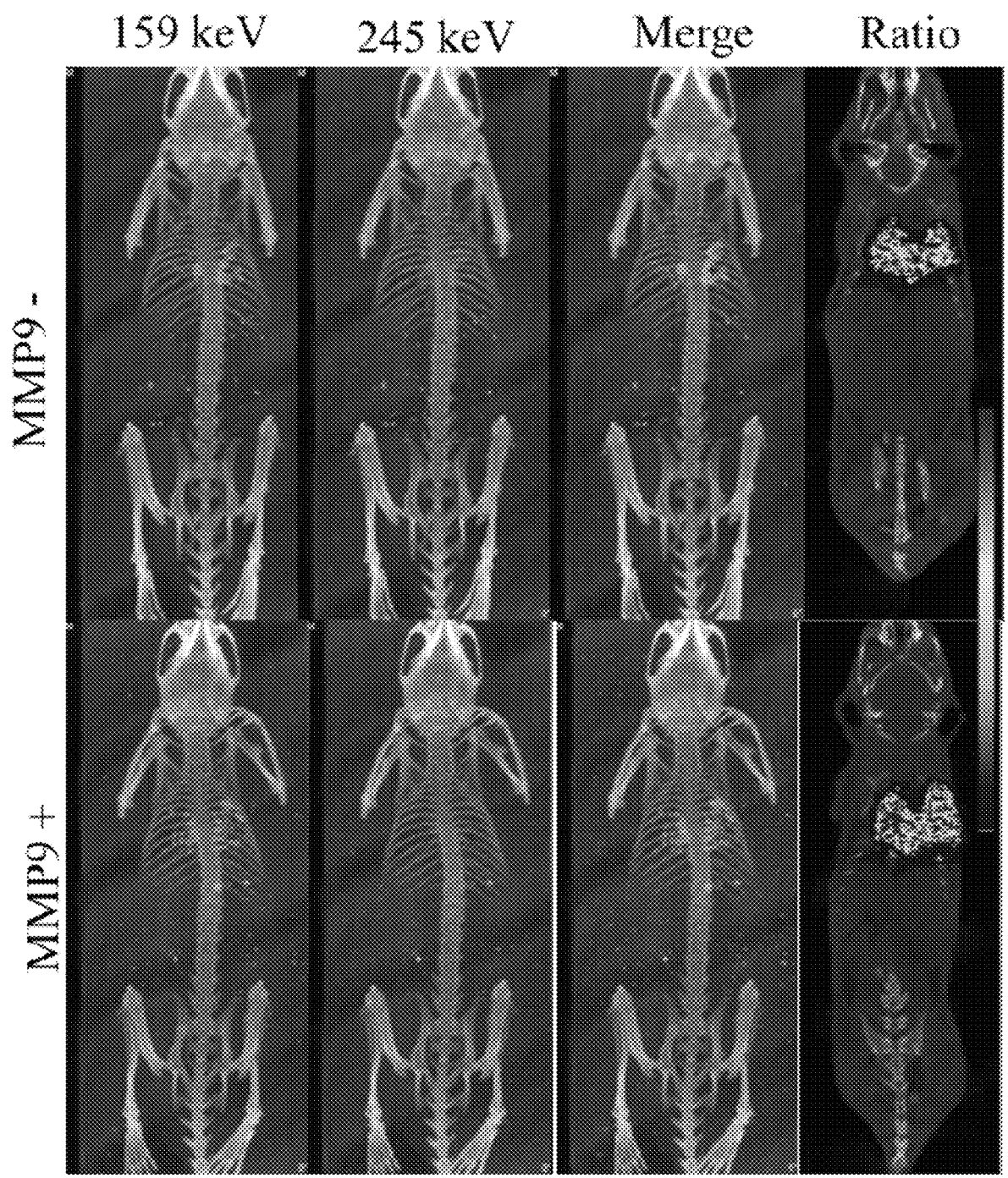
FIG. 17 depicts ratiometric imaging of the lungs of mice injected with dual-labeled nanocrystals that had been incubated with MMP9.

To interrogate the specificity of the change in ratiometric signal, an experiment was performed wherein the dual-labeled nanocrystal was incubated with MMP9 and then injected into the lung of mice (FIG. 17). Importantly, clear differences were observed between samples that had been incubated with MMP9 compared to those that had not. More specifically, the [SUV]Au$^{199}$/[SUV]In$^{111}$ was significantly enhanced in the lungs of mice injected with pre-incubated probes at all imaging time points compared to control. Whereas the average pixel ratio in the MMP9 lung was 4.3 directly upon injection, the control had a value of 2.5. The contrast dramatically increased 2 hours later, where the MMP9 lung ratio increased to 8.6 but the control remained steady at 1.8. Both conditions moderately increased ratio (associated with preferential clearance of $^{111}$1 n compared to $^{199}$Au) over the course of 24 hours, represented in FIG. 17 by a preferential loss of 245 keV emission (blue) and an increased ratio intensity in the MMP9+ lungs compared to controls. 24 hours after injection, the MMP9 lung reached an average ratio value of 21.3 compared to a control ratio value of 9.9 (FIG. 17, final panel). The lungs were excised and gamma emission spectra were acquired in a Ge detector, and a 34% enhancement in the 159 keV/245 keV ratio was observed in MMP9 lungs compared to control (data not shown).

Figure 18:
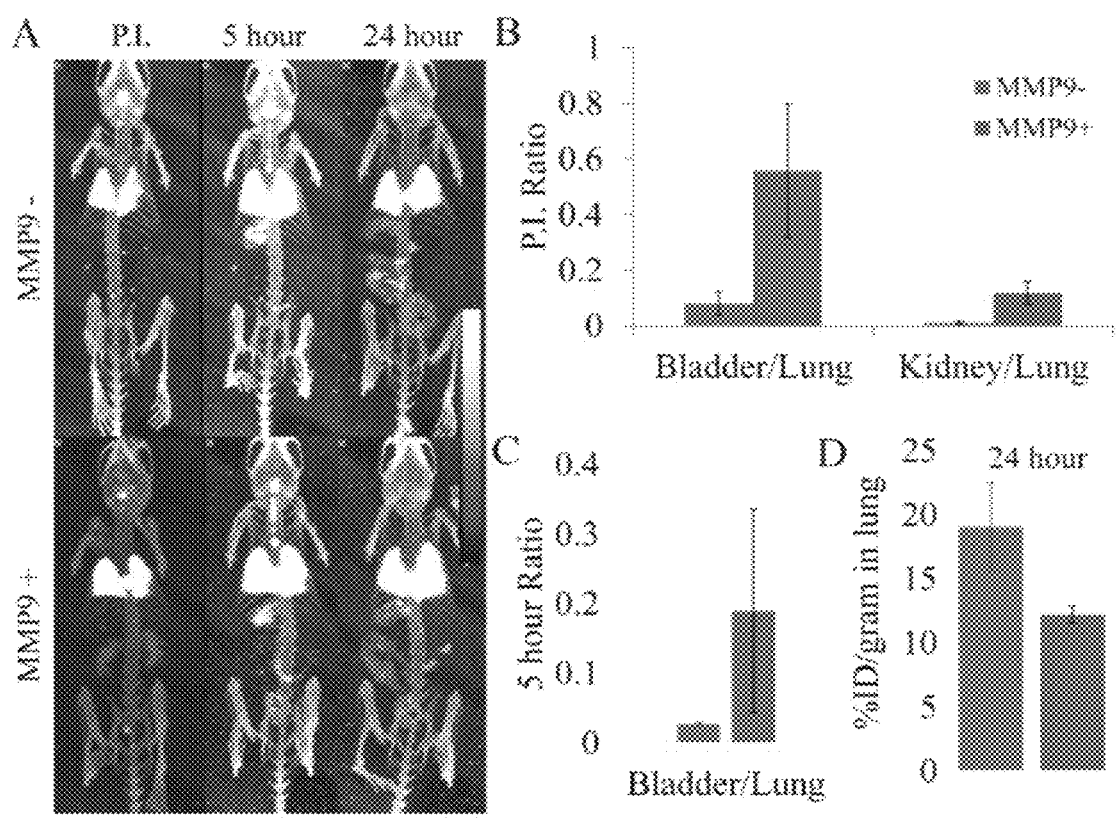
FIG. 18 depicts activation by MMP9 in the kidney, lung, and bladder by ratiometric imaging of mice immediately post-injection, 5 hours post-injection, and 24 hours post-injection (A), a graph quantifying the post-injection ratios (B), a graph quantifying ratios 5 hours post-injection (C), and a graph quantifying ratios 24 hours post-injection (D).

To further validate the specificity of the activation, an identical experiment as the one just described was performed with an $^{111}$In-labeled non-radioactive gold nanoparticle probe, similar to a radioactive nanoparticle previously reported. An initial in vitro validation was performed; when incubated with MMP9 for 48 hours, 48% $^{111}$In was cleaved from the nanoparticle compared to only 16% without MMP9. With this singly-labeled probe, an alternative in vivo ratiometric imaging approach was performed (FIG. 18A). Rather than compare the ratio between two gamma energy channels, uptake intensity ratios between the lungs and kidneys or bladder were quantified. Importantly, clear distinctions were observed between the MMP9 and control groups. Immediately upon injection, uptake in the kidneys and bladders of the mice in the MMP9 group was significantly higher than controls, providing enhanced kidney/lung and bladder/lung ratios of 0.12±0.04 and 0.56±0.24, respectively, compared to control ratio values of 0.01±0.004 and 0.08±0.04 (FIG. 18B). Differences were also observed 5 hours after injection (FIG. 18C), where the bladder/lung ratio remained elevated in the MMP9-incubated condition (0.19±0.15) compared to the control (0.03±0.003). 24 hours after injection, along with mucocilliary clearance from the lung to the stomach and gastrointestinal system being evident in both groups, overall $^{111}$In clearance from the lung was enhanced in the MMP9 group compared to control, both by SPECT uptake quantification (FIG. 18D) and ex vivo gamma counting.

The multispectral imaging also provided information about other physiological parameters. For example evidence for mucociliary clearance was observed in all of the mice. In one particular example, 5 hours after injection, signal co-registered from both energy windows was observed in the mouth of mice and interestingly, 159 keV signal was preferentially detected in the stomach compared to the 245 keV signal, and in contrast 245 keV signal was preferentially located in the intestines, implying cleavage of $^{111}$In from the $^{199}$Au-doped nanocrystal in the stomach after mucociliary clearance from the lung.

Discussion for Example 3

This study reports on the synthesis, characterization, and application of a nuclear activatable imaging probe that targets MMP9. Multiple chemistries were necessary in order to form the agent, $^{111}$In-DTPA chelation, gold-thiol bonds, and metallic bonding provided the necessary stability in order to detect specific cleavage in the presence of MMP9.

The γ emission properties of the two isotopes were also sufficient to provide two-channel ratiometric imaging in mice lung. The 245 keV channel detected only the 240 keV emission from $^{111}$In, whereas the 159 keV channel detected the 159 keV emission for $^{199}$Au as well as the 171 keV and downscatter from $^{111}$In. While there was significant "bleed over" $^{111}$In signal into the lower energy window, it could be corrected based on the pure $^{111}$In 245 keV channel. With this simple correction, ratios could be quantified at every pixel in the 3D SPECT image and representative on an intensity scale (FIG. 16 and FIG. 17). This allowed for in vivo ratiometric imaging of the lung to interrogate activation by MMP9.

Ratiometric organ imaging was also performed and also provided quantitative evidence for activation of the probe by MMP9.

Both 2 channel ratiometric imaging and organ ratiometric imaging provided clear evidence of probe activation by MMP9.

This value of Amax of radioactive-Citrate gold nanoparticles was longer than Amax of non-radioactive gold nanoparticles by only 5 nm. The results of Graber et al. (1995) showed that the non-radioactive citrate-gold nanoparticles have have λmax of 520 nm and have core size of 13 nm. In the present work, radioactive-Citrate $^{199}$AuNPs have Amax of 525 nm. This result indicates that the size of radioactive gold nanoparticles is still less than 15 nm.

The $^{199}$Au-doped nanocrystals have promise in more than lung administration applications. As a proof of concept experiment, a suspension was injected via the tail vein of mice.

Methods for Example 3

Materials and Methods for Producing Radioactive Citrate $^{199}$Au Nanoparticles Chemicals All chemicals were research grade unless otherwise stated. Sodium citrate and Ethyl Acetate were obtained from Fisher Scientific Company, Sodium tetrachloroaurate (NaAuCl4) (99.999%) was purchased from Sigma Aldrich Company. Enriched 95.83% Platinum-198 metal powder used to produce $^{199}$Au was obtained from Trace Sciences (Ontario, Canada).

Measurements

The absorption measurement for nanoparticles was performed on an. The yield of radioactive gold nanoparticles was measured using cellulose paper developed in methanol containing two drops of concentrated HCl. The TLCs were measured via a carrier-free $^{199}$Au production. Enriched $^{198}$Pt metal powder targets encapsulated in quartz ampoules were irradiated with neutrons to produce $^{199}$Pt according to the nuclear equation Pt-198(n, γ) Pt-199 which rapidly decays by β-emission to $^{199}$Au. Specifically, 1.76 mg of enriched Pt metal powder was irradiated for 152.11 hr in the high flux position at the Missouri University Research Reactor (MURR). Initial activity of Pt/$^{199}$Au was 115.6 mCi. Then the material was dissolved in 400 µL of aqua regia. To this 400 µL of 0.05M HCl was added twice and heated to azeotrope off nitric acid. The final volume was 400 µL of 3M HCl with a final activity of 104.3 mCi.

Pt/Au-199 separation was performed by liquid-liquid extraction. 400 µL of Pt/$^{199}$Au in 3M HCl were mixed with 400 µL of ethyl acetate and vortexed for 1 minute. After allowing sitting for 5 minutes at room temperature, the layers were separated. The top layer contained 76 mCi of carrier-free $^{199}$Au in ethyl acetate. Quality control was performed by analyzing a small aliquot of the separated $^{199}$Au to 10 ml of 0.05M HCl with a High Purity Germanium spectrometer with Genie-2000 Procount software. The $^{199}$Au in ethyl acetate was dried to remove the ethyl acetate. Next 400 µL of 0.05 M HCl was added 2 times and brought to near dryness. The material was brought to a final volume of 60 µL with H2O and a total activity of 32 mCi. The radionuclidic purity of non-carrier added $^{199}$Au was measured using a High Purity Germanium detector with Genie-2000 Procount software.

Synthesis of Radioactive Citrate-$^{199}$AuNPs

Gold nanocrystals containing $^{199}$Au were synthesized using a citrate reduction method. 2 ml of 0.5 mM NaAuCl4 was added to a V-bottom vial, followed by the addition of 15 µl of $^{199}$Au (8.5 mCi). The mass of $^{199}$Au is negligible and the volume of $^{199}$Au that is mixed with NaAuCl4 is based on the required activity of the final solution of nanoparticles. Next, the vial containing the solution of NaAuCl4 and $^{199}$Au was stirred vigorously and continuously and brought to a boil (99-100° C.). When the solution's temperature reached the boiling point, 206 µl of 38.8 mM sodium citrate was added to the solution. This resulted in a gradual color change from pale yellow to greyish-blue to the expected wine red color. The boiling and stirring was continued for 10 minutes. The solution was then removed from heat and stirring was continued at room temperature for an additional 15 minutes. The final color was wine red which indicates the formation of gold nanocrystals. The surface plasmon resonance of the resulting solution of radioactive gold nanocrystals was characterized by UV-Vis extinction spectroscopy using an Ocean Optics USB 2000. Radioactive thin layer chromatography (TLC) was performed to estimate the yield of radioactive $^{199}$Au gold nanocrystals. 1 µl of nanoparticle suspension was deposited onto cellulose paper. After 5 min, the TLC plate was placed vertically in a developing chamber that contained 4 ml of methanol and two drops of concentrated HCL. After developing the paper was removed from the chamber and left to dry for five minutes, and then measured on a Bio Scan AR-2000 radio-chromatographer to determine the radiochemical yield.

Pegylation.

In order to pegylate the surface of $^{199}$Au-doped gold nanocrystals, 2.5 mg mPEG-SH (MW5000) was dissolved in 1 mL of ultrapure water, added to the 2 mL $^{199}$Au-doped gold nanocrystal suspension, which was mixed overnight. Suspensions were centrifuged at 14.5 k g for 1.5 hours and the supernatant was removed.

$^{125}$I-Labeled Gold Nanoparticle Synthesis.

Labeling was performed in a similar manner previously described. Briefly, 3 mL of 10 nm diameter citrate-stabilized gold nanoparticle suspension (Sigma Aldrich; 6×10$^{12}$ particles/mL) was centrifuged at 20 k g force for 1.5 hours, and supernatant was removed. 300 µL of 0.5 mg/ml PEG-pMMP9 was added to the suspension and mixed overnight, centrifuged for 1.5 hours at 20 k g, and the supernatant was decanted. 50 µL PBS was added and suspensions was transferred to an iodogen tube. 6 µL $^{125}$I (636 µCi) was added and the sample was periodically shaken gently for 1 hour. Radiochemical purity was confirmed by TLC.

Peptide (DTPA-pMMP9) Synthesis.

Standard Fmoc solid phase synthetic protocols were used to synthesize the peptide containing the MMP9 substrate, tyrosine residue, DTPA chelator, and cysteine anchor (SEQ ID NO:1: DTPA-Gly-Pro-Leu-Gly-Val-Arg-Gly-Lys-Gly-Tyr-Gly-Ahx-Cys-NH$_2$). Briefly, amino acids were successively loaded onto rink amide resin (0.66 mmol/g resin) using a CEM Discover Liberty Microwave Peptide Synthesizer. The peptide was purified with a Gilson UV/Vis-152 high performance liquid chromatographer (HPLC) using a C18 preparation column. Molecular weight of 1648 g/mol was confirmed with matrix-assisted laser desorption ionization mass spectrometry (MALDI-MS).

Dual-Labeled Probe Synthesis.

1.2 mg of the DTPA-pMMP9-PEG-SH was dissolved in 1 mL ultrapure water, and then mixed with the 2 mL $^{199}$Au gold NP suspension (6 mCi) overnight. To purify unbound PEG-pMMP9 and other precursors, the NP suspension was centrifuged for 15 minutes at g force and supernatant was removed, leaving a 75 µL pellet containing 2.65 mCi. 200 µL 0.1 M NH4OAc (pH 5.5) was added to the pellet, followed by 4.88 µL $^{111}$InCl (1.17 mCi), and the sample was incubated at 25° C. for 1.5 hours. Radiochemical purity was quantified by thin layer chromatography (TLC).

Another dual-radiolabeled probe was synthesized from the $^{199}$Au-containing gold nanocrystals that uses a similar design to a nanoparticle SPECT probe recently reported. Briefly, 2.2 mg mPEG-SH (MW=5000) and 1.0 mg of the DTPA-pMMP9 peptide were dissolved in 1 mL ultrapure water and immediately added to the 2 mL radioactive gold nanocrystal suspension, vortexed vigorously, and then mixed at 25° C. for 8 hours. The suspension was centrifuged for 30 minutes at g-force, and the supernatant was removed. An aliquot containing 194 µCi 199Au was dissolved in 100 µL of 0.1 M NH4OAc buffer (pH 5.5), and then 100 µCi $^{111}$InCl (0.31 µL) was added to the suspension, vortexed, and shaken at 45° C. for 75 minutes.

Phantom Imaging.

Three distinct aqueous samples were imaged: (1) the dual labeled probe described above, diluted to 0.10 mCi $^{111}$In and 0.23 mCi $^{199}$Au in 1 mL, (2) 0.25 mCi $^{199}$Au gold NPs suspended in 1 mL, and (3) 0.077 mCi $^{111}$InCl in 1 mL. Tubes were imaged with 24 projection scans (60 seconds per scan) in a NanoSPECT/CT (Bioscan, Inc., Washington, D.C.). Two energy windows were simultaneously acquired in order to detect both $^{111}$In and $^{199}$Au; 240±60 keV was monitored to track $^{111}$In, and 159±11 keV was used to track $^{199}$Au.

In Vivo SPECT/CT Imaging.

The Animal Studies Committee of the Washington University School of Medicine approved these studies. C57BL/6J mice were obtained from Jackson Laboratory (Bar Harbor, Me.) and housed in a barrier facility. 50 µL of either $^{125}$I-labeled gold NPs (500 µCi), $^{199}$Au-containing gold NP (370 µCi), or dual radiolabeled gold nanoparticle suspension (~0.18 mCi $^{111}$In and 0.41 mCi $^{199}$Au) was injected intratracheally into mouse lungs in two 25 μL doses one minute apart. SPECT/CT imaging was performed on the NanoSPECT/CT. As described in the SPECT phantom study methods above, two energy windows centered at 240 keV and 159 keV were simultaneously tracked in order to detect both $^{111}$In and $^{199}$Au, respectively. 24 projection scans (60 seconds per scan) were performed immediately after injection, as well as 5 hours, 24 hours, and 96 hours later. Lung standardized uptake values (SUVs) were quantified from SPECT/CT images using Inveon Research Workspace software (Siemans).

MMP9 Experiment.

The dual-radiolabeled nanocrystal suspension was separated into 50 μL samples containing 20 ng MMP9 and incubated at 37° C. for 9 hours (along with control that was incubated without MMP9). 50 μL (~80 μCi $^{199}$Au and 40 μCi $^{111}$In) was then intratracheally injected into C57 Black6 mice and two-channel SPECT imaging was performed as described above. In another experiment, a similar protocol was performed with the non-radioactive gold NP core functionalized with an $^{111}$In-labeled, MMP9-cleavable peptide. Briefly, 10 mL of 10 nm diameter gold nanoparticles (Sigma Aldrich) was centrifuged at 10 k g-force for 70 minutes, supernatant was removed, the pellet was resuspended in 1 mL of ultrapure water containing 2.2 mg mPEG-SH (MW=5000) and 1.0 mg pMMP9 peptide, and shaken overnight. Suspension was again centrifuged at 10 k g-force, supernatant removed, and the pellet was resuspended in 500 μL 0.1 M NH4OAc buffer (pH 5.5). Then 15 μL $^{111}$InCl (5.23 mCi) was added and shaken at 45° C. for 90 minutes. Suspension was centrifuged at 10 k g-force for 90 minutes, supernatant removed, and the pellet containing 2.96 mCi was resuspended in 500 μL buffer. 50 μL aliquots with or without 10 ng MMP9 were prepared and shaken at 37° C. for 16 hours. 50 μL (~230 μCi $^{111}$In) was then intratracheally injected into C57 Black6 mice (n=4/group) and SPECT imaging was performed using the 245 keV channel immediately upon injection and 5 and 24 hours later.

Introduction to Examples 4-10

There are many molecular processes involved in cancer progression. The development of molecular therapies and imaging agents targeted to distinct pathological pathways has raised hope for early cancer detection and individualized therapy. An important biomarker of cancer is the diagnostic and prognostic family of proteases [1]. Although they play key roles in normal human physiology, their aberrant expression in cancer results in many undesirable effects such as an increase in tumor proliferation, metastasis, and resistance to therapy. As a result, new targeted therapies have been developed for specifically inhibiting these enzymes in cancer patients. A particularly interesting biochemical event is the migration of some proteases to unusual extracellular or intracellular spaces under pathological conditions, where they exert their cancer-supporting roles [2,3]. In this regard, a combination of quantitative detection of protein expression, localization, and functional status is required for accurate cancer diagnosis and assessment of response to therapy.

Clinically, positron emission tomography (PET) and single photon emission tomography (SPECT) are the molecular imaging techniques of choice because of their high sensitivity and whole-body quantitative imaging capabilities [4]. Elegant methods have been developed to improve in vivo detection sensitivity of predictive enzymes by PET, including the use of [$^{18}$F]fluorothymidine to report cell proliferation via the activity of thymidine kinase-1 [5]. Despite the unique advantages of these nuclear imaging methods, their applications in molecular imaging have been confined to receptor-targeted imaging of cancer [4] or indirect reporting of the functional status of proteases in vivo by use of radiolabeled inhibitors [6]. Currently, there are no nuclear imaging agents for assessing the functional status of intracellular proteases in vivo.

Unlike PET, where all annihilation photons detected have the same energy (511 keV), which precludes simultaneous discrimination of multiple PET radionuclides from the same tracer, SPECT has multiradionuclide-resolving power. This is because the gamma cameras used in SPECT can acquire projection data simultaneously from two or more radionuclides in separate energy windows with resolution exceeding that of micro-PET [7]. In addition to differences in the emission energies, radionuclides amenable for SPECT imaging have sufficiently long half-lives for timely transportation, and can be produced on site via generators. The long half-lives of commonly used SPECT radionuclides, such as $^{99m}$Tc ($t_{1/2}$, 6.02 h), $^{123}$I ($t_{1/2}$, 13.2 h), $^{125}$I ($t_{1/2}$, 59.4 days), and $^{111}$In ($t_{1/2}$, 2.8 days), make them suitable for incorporation into slow clearing biomolecules such as peptide conjugates, antibodies, and nanoparticles [8]. This compatibility of the biological half-life of the bioconjugates with the radioactive half-life of the elements results in improved signal to background ratios. Conceptually, radio-labeling a protease substrate with two SPECT compatible radioisotopes that emit gamma rays at different energies could provide a new approach for molecular imaging of protease activities via ratiometric SPECT imaging. For this approach to be successful, gamma ray(s) of the chosen nuclides should have minimal overlapping signal in the acceptance energy windows to minimize "crosstalk." For practical reasons, this is not always achievable, leading to the use of radionuclides with significant crosstalk that must be removed in a quantifiable and reproducible manner. Another immediate challenge is to ensure the dual radio-labeling of a single substrate for ratio-SPECT imaging. In the proposed strategy, the selective hydrolysis of an amide bond by the targeted protease will result in the trapping of one radionuclide in cells, while the other radionuclide is effluxed.

Based on these considerations, we have developed a molecular framework for developing and using dual radionuclide-labeled SPECT imaging agents for the molecular imaging of aberrant intracellular or extracellular proteases. Determining therapeutic response can help identify nonresponders at early time points, giving an opportunity to apply an alternative and potentially more effective treatment [9]. In this study, we demonstrated the application of the method by targeting intracellular executioner caspases responsible for induction of apoptosis, and thus are useful for monitoring the early response of tumors to treatment [10,11]. Two caspase-3 cleavable peptides were radiolabeled with different SPECT radionuclides and evaluated in vitro and in vivo with single or dual SPECT isotopes, $^{125}$I with $^{99m}$Tc or $^{111}$In. Acquisition parameters for small animal NanoSPECT imaging were developed for real-time dual-isotope SPECT image analysis. Results demonstrate the potential of using multiradionuclide-resolving power of clinically useful SPECT for noninvasively monitoring treatment response.

Figure 19:
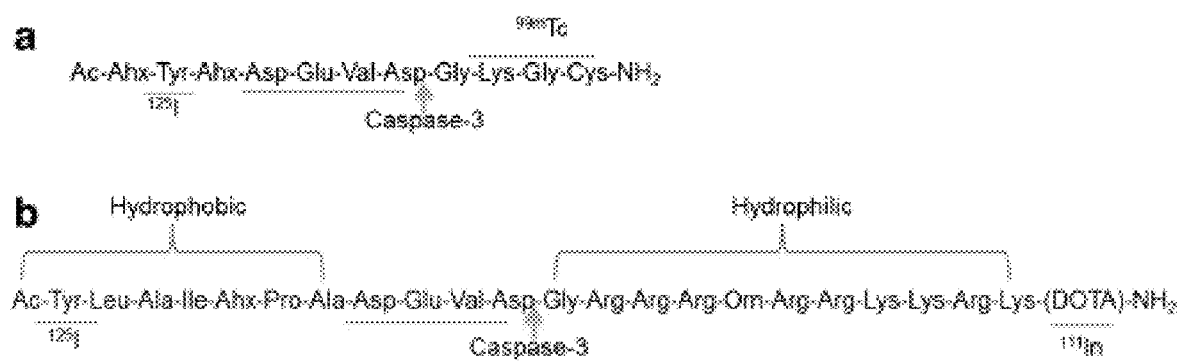
FIG. 19 depicts structures of LS370 (SEQ ID NO:5) (a) and LS734 (SEQ ID NO:6) (b).

Example 4. Synthesis of Caspase-3 Containing Peptide Bio-Molecules for Imaging Apoptosis The primary consideration of the molecular design is to ensure that each molecule can be labeled with two energetically different SPECT radionuclides. Thus, the basic structural framework consists of a peptide substrate for the target protease and reactive motifs to selectively incorporate the radionuclides at opposite ends of the peptides. Cleavage of the peptide substrate will alter the biodistribution profiles of the ensuing fragments. By determining the kinetics of each radiative fragment following cleavage, a ratiometric SPECT technique can be developed to report the activity of target enzymes. In this study, we designed molecular imaging probes that are sensitive to the activity of the executioner caspases (caspase-3/7). These caspases, which are upregulated in the early phase of caspase-mediated cell death, recognize and cleave the tetrapeptide motif, DEVD (SEQ ID NO:2—aspartic acid-glutamic acid-valine-aspartic acid). To illustrate the concept, we designed two molecular imaging agents, LS370 (SEQ ID NO:5) and LS734 (SEQ ID NO:6) (FIG. 19), containing this motif. Both peptides were prepared by modular solid-phase synthesis. LS370, which contains only nine amino acid peptide sequence, is a simple model of the dual radiolabeled molecular imaging agent for ratiometric SPECT. It consists of DEVD (SEQ ID NO:2) peptide flanked by a tyrosine group for $^{125}$I labeling and -Lys-Gly-Cys-group for $^{99m}$Tc labeling. The more elaborate analogue, LS734, was designed to generate disparate molecular features upon enzyme cleavage to facilitate ratiometric SPECT data analysis. LS734 comprises 21 amino acids and consists of three functional components: (a) a cell internalizing (positively charged) amino acid sequence capable of accommodating stable $^{111}$In [Gly-Arg-Arg-Arg-Orn-Arg-Arg-Lys-Lys-Arg-Lys-(DOTA)-NH$_2$—SEQ ID NO:3], (b) a caspase-3 cleavable DEVD (SEQ ID NO:2) peptide sequence, and (c) a hydrophobic peptide sequence containing Tyr group for labeling with $^{125}$I (Ac-Tyr-Leu-Ala-Ile-Ahx-Pro-Ala—SEQ ID NO:4). All the peptides were obtained in high purity (>95%) by high-performance liquid chromatography and characterized by liquid chromatography-mass spectrometry. Upon cleavage, LS734 is expected to dissociate into $^{125}$I-labeled hydrophobic and $^{111}$In-labeled hydrophilic fragments, with distinct biodistribution profiles. Conceptually, the high disparity between the hydrophobic and the positively charged hydrophilic peptide fragments ensures a relatively higher efflux rate of one of the fragments from cells undergoing caspase-mediated apoptosis than the other component. Optimization of the biological transport profiles can be achieved by incorporating molecules that facilitate active efflux of one fragment.

Example 5. Radiochemistry

Figure 25:
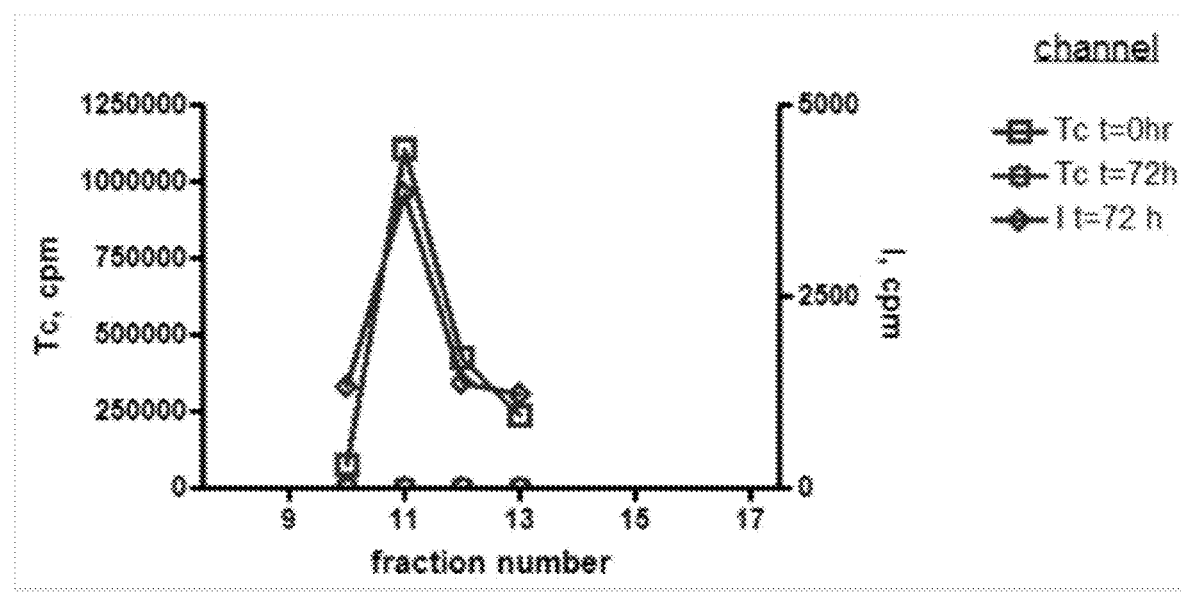
FIG. 25 depicts decay counts of $^{125}$I and $^{99m}$Tc in LS370.

The achieved specific activities were as follows: [$^{125}$I]LS370, 40-50×10$^6$ MBq/mmol; [$^{125}$I]LS734, 6-10×10$^6$ MBq/mmol; and [$^{111}$In]LS734, 12×10$^6$ MBq/mmol. The specific activity of [$^{125}$I]-[$^{111}$In]LS734 was 3×10$^6$ MBq/mmol. We also determined the specific activity of [$^{99m}$Tc]LS370 from the purified [$^{125}$I]-[$^{99m}$Tc]LS370. Based on a specific activity of 50×10$^6$ MBq/mmol of $^{125}$I-LS370, the specific activity of $^{99m}$Tc in [$^{125}$I]-[$^{99m}$Tc]LS370 was calculated. After 72 h of decay, 0.02% of $^{99m}$Tc remained, but this fraction did not have a significant impact on the $^{125}$I n counting window (15-75 keV). Based on the sum of the counts per minute (CPM) from fractions 10-12 and the counting efficiency (0.679 CPM/DPM; see FIG. 25), the calculated specific activity of $^{99m}$Tc in [$^{125}$I]-[$^{99m}$Tc]LS370 was 17×10$^{10}$ MBq/mmol. This value is in good agreement with the literature reported maximum specific activity of $^{99m}$Tc, which is ~20×10$^{10}$ MBq/mmol [15].

Example 6. Dual [$^{125}$I]-[$^{111}$In]Nuclide SPECT Imaging Phantom

Figure 20:
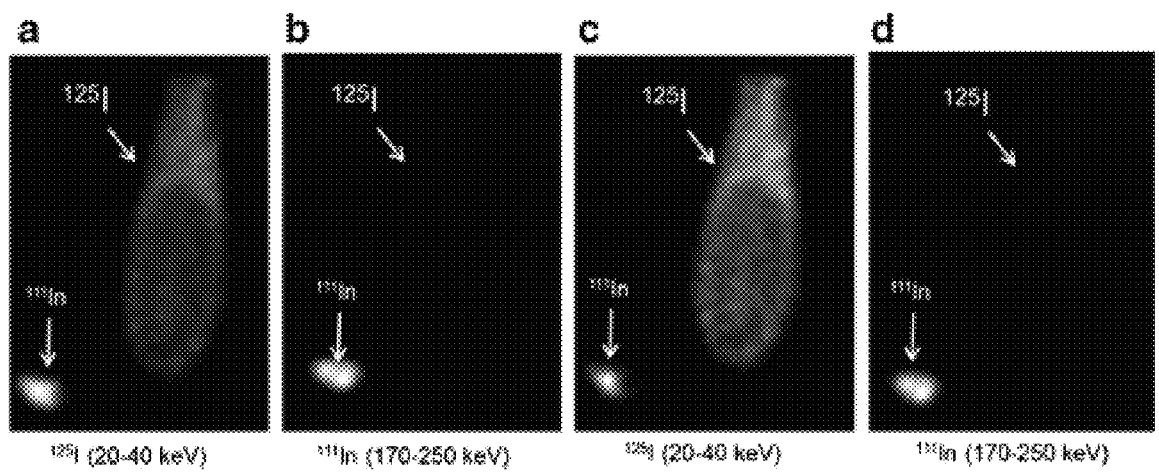
FIG. 20 depicts images of vials containing either $^{125}$I or $^{111}$In scanned with SPECT/CT. Raw (a,b) and unmixed (c,d) images were constructed from signals collected in two energy windows (20-40 keV and 170-250 keV).

The data were acquired in two energy windows, one at 30 keV of $^{125}$I and a second encompassing the two high energy peaks of $^{111}$In (171 and 245 keV). The consequence of this dual-labeling strategy is that $^{125}$I measurements are contaminated with $^{111}$In activity due to overlap in the X-ray energy and contamination from down scatter. Based on the unmixing strategy described in Methods for Examples 4-10, efficiency and cross-contamination factors were determined by scanning of the calibration phantoms containing known activities of 125I and $^{111}$In (FIG. 20; Table 1 and Table 2). The 3D ROIs drawn on the entire ampoules and unmixed images were calculated by the arithmetic on the images, not from the ROI data.

TABLE 1

Total activity counts from calibration images (FIG. 20) after unmixing $^{125}$I and $^{111}$In signals.

| Image | $^{125}$I ampoule | $^{111}$In ampoule |
|---|---|---|
| $^{125}$I | 21.3 | 2.25 |
| $^{111}$In | 0.10 | 56.5 |

TABLE 2

Efficiency and cross-contamination factors.

| Facture | Measured/nominal | Value |
|---|---|---|
| $e_I$ | 21.29/76 | 0.280 |
| $e_{In}$ | 56.47/87 | 0.650 |
| $C_{In>I}$ | 2.25/87 | 0.026 |
| $C_{I>In}$ | 0.10/76 | 0.001 |

The efficiency values represent the calibrated activities measured in the iodine or indium windows divided by the known activity of the sample.

Example 7. Caspase-3 Mediated Hydrolysis

Figure 21:
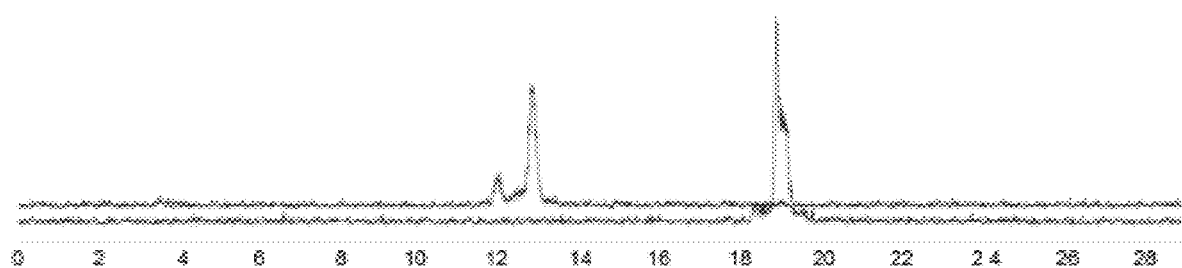
FIG. 21 depicts a radiochromatogram of [$^{125}$I]LS370 hydrolysis by caspase-3 (90 min). The [$^{125}$I]LS370 eluted at 19.5 min. Cleaved fragments eluted at 12.5 and 13 min.

FIG. 21 shows that [$^{125}$I]LS370 eluted at 19.5 min, and in the presence of caspase-3, the cleaved fragments eluted at 12.5 and 13 min. The presence of two radiolabeled peaks on the radiochromatogram suggests the formation of dimer caused by the expected oxidation of the thiol group to form intermolecular disulfide bond. However, the dimer readily converts back to single molecules under the high reducing conditions such as used to prepare the $^{99m}$Tc chelate. Kinetic analysis of caspase-3 activation with [$^{125}$I]LS370 using a radionuclide detector (radio-high-performance liquid chromatography) gave a $K_M$ and $k_{cat}$ of 15±3 1 µM and 1.02±0.06 M s$^{-1}$, respectively. These parameters compared favorably with a standard caspase-3 substrate Ac-DEVD (SEQ ID NO:2)-pNA ($K_M$=11 µM and $k_{cat}$=2.4 M s$^{-1}$), demonstrating that the radiolabeled peptide was recognized by caspase-3.

Example 8. Cell-Uptake Assays

Figure 22:
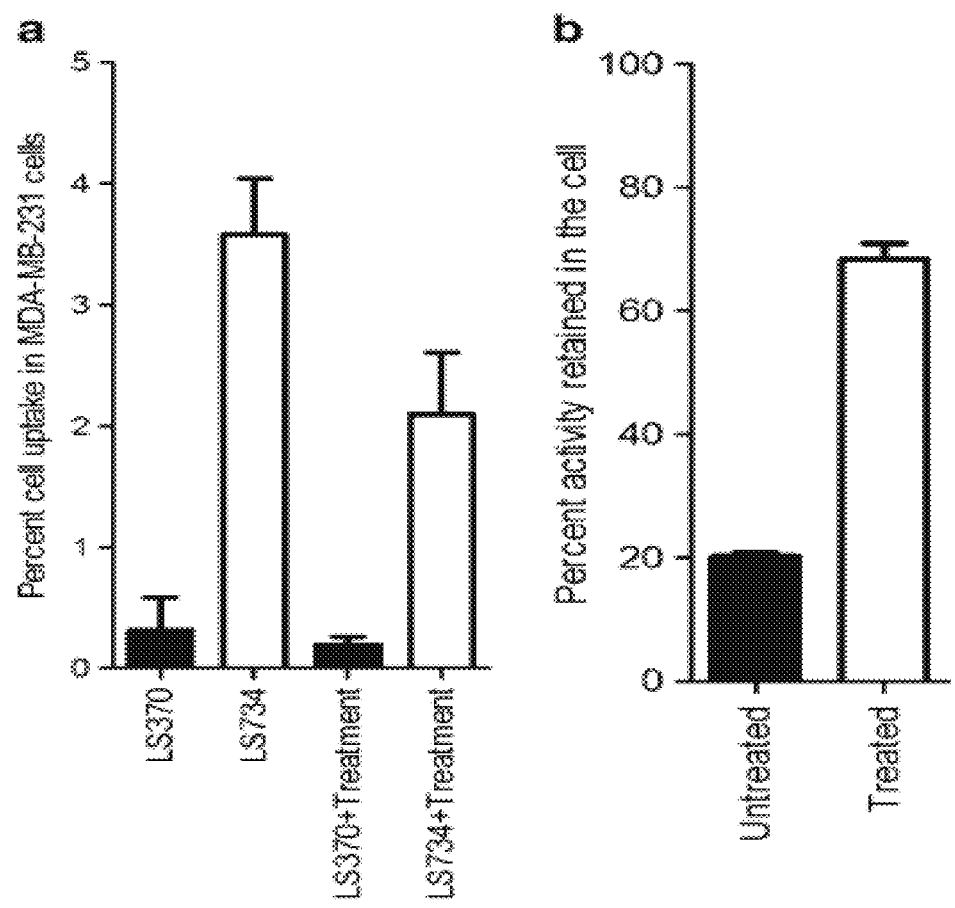
FIG. 22 depicts cell-uptake of [$^{125}$I]LS370 and [$^{125}$I]LS734 after 2 h incubation in the presence and absence of treatment (a) and depicts the efflux profile of [$^{125}$I]LS734 (b).

The goals of the cell-uptake studies were to (1) assess any changes in the structure-activity relationship resulting from the modular and responsive probe design and (2) evaluate the retention of the iodine containing hydrophobic peptide moiety in treated and untreated cells. Metastatic human breast MDA-MB-231 cells were used to evaluate whether the amino acid sequence modulation would enhance internalization, and how the probe would respond (intracellular) postchemotherapy. In the untreated cells, there was a higher uptake (P<0.001) of [$^{125}$I]LS734 (3.6±0.5) than [$^{125}$I]LS370 (0.3±0.3) at 2 h postincubation at 37° C. (FIG. 22A). The same trend was observed with the treated cells. The amount of iodinated fraction released by the untreated and treated cells at 3 h (post 2 h incubation and removal of excess activity) was used as a measure of the efflux activity. The results showed that higher amount of activity was released from untreated cells compared to treated cells that had been incubated with [$^{125}$I]LS734 (P<0.001) (FIG. 22B).

Example 9. Biodistribution

Figure 23:
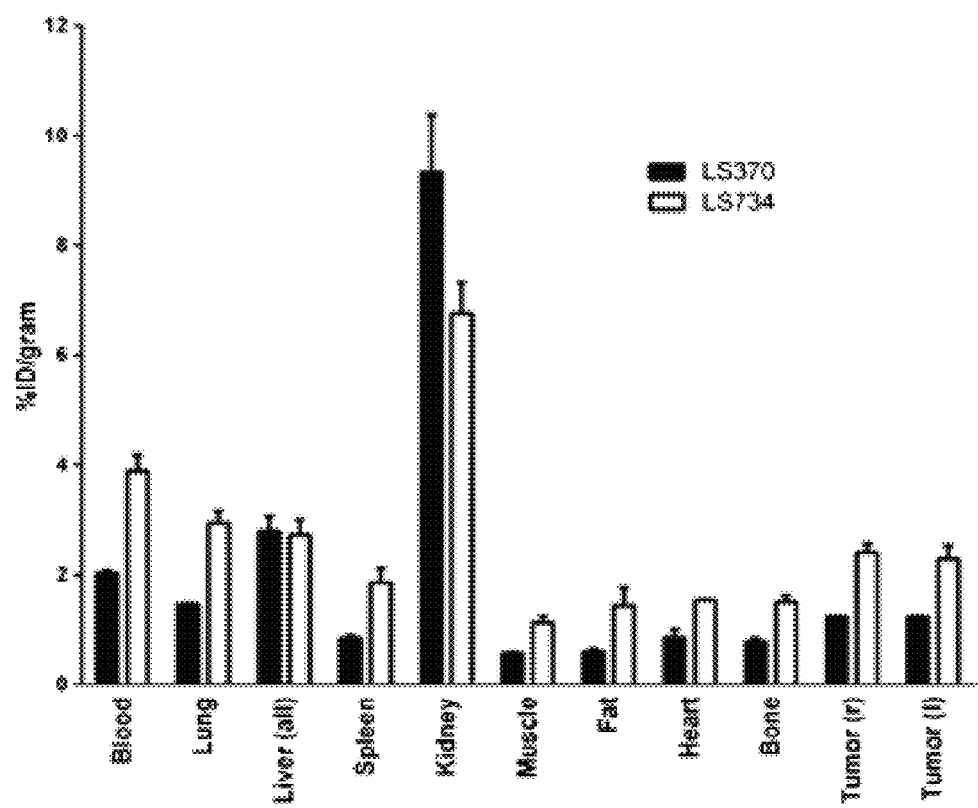
FIG. 23 depicts tissue bio-distribution of [$^{125}$I]LS370 and [$^{125}$I]LS734 1 h after administration of 4-7 µCi of the respective radiopharmaceutical.
Figure 26:
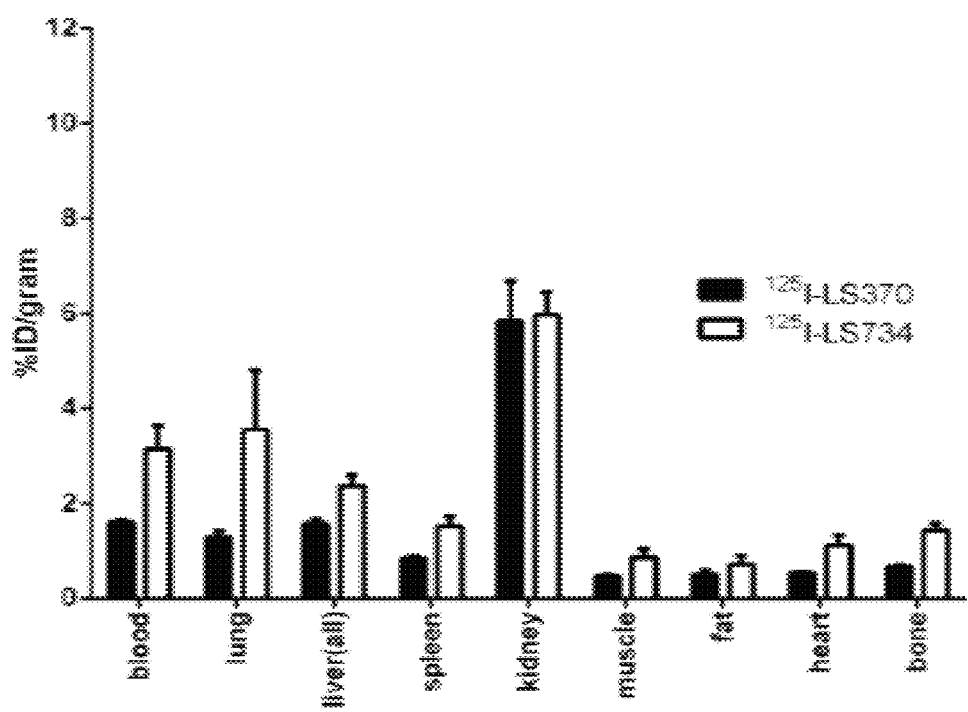
FIG. 26 depicts tissue bio-distribution of $^{125}$I-LS370 and $^{125}$I-LS734 in tumor naïve Balb/c mice after 1 h of administration of 4-7 µCi of the respective radiopharmaceutical.

The structure-activity relationship was evaluated in vivo by performing a tissue biodistribution study in naive (FIG. 26) and tumor-bearing Balb/c mice (FIG. 23). At 1 h, [$^{125}$I]LS734 circulated longer in blood as compared to [$^{125}$I]LS370. The tumor/blood ratios for both [$^{125}$I]LS370 and [$^{125}$I]LS734 was 0.6±0.03. The tumor/muscle ratios were similar as well but higher than the tumor/blood ratios, [$^{125}$I]LS734 (2.2±0.1) and [$^{125}$I]LS370 (2.1±0.3). Thyroid uptake was 73±21 and 115±73 for [$^{125}$I]LS370 and [$^{125}$I]LS734, respectively.

Example 10. Dual-SPECT Imaging of Spontaneous Breast Tumor Mouse Model after Injection of [$^{125}$I]-[$^{111}$In]LS734

Figure 24:
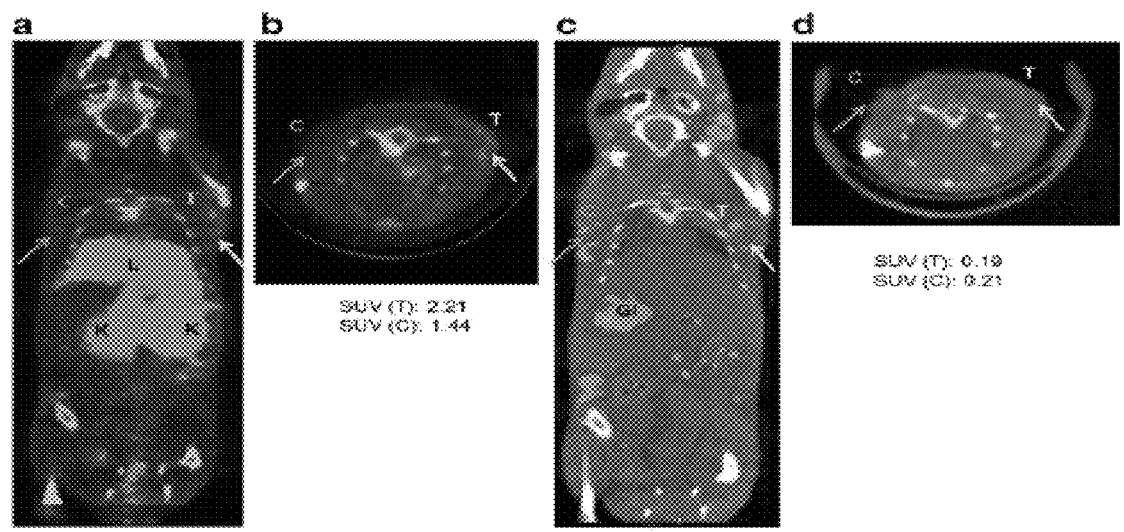
FIG. 24 depicts SPECT-CT images (single slice) after unmixing for high energy window for $^{111}$In detection (170-250 keV) and for low energy window consisting of primarily $^{125}$I activity (20-40 keV), collected at 4 h after injection of [$^{111}$In]-[$^{125}$I]LS734. (a,b) $^{111}$In window: higher activity was detected in the treated tumor (T) than the saline control treated tumor (C). The kidneys (K) had highest signal followed by the liver (L) indicating fast clearance of the $^{111}$In labeled probe and fragments. (c,d) $^{125}$I window: activity was detected in both tumors, presumably preferential retention of the lipophilic fragment although activity gastrointestinal tract (GI) and thyroid glands indicates partial physiological deiodination, most likely a function of normal as well as tumor mediated. Therefore, reported SUV values for $^{125}$I include peptide-bound and free fractions. High activity in the liver and GI indicates hepatobiliary clearance of the lipophilic $^{125}$I fragments.
Figure 27:
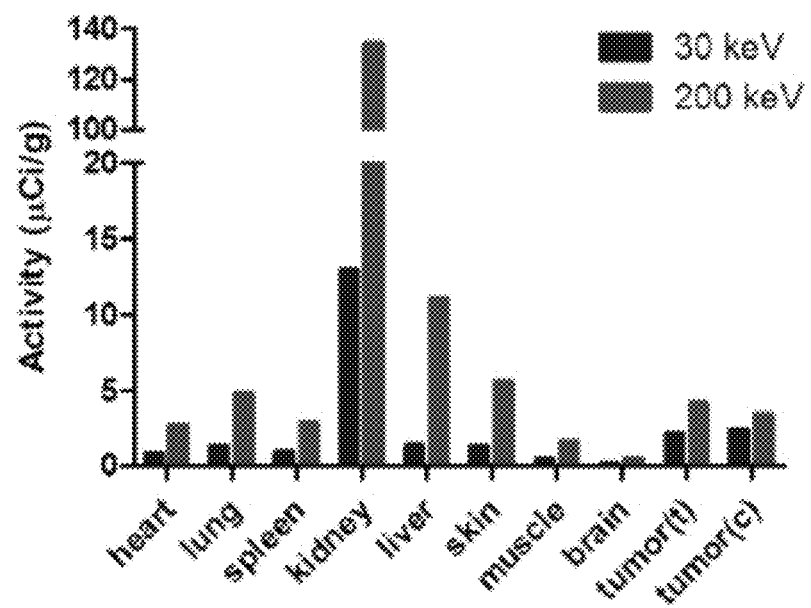
FIG. 27 depicts biodistribution analysis for $^{125}$I and $^{111}$In fragments of LS734 in mouse tissues 4 h after intravenous injection. The 30 keV signal is mixture of $^{125}$I and $^{111}$In decay and demonstrates significant difference in biodistribution from the $^{111}$In individual signal about 200 keV.

Based on the results obtained for the unmixing of $^{125}$I and $^{111}$In detection windows in calibration phantoms, a proof-of-principle in vivo imaging study was performed using the dual radiolabeled [$^{125}$I]-[$^{111}$In]LS734 to determine the tumor response to therapy in a MMTV-PyMT transgenic mouse model of spontaneous breast cancer. Reconstruction of raw data from both the low- and high-energy collection windows demonstrated differential biodistribution of [$^{125}$I]-[$^{111}$In]LS734 throughout the animal (FIG. 24). At early time points, high uptake of an iodinated moiety, resulting from the deiodination of the parent compound, was observed in the thyroid glands. Rapid clearance of $^{111}$In peptide conjugate was indicated by high activity in the kidneys and bladder. Sequential analysis by unmixing of the low-energy window further differentiated the biodistribution of $^{125}$I— and $^{111}$In-labeled compound and its fragments. Some tumor-independent proteolysis of the compound is expected due to minor activity of caspases and proteases in other tissues, particularly the liver and the kidneys. Early clearance of the $^{125}$I-labeled moieties is evident by the relatively high signal from the gastrointestinal tract in the low-energy window (FIG. 24C). While the iodine containing component was designed to be hydrophobic upon cleavable and separation from the parent compound, the $^{111}$In containing fraction was conceptualized to be hydrophilic following separation from the dual-labeled peptide. Although partial clearance from the liver was observed, the high signal from the kidneys and bladder demonstrated preferential renal to hepatobiliary clearance for the $^{111}$In containing fragments. SUV analysis of the drug-treated and saline-treated tumors showed higher signal in the $^{111}$In channel for the treated (SUV, 2.21) as compared to untreated (SUV, 1.44) tumor. The SUV analysis in the $^{125}$I channel was also quantifiable but confounded by systemic deiodination (treated SUV, 0.19 and saline-treated SUV, 0.21). The ex vivo biodistribution corroborated the in vivo image analysis (FIG. 27).

Discussion for Examples 4-10

In the preclinical arena, optical imaging has been used to report a plethora of molecular processes. With its diverse contrast mechanisms, optical imaging is amenable to high throughput screening, real-time feedback, and highly sensitive detection schemes without the use of ionizing radiation or expensive imaging systems. A unique feature of optical imaging is the detection of the expression and the functional status of proteases with high detection sensitivity using activatable reporter probes. Particularly, the commonly used Forster resonance energy transfer (FRET) method for imaging proteases is attractive for studying the functional status of these enzymes because of the near-zero background fluorescence before enzyme activation, resulting in high detection sensitivity and specificity [16-19]. Despite its enormous potential to unravel the molecular basis of diseases in vivo, the limited tissue penetration depth precludes using optical imaging techniques for noninvasive imaging of deep-seated primary and metastatic tumors.

Although radionuclide signal cannot be quenched or amplified in the same manner as fluorescence activatable probes, direct readout of protease activity can be achieved by ratiometric SPECT approach. To accomplish this goal, we have designed a dual radionuclide-labeled molecular probe and a SPECT imaging approach for quantitative measurement of protease activity. Our approach is versatile, with potential application in determining the functional status of both intracellular and extracellular proteases. Using a caspase-3 cleavable peptide sequence, we demonstrated that the chemical scaffold on the molecules can be used to alter the cellular internalization and efflux profile of the compounds. For example, the presence of positively charged amino acid residues in LS734 significantly enhanced cell internalization relative to LS370. Further, the ratio of retained activity from the hydrophobic moiety of $^{125}$I-LS734 was higher in the treated cells in vitro versus non-treated cells.

Figure 28:
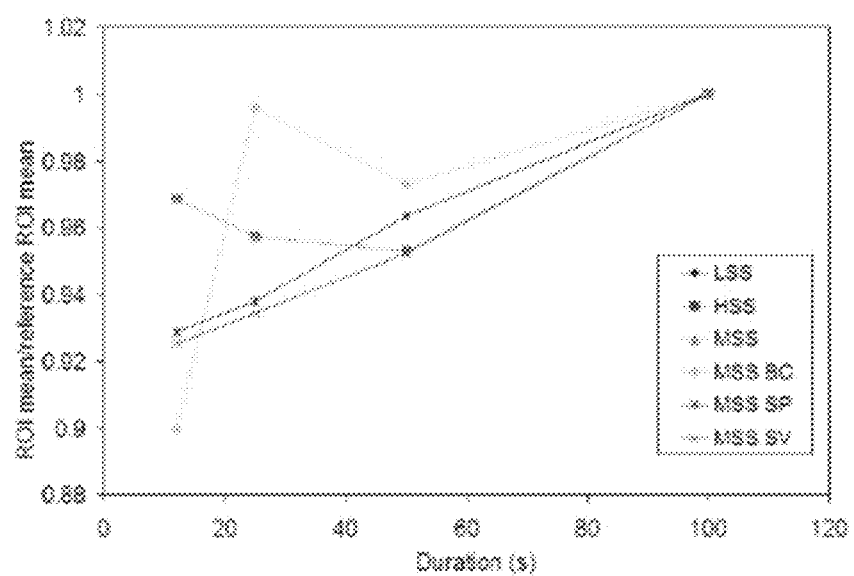
FIG. 28 depicts the ratio of the mean ROI value and the reference mean ROI value vs the scan duration (counting statistics) with various reconstruction options. The standard number of iterations (9) and standard pixel size (0.3 mm) were used in the reconstruction for all low, medium, and high background corrections (i.e. LSS, MSS, HSS corresponding to Low, Medium and High background correction for Standard number of iteration (9) and Standard pixel size 0.3 mm), and the BC, SP, and SV options were separately applied to the MSS reconstruction.
Figure 29:
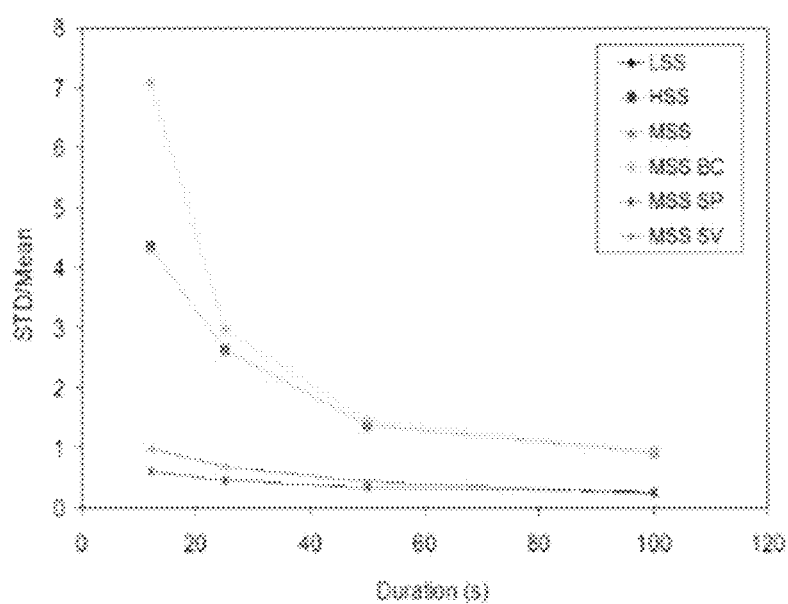
FIG. 29 depicts the coefficient of variation (STD/mean) for the ROI values vs the scan duration (counting statistics) with various reconstruction options; the standard number of iterations (9) and standard pixel size (0.3 mm) were used in the reconstruction for all low, medium, and high background corrections (i.e. LSS, MSS, HSS), and the BC, SP, and SV options were separately applied to the MSS reconstruction.

Quantitative accuracy and statistical reconstruction for dual-SPECT isotopes was developed using the available NanoSPECT image reconstruction software. The software design offers select options for three parameters: background correction (in projection data) prior to reconstruction (low, medium, and high), number of iterations (fast, standard, and fine corresponding to 6, 9, and 21 ML-EM iterations), and the pixel size (0.2, 0.3, and 0.4 mm). The standard parameters are low background correction, 9 iterations, and 0.3 mm pixel size. The reconstruction software for the NanoSPECT was evaluated at various scan durations (i.e., counting statistics) with various options within the reconstruction such as the background clean (BC), smooth projection (SP), and smooth volume (SV) using a uniform phantom. We demonstrated that the different levels of background correction (low, medium, and high) did not make any difference in the image. Furthermore, the noise properties for these parameters were identical, as seen on the images using the standard number of iterations (9) and the standard pixel size (0.3 mm; see FIG. 28). We postulated that the background subtraction was needed to be used in conjunction with the BC option to make a difference. We also observed that the BC option preserved the highest accuracy since the mean ROT values at various scan durations match closely to the reference mean ROT value (i.e., value obtained from the highest counting statistics) compared to the reconstruction with the other options. However, at the lowest counting statistics, the BC option produces the lowest accuracy. This is probably due to bias generated from the background subtraction at low counts. In contrast, the default reconstruction with no additional option produces the highest accuracy at the lowest counting statistics compared to the rest. With regard to the coefficient of variation (STD/mean) of the ROT values (FIG. 29), the BC option showed the highest variation as expected, whereas the SP option depicts the lowest.

Figure 30A:
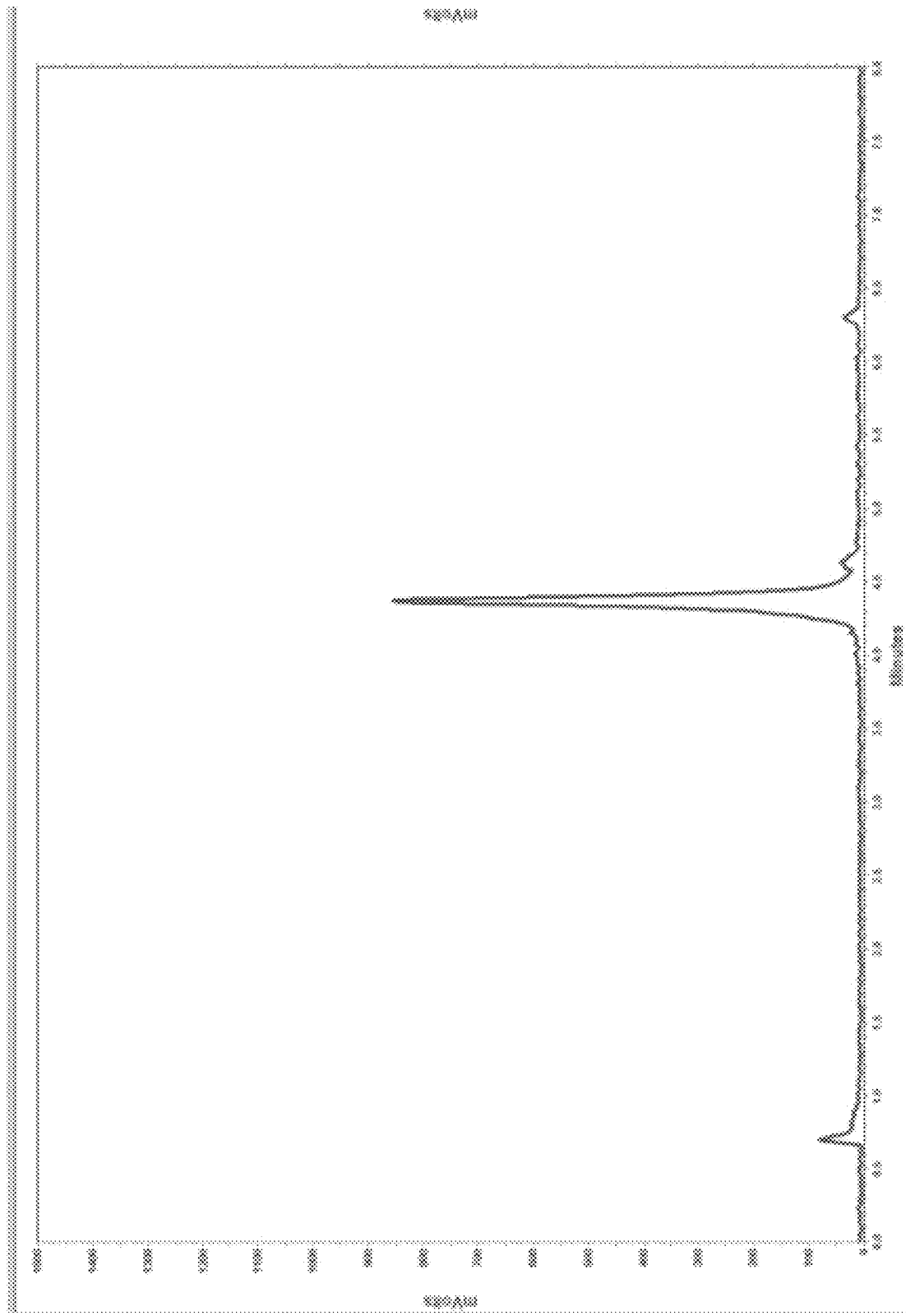
FIG. 30A-30B depicts the radio-HPLC chromatogram of $^{125}$I-LS734 at two different time points. The radio-HPLC-QC trace obtained right after the purification of the iodinated product (LS734). The sample was stored in PBS for up to 48 h (FIG. 30A). The radio-HPLC-QC trace obtained at 48 h (FIG. 30B).
Figure 30B:
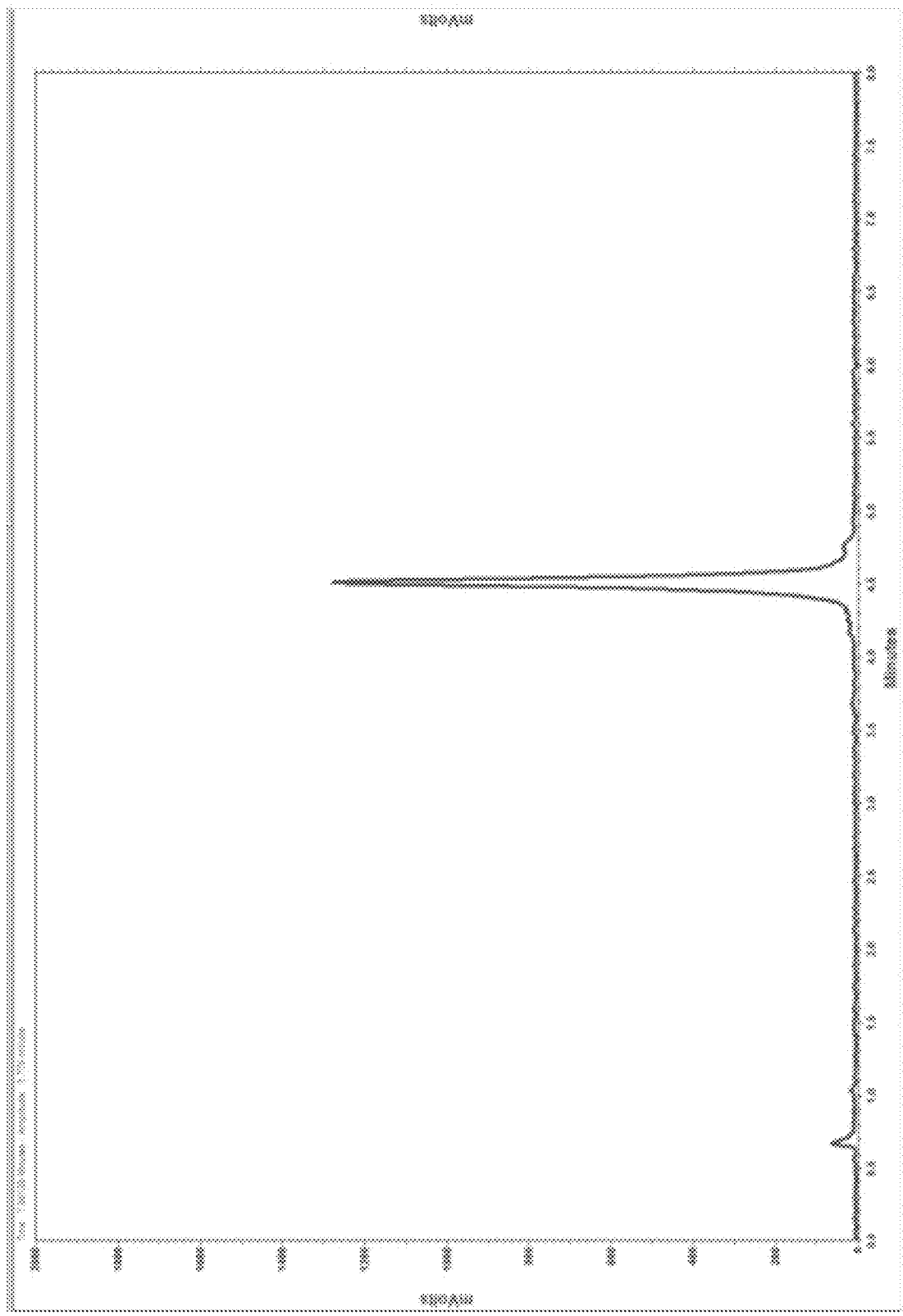

The pharmacokinetic profile in rodents demonstrated the differences in the blood circulation and tissue retention of the bioconjugates. Proof-of-principle animal imaging was performed in the MMTV-PyMT transgenic breast cancer model using the phantom validated customized attenuation and gamma-energy deconvolution SPECT/CT protocols. Cell studies demonstrated differences in the uptake of the dual radiotracer between the treated and nontreated groups. The iodine label was stable in the conditions used for the cell studies (FIG. 30A and FIG. 30B). However, a key limitation of compound design was the significant $^{125}$I uptake in the thyroid tissue, most likely a function of normal as well as tumor mediated physiologic deiodination caused by the labile carbon-iodine bond [20]. Tn designing the dual radiolabeled imaging agent, we expected that the intracellular caspase-3 cleavage of the multifunctional molecular agent would result in the trapping of the $^{125}$I-labeled hydrophobic component, while the $^{111}$In-labeled moiety will be cleared. Clearly, deiodination confounded accurate systemic data analysis. In the $^{111}$In channel, the SUV analysis of the drug- and saline-treated tumors showed higher signal for treated (2.21) versus untreated tumors (1.44). In spite of in vivo deiodination, quantitative ROT analysis of various tissues in the $^{125}$I channel was feasible using the described algorithm. The proof-of-principle animal study and the phantom studies have laid the foundation for future noninvasive dual radionuclide SPECT studies for imaging intracellular protease activity in response to treatment using biostable imaging probes. We are currently designing imaging agents that better shield the radio-halogen from systemic enzymatic cleavage [21].

In conclusion, we developed a new approach for imaging protease activity in vivo via a ratiometric SPECT imaging strategy. The synthetic method is modular, which facilitates adaptation of the method to monitor the activities of other diagnostic proteases. Attenuation correction parameters for image reconstruction and quantitative analyses were optimized using phantoms, and successfully implemented for multispectral SPECT image analysis. By modeling the crosstalk between radioisotopes, the SPECT method provides quantitative accuracy for determining the ratios of each radionuclide. This strategy can potentially be adapted to current clinical imaging systems to provide a direct measure of diagnostic molecular biomarkers of early response to therapy.

Methods for Examples 4-10

The chelator DOTA-tris(t-Bu ester) was purchased from Macro-cyclics (Dallas, Tex., USA). Acetic anhydride, N,N-diisopropylethyl-amine, trifluoroacetic acid (TFA), acetonitrile (ACN), piperidine, anisole, and dimethylformamide (DMF) were purchased from Sigma Aldrich (St. Louis, Mo., USA). All the Fmoc amino acids, hydroxybenzotriazole (HOBt), and 2-(1H-benzotriazole-1-yl)-1,1,3,3-tetramethyl-uronium hexafluorophosphate (HBTU) were purchased from AAPPtec (Louisville, Ky., USA). Na [$^{125}$I]Iodide was ordered from American Radiolabeled Chemicals, Inc. (St. Louis, Mo., USA), [$^{111}$In]InCl$_3$ was ordered from Nordion Inc. (Ottawa, ON, Canada), and $^{99m}$Tc was obtained from Mallinckrodt Pharmaceuticals, St. Louis.

Radiochemistry $^{125}$I-Labeling-LS370 or LS734 (10 µg) was dissolved in 100 µL of 0.1 M Tris (hydroxymethyl) aminomethane-hydrochloride (Tris-HCl) buffer, pH 7.6, and iodinated with 1.0 mCi Na $^{125}$I, using 2 µg Iodogen (Pierce, Rockford, Ill., USA). After 30 min, the reaction was stopped by removing the supernatant to another vessel. Purification was performed by reverse phase-high-performance liquid chromatography RP-HPLC on the C18 column (Supelcosil ABZ+ PLUS, HPLC Column, 150×4.0 mm, 5 µm) with a gradient of H$_2$O containing 0.1% TFA and ACN containing 0.1% TFA for 30 min at a flow rate of 1 mL/min. The quality control (QC) testing of the radiochemical purity was done by RP-HPLC on the C18 column (Alltima HP, HPLC Column C18, 3µ, 53×7 mm) with the gradient elution with H$_2$O containing 0.1% TFA and ACN containing 0.1% TFA for 8 minutes at a flow rate of 2.5 m L/m in. Radioactivity of each fraction was determined by γ-counting. $^{125}$I-LS734 eluted at 12.5 min and $^{125}$I-LS370 eluted at 12 min. The radiochemical purities of peptides used in this study was >95%.

$^{111}$Indium Labeling of LS734

LS734 (20 µg) in 0.1 M acetic acid (300 µL) was added to $^{111}$In (2 mCi) in 0.02 M HCl (100 µL), and the mixture was incubated for 30 min at room temperature. The reaction was applied to RP-HPLC in 0.1% TFA and purified by chromatography on a C18 reverse phase column (Waters, Milford, Mass., USA). $^{111}$In-LS734 was obtained by linear gradient elution consisting of solvent A (0.1% TFA in water) and B (0.1% TFA in ACN) (1 mL/min flow rate, 30 min). Radioactivity of each fraction was determined by γ-counting. The radiochemical purity by HPLC was >95%.

Dual $^{125}$I/$^{99m}$Tc-Labeling

To synthesize the dual-labeled $^{125}$I/$^{99m}$Tc-LS370, the HPLC purified $^{125}$I-LS370 was incubated with $^{99m}$Tc-glucoheptonate in ethanol/saline (9:1) at room temperature. The progress of the reaction was monitored via a radio-TLC scanner using water as eluent. While the dual labeled $^{125}$I/$^{99m}$Tc-LS370 probe was found to be retained at the origin, the excess $^{99m}$Tc-glucoheptonate eluted with the solvent front. A mobile eluent mixture of methanol/saline/TFA (90:8:2) and radio-TLC scanner was used to confirm the absence of any $^{99m}$Tc oxides in the dual labeled peptide. The peptide eluted with the solvent front under these conditions without significant retention at the origin, indicating completion of ligand exchange reaction and lack of any $^{99m}$Tc oxides in the preparation. Following the completion of the ligand-exchange reaction, the dual-labeled $^{125}$I/$^{99m}$Tc-LS370 probe was further purified on HPLC system equipped with the radio-detector and C-18 column. While the excess $^{99m}$Tc-glucoheptonate eluted with the injection front, the dual-labeled $^{125}$I/$^{99m}$Tc-LS370 peptide showed retention times that are about 2 min faster than the single labeled $^{125}$I-LS370 peptide alone. Additionally, the formation of the dual-labeled probe was also confirmed using the nano-SPECT. Finally, appropriate fractions of the dual labeled $^{125}$I-$^{99m}$Tc-LS370 were collected and reconfirmed via radio-TLC. Radiochemical purity was >98%.

Dual $^{125}$I/$^{111}$In-Labeling

LS734 (20 µg) was dissolved in Tris-HCl buffer (0.1 M, 100 µL, pH 7.6) and iodinated with Na $^{125}$I (2.0 mCi) using 2 µg Iodogen (Pierce, Rockford, Ill., USA). After 30 min, the reaction was stopped by transferring the solution into another tube. QC was performed on $^{125}$I-LS734 (5 µL) by radio-HPLC. For the subsequent $^{111}$In labeling, acetic acid (400 µL, 0.1 M) and $^{111}$In (10 µL, 2 mCi) in HCl (0.02 M) was added to the iodinated fraction and the mixture was incubated for 30 min at room temperature. After reaction, the mixture was purified by RP-HPLC on a C18 column (Waters, Milford, Mass., USA). $^{125}$I-$^{111}$In-LS734 was obtained and purified by linear gradient elution consisting of solvent A (0.1° A TFA in water) and B (0.1° A TFA in ACN) (1 mL/min flow rate, 30 min). Eluted fractions (500 µL) were collected into tubes. Radioactivity of each fraction was determined by γ-counting. The final product was >95% pure.

The achieved specific activities were: $^{125}$I-LS370: 40-50×10$^6$ MBq/mmol, $^{125}$I-LS734: 6-10×10$^6$ MBq/mmol, $^{111}$In-LS734: 12×10$^6$ MBq/mmol. The specific activity of $^{125}$I-$^{111}$In-LS734 was 3×10$^6$ MBq/mmol. We also determined the specific activity of $^{99m}$Tc-LS370 from the purified $^{125}$I-$^{99m}$Tc-LS370. Based on a specific activity of 50×10$^6$ MBq/mmol of $^{125}$I-LS370, the specific activity of $^{99m}$Tc in $^{125}$I-$^{99m}$Tc-LS370 was calculated. After 72 h of decay, 0.02% of $^{99m}$Tc remained but this fraction did not have a significant impact on the $^{125}$I counting window (15-75 keV). Based on the sum of the counts per minute (CPM) from fractions 10-12 and the counting efficiency (0.679 CPM/DPM; see FIG. 25), the calculated specific activity of $^{99m}$Tc in $^{125}$I-$^{99}$Tc-LS370 was 17×10$^{10}$ MBq/mmol. This value is in good agreement with the literature reported maximum specific activity of $^{99m}$Tc, which is ~20×10$^{10}$ MBq/mmol[17].

Caspase-3 Mediated Hydrolysis of [$^{125}$I]LS370

[$^{125}$I]LS370 was dissolved in caspase buffer {100 mM NaCl, 50 mM 4-(2-hydroxyethyl)-1-piperazineethanesulfonic acid, 10 mM DTT, 1 mM ethylenediaminetetraacetic acid, 10% glycerol, and 0.1°% 3-[(3-cholamidopropyl) dimethylammonio]-1-propanesulfonate, pH 7.4} at concentrations varying from 2.5 to 20 µM. Caspase-3 (Cal Biochem) was added to the radioactive peptide solution at a final concentration of 290 µM. These solutions were allowed to react at 37° C. for 180 min and were sampled every 30 min. Substrate hydrolysis was monitored by radio-high-performance liquid chromatography (Vydac, C-18, 4.6×250 mm, 1 ml/m, A=H$_2$O, 0.1% TFA, B=ACN, 0.1% TFA; 10-90% B, 30 min, linear gradient) of these time point samples. Comparison to a standard caspase-3 substrate (Ac-DEVD-pNA) and calculation of the enzyme kinetic parameters were carried out as previously described [12].

Cell Culture:

All cell handling was aseptically performed in a laminar flow hood. 4T1/luc murine breast cancer cells were purchased from Sibtech (Brookfield, Conn.) and MDA-MB-231 human mammary gland/breast cancer cells were purchased from the American Tissue Culture Collection (ATCC) and were grown until 60-75% confluence in T75 tissue culture flasks. The cells were grown in Dulbeccos's Modified Eagles Medium (GIBCO-BRL) with 10% fetal bovine serum and 1% penicillin/streptomycin at 37° C. in a humidified atmosphere with 5% CO$_2$ in a Revco Elite II incubator. To determine cell density, equal amounts of cell suspension and trypan blue exclusion were added to a hemocytometer to calculate a cells/mL concentration and ensure cell viability.

Cell Uptake and Efflux Studies With [$^{125}$I]L734 or [$^{125}$I]LS370

MDA-M B-231 cells used for the uptake and efflux assay were grown on 24-well tissue culture plates until they were 80-90% confluent with ~250,000 cells per well. A two-component chemotherapeutic regimen was used that has been shown to initiate apoptosis in breast cancer cells and xenografts [13,14]. The experimental treatment group of cells was treated with 10 ng/ml of SN-38 (7-ethyl-10-hydroxy-camptothecin, Sigma Aldrich) for 24 h. Then, the SN-38 was removed, and the second chemotherapeutic drug, UCN-01 (Sigma Aldrich), was introduced at a concentration of 1 tM in 0.1% BSA per well. At this point, respective radioactive solutions ([$^{125}$I]LS734 or [$^{125}$I]LS370, 0.02 µg per well; specific activities: [$^{125}$I]LS370-40×10$^6$ MBq/mmol; [$^{125}$I]LS734-10×10$^6$ MBq/mmol) were added to treated and control groups. The solutions were added dropwise into the wells and gently mixed to ensure homogeneous distribution. The final volume per well was 240 µl, and the plates were incubated at 37° C. (5% CO$_2$) for 2 h. After incubation, the supernatant (fraction 1) was collected, and the cells were washed twice with 250 µl of cold serum-free media. The washed cells were incubated again for 1 h in serum-free media at 37° C. (5% CO$_2$), and at 1 h, the supernatant was collected (fraction 2). Fraction 2 represents the cell efflux, which is the amount of radioactivity released from cells after the 2 h uptake. After collecting the supernatant, Solvable (PerkinElmer) was added to facilitate efficient scraping of the cells. The scraped cells (fraction 3) were collected in microfuge tubes. The radioactivity in each fraction was measured in a well counter (Packard II gamma counter).

Animal Biodistribution Studies:

All animal studies were conducted according to guidelines on the humane care and use of laboratory animals under protocols approved by the Animal Studies Committee at Washington University School of Medicine. For tissue biodistribution studies, syngeneic breast tumor models were prepared via bilateral orthotopic implantation of luciferase-transfected 4T1 mouse mammary carcinoma cells (4T1luc, 5×10$^5$ cells per tumor) in the mammary fat pads of 6-week-old, female Balb/c mice (NCI, Frederick, Md., USA). Studies were conducted when the tumors reached about 3 mm maximum diameter (~10 days). Healthy female Balb/c mice (n=4 per time point) were anesthetized with 1-2% vaporized isoflurane and injected via tail vein with 0.185 MBq of [$^{125}$I]LS370 or [$^{125}$I]LS734 (specific activities: [$^{125}$I]LS370-40×10$^6$ MBq/mmol; [$^{125}$I]LS734-10×10$^6$ MBq/mmol). At 1 h post injection, mice were killed. Organs of interest were removed and blotted dry. The radioactivity was measured in a gamma counter (Packard II gamma counter). Diluted standard doses (1:100) were prepared and counted along with the samples. Data points were corrected for radioactive decay. The percent injected dose per gram of tissue (% ID/g) was calculated.

Dual $^{125}$I-$^{111}$In Nuclides SPECT Imaging Phantom and Animal Imaging

Phantom studies were designed based on the half-life decay of $^{125}$I [t$_{1/2}$=59.4 days; X-ray: ~27.3 keV (145.2%)] and 111In [t$_{1/2}$=2.8 days; X-ray, ~23 keV (82.5%) and γ-ray, 171 keV (90.6%), 245 keV (94.1%)]. The data were acquired in two energy windows, a low-energy window for $^{125}$I (25.2-30.8 keV) and a second encompassing the two high energy peaks of $^{111}$In (140-260 keV) using the NanoSPECT/CT system (Bioscan). As a consequence of this dual-labeling strategy, $^{125}$I measurements were contaminated with $^{111}$In activity due to overlap in the X-ray energy and contamination from down scatter (photons emitted by the higher energy isotope in the energy window of the lower energy isotope). Therefore, a strategy for unmixing of the overlapping gamma ray energy signals was formulated. An unmixing strategy based on the makeup of signals in each collection window ($M_I$ and $M_{In}$) was developed:

with $e_I$ and $e_{In}$ representing the detection efficiencies for $^{125}$I and $^{111}$In in their respective window and $e_{Inx}$ the efficiency for detecting the indium X-rays in the $^{125}$In window. $C_{In>I}$ and $C_{I>In}$ are the cross-talk contamination factors from $^{111}$In into the $^{125}$I window and from $^{125}$I into the $^{111}$In window. Under these conditions, $e_{Inx}$ cannot be separated from $C_{In>I}$. $C_{I>I}$ should be small. $C_{In>I}$ is the sum from the down scatter from the 171 and 245 keV gamma rays and X-rays efficiency of $^{111}$In in the $^{125}$I window. Therefore:

The phantoms were made of two ampoules containing a calibrated amount of $^{111}$In (87 ρCi) and $^{125}$I (76 ρCi). The three-dimensional (3D) regions-of-interest (ROIs) were drawn to encompass the entire ampoules.

Dual-Isotope SPECT/CT Imaging in Spontaneous Breast Cancer Model

The MMTV-PyMT transgenic mice carrying the polyoma middle T oncogene driver by the MMTV promoter in the FVB background were bred in house(15). The animal model recapitulates the human condition of early breast tumorgenesis including complex interactions of immune cells within the tumor, and multifocal lesions throughout the mammary tissue[19]. Multifocal tumors enabled internal controls as treated and untreated tumors within the same animal. For the proof-of-principle small animal nanoSPECT imaging study, a 12 week old MMTV-PyMT female mouse was used when the bilateral tumors were palpable and greater than 3 mm diameter.

The left pectoral mammary tumor was injected intratumorally with bromopyruvate (150 µL, 1.75 µM), an inhibitor of GDPH[16]. The contralateral tumor was injected with saline. At 24 h after bromopyruvate injection, the mouse was injected intravenously with dual radiolabeled $^{125}$I-$^{111}$In-LS734 (500 µCi) and imaged with nanoSPECT 4 h post-injection. SPECT scans were performed using 16 projections, 180 s per projection. Reconstruction of SPECT and CT scans was performed using in vivo scope software (Bioscan).

Data Analysis and Statistics:

All data are presented as mean±SD. For statistical classification, a Student's t test (two-tailed, unpaired) was used to compare individual datasets. All statistical analyses were performed using Prism software. P values less than 0.05 were considered significant.

REFERENCES FOR EXAMPLE 4-10

1. Choi K Y, Swierczewska M, Lee S, Chen X (2012) Protease-activated drug development. Theranostics 2:156-178.
2. Boya P, Kroemer G (2008) Lysosomal membrane permeabilization in cell death. Oncogene 27:6434-6451.
3. Johansson A C, Appelqvist H, Nilsson C et al (2010) Regulation of apoptosis-associated lysosomal membrane permeabilization. Apoptosis 15:527-540.
4. Graham M M (2012) Clinical molecular imaging with radiotracers: current status. Med Princ Pract: Int J Kuwait University, Health Sci Centre 21:197-208.
5. Benard F, Turcotte E (2005) Imaging in breast cancer: single-photon computed tomography and positron-emission tomography. Breast Cancer Res 7:153-162
6. Chen D L, Zhou D, Chu W et al (2012) Radiolabeled isatin binding to caspase-3 activation induced by anti-Fas antibody. Nucl Med Biol 39:137-144.
7. Beekman F, van der Have F (2007) The pinhole: gateway to ultra-high-resolution three-dimensional radionuclide imaging. Eur J Nucl Med Mol Imaging 34:151-161.
8. Edwards W B, Akers W J, Ye Y et al (2009) Multimodal imaging of integrin receptor-positive tumors by bioluminescence, fluorescence, gamma scintigraphy, and single-photon emission computed tomography using a cyclic RGD peptide labeled with a near-infrared fluorescent dye and a radionuclide. Mol Imaging 8:101-110.
9. Yang T J, Haimovitz-Friedman A, Verheij M (2012) Anticancer therapy and apoptosis imaging, Exp Oncol 34:269-276,
10. Wang J, Lenardo M J (2000) Roles of caspases in apoptosis, development, and cytokine maturation revealed by homozygous gene deficiencies. J Cell Sci 113(Pt 5):753-757.
11. Ashkenazi A, Dixit V M (1998) Death receptors: signaling and modulation. Science 281:1305-1308.
12. Zhang Z, Fan J, Cheney P P et al (2009) Activatable molecular systems using homologous near-infrared fluorescent probes for monitoring enzyme activities in vitro, in cellule, and in vivo. Mol Pharmaceutics 6:416-427.
13. Ma C X, Cai S, Li S et al (2012) Targeting Chk1 in p53-deficient triple-negative breast cancer is therapeutically beneficial in human-in-mouse tumor models. J Clin Investig 122:1541-1552.
14. Bullok K E, Maxwell D, Kesarwala A H et al (2007) Biochemical and in vivo characterization of a small, membrane-permeant, caspase-activatable far-red fluorescent peptide for imaging apoptosis. Biochemistry 46:4055-4065.
15. Eckelman W C, Bonardi M, Volkert W A (2008) True radiotracers: are we approaching theoretical specific activity with Tc-99m and I-123? Nucl Med Biol 35:523-527.
16. Chau I, Rigg A, Cunningham D (2003) Matrix metalloproteinase inhibitors—an emphasis on gastrointestinal malignancies. Crit Rev Oncol Hematol 45:151-176
17. Luker G D, Luker K E (2008) Optical imaging: current applications and future directions. J Nucl Med 49:1-4.
18. Ntziachristos V, Bremer C, Graves E E, Ripoll J, Weissleder R (2002) In vivo tomographic imaging of near-infrared fluorescent probes. Mol Imaging 1:82-88
19. Bremer C, Tung C H, Weissleder R (2001) In vivo molecular target assessment of matrix metalloproteinase inhibition. Nat Med 7:743-748.
20. Glazer D I, Brown R K, Wong K K, Savas H, Gross M D, Avram A M (2013) SPECT/CT evaluation of unusual physiologic radioiodine biodistributions: pearls and pitfalls in image interpretation. Radio-graphics 33:397-418.
21. van Schaijk F G, Broekema M, Oosterwijk E et al (2005) Residualizing iodine markedly improved tumor targeting using bispecific antibody-based pretargeting. J Nucl Med 46:1016-1022.

What is claimed is:

1. A composition comprising:
(a) a peptide comprising a Tyr residue and a -Lys-Gly-Cys- group, wherein the Tyr residue is separated from the -Lys-Gly-Cys- group by a caspase-3 sensitive site, wherein the caspase-3 sensitive site comprises the amino acid sequence SEQ ID NO:2 (Asp-Glu-Val-Asp); and,
(b) two radionuclides, wherein the spectrally differentiated radionuclides are $^{125}$I and $^{99}$mTc,
wherein the radionuclides are attached to the peptide at positions separated by the caspase-3 sensitive site, which is susceptible to cleavage by caspase-3, within the peptide.

2. A method of detecting enzyme activity in a subject, the method comprising:
a) administering to the subject an effective amount of a composition of claim 1:
wherein cleavage at a caspase-3 sensitive site within the peptide results in a radiative hydrophobic peptide fragment and a radiative hydrophilic peptide fragment;
b) imaging the subject for a signal corresponding to a radionuclide radiative hydrophobic peptide fragment and a radionuclide radiative hydrophilic peptide fragment to determine a biodistribution for the radiative hydrophobic peptide fragment and the radiative hydrophilic peptide fragment;
c) comparing the biodistribution of the radionuclide radiative hydrophobic peptide fragment to the biodistribution of the radionuclide radiative hydrophilic peptide fragment,
wherein when the biodistribution for the radionuclide radiative hydrophobic peptide fragment differs from the biodistribution for the radionuclide radiative hydrophilic peptide, enzyme activity is detected.

3. The method of claim 2, wherein the subject is imaged about 4 to about 48 hours after administration.

4. The method of claim 2, wherein the subject is imaged using single photon emission computed tomography (SPECT).

5. A method of detecting enzyme activity in a subject, the method comprising:
a) administering to the subject an effective amount of a composition of claim 1;
b) imaging the subject for a signal corresponding to the $^{125}$I and $^{99}$mTc to determine a biodistribution for $^{125}$I and $^{99}$MTc; and,
c) comparing the biodistribution of $^{125}$I to the biodistribution of $^{99}$mTc,
wherein when the biodistribution for the $^{125}$I differs from the biodistribution for the $^{99}$mTc-enzyme activity is detected.

6. The method of claim 5, wherein the subject is imaged about 4 to about 48 hours after administration.

7. The method of claim 5, wherein the subject is imaged using single photon emission computed tomography (SPECT).

8. The composition of claim 1, wherein one of the radionuclides is conjugated to the Tyr residue found in the peptide.

9. The composition of claim 8, wherein the radionuclide is $^{125}$I.

10. The composition of claim 1, wherein one of the radionuclides is conjugated to the -Lys-Gly-Cys-group found in the peptide.

11. The composition of claim 10, wherein the radionuclide is $^{99m}$Tc.

12. The composition of claim 1, wherein the peptide comprises SEQ ID NO:5 (Ahx-Tyr-Ahx-Asp-Glu-Val-Asp-Gly-Lys-Cys) and Ahx is 6-aminocaproic acid.

* * * * *

UNITED STATES PATENT AND TRADEMARK OFFICE
CERTIFICATE OF CORRECTION

PATENT NO. : 11,007,286 B2
APPLICATION NO. : 15/959982
DATED : May 18, 2021
INVENTOR(S) : Samuel Achilefu and Kvar Black It is certified that error appears in the above-identified patent and that said Letters Patent is hereby corrected as shown below:

In the Claims

In Claim 12:
Column 54, Line 65-66 "SEQ ID NO:5 (Ahx-Tyr-Ahx-Asp-Glu-Val-Asp-Gly-Lys-Cys)" should be
-- SEQ ID NO: 5 (Ahx-Tyr-Ahx-Asp-Glu-Val-Asp-Gly-Lys-Gly-Cys) --.

Signed and Sealed this
Twenty-eighth Day of November, 2023

Katherine Kelly Vidal
*Director of the United States Patent and Trademark Office*